(12) United States Patent
Vouret et al.

(10) Patent No.: US 11,919,854 B2
(45) Date of Patent: Mar. 5, 2024

(54) P2RX7 MODULATORS IN THERAPY

(71) Applicants: Centre national de la recherche scientifique, Paris (FR); CHRU de Lille, Lille (FR); Universite Côte D'Azur, Nice (FR); Institut National de la Sante et de la Recherche Medicale (INSERM), Paris (FR); Université de Lille, Lille (FR); YNCREA Hauts de France, Lille (FR)

(72) Inventors: Valérie Vouret, Nice (FR); Laetitia Douguet, Bailly (FR); Alina Ghinet, Lomme (FR); Germain Homerin, Lille (FR); Benoît Guy Marie Rigo, Lille (FR); Davy Jérémy Baudelet, Paris (FR); Xavier Dezitter, Marchiennes (FR); Régis Millet, Harnes (FR); Christophe Furman, Marcq en Baroeul (FR)

(73) Assignees: CENTRE NATIONAL DE LA RECHERCHE SCIENTIFIQUE, Paris (FR); CHRU DE LILLE, Lille (FR); UNIVERSITE COTE D'AZUR, Nice (FR); INSTITUT NATIONAL DE LA SANTE ET DE LA RECHERCHE MEDICALE (INSERM), Paris (FR); UNIVERSITE DE LILLE, Lille (FR); JUNIA, Lille (FR)

( * ) Notice: Subject to any disclaimer, the term of this patent is extended or adjusted under 35 U.S.C. 154(b) by 783 days.

(21) Appl. No.: 17/042,806

(22) PCT Filed: Mar. 29, 2019

(86) PCT No.: PCT/EP2019/058013
§ 371 (c)(1),
(2) Date: Sep. 28, 2020

(87) PCT Pub. No.: WO2019/185868
PCT Pub. Date: Oct. 3, 2019

(65) Prior Publication Data
US 2021/0017131 A1 Jan. 21, 2021

(30) Foreign Application Priority Data
Mar. 29, 2018 (EP) ..................................... 18305361

(51) Int. Cl.
| C07D 207/16 | (2006.01) |
| A61K 31/4015 | (2006.01) |
| A61K 31/4025 | (2006.01) |
| A61K 31/4439 | (2006.01) |
| A61K 39/395 | (2006.01) |
| A61P 1/00 | (2006.01) |
| A61P 35/00 | (2006.01) |
| C07D 401/12 | (2006.01) |
| C07D 409/12 | (2006.01) |

(52) U.S. Cl.
CPC ........ *C07D 207/16* (2013.01); *A61K 31/4015* (2013.01); *A61K 31/4025* (2013.01); *A61K 31/4439* (2013.01); *A61K 39/395* (2013.01); *A61P 1/00* (2018.01); *A61P 35/00* (2018.01); *C07D 401/12* (2013.01); *C07D 409/12* (2013.01)

(58) Field of Classification Search
CPC combination set(s) only.
See application file for complete search history.

(56) References Cited

U.S. PATENT DOCUMENTS

| 4,217,130 A | 8/1980 | Tsuruta et al. |
| 2007/0037830 A1 | 2/2007 | Cladingboel et al. |
| 2010/0056595 A1 | 3/2010 | Beswick et al. |
| 2010/0168171 A1 | 7/2010 | Beswick et al. |

FOREIGN PATENT DOCUMENTS

| CN | 101068927 A | 11/2007 | |
| FR | 2273533 A1 | 1/1976 | |
| JP | 54-066265 | 5/1979 | |
| JP | 2007501782 | 2/2007 | |
| JP | 2011506554 A | 3/2011 | |
| JP | 2009542595 | 9/2013 | |
| WO | WO 03/045912 1 | 6/2003 | |
| WO | WO-2003045912 * | 6/2003 | ........... C07D 207/16 |
| WO | WO 2005/014529 A1 | 2/2005 | |
| WO | WO 2008003697 A1 | 1/2008 | |
| WO | WO 2009077559 A2 | 6/2009 | |

OTHER PUBLICATIONS

Alves LA, Bezerra RJ, Faria RX, Ferreira LG, da Silva Frutuoso V. Molecules. Sep. 5, 2013;18(9):10953-72. doi: 10.3390/molecules 180910953. PMID: 24013409; PMCID: PMC6270334. (Year: 2013).*
Crusz SM, Balkwill FR. Inflammation and cancer: advances and new agents. Nat Rev Clin Oncol. Oct. 2015;12(10):584-96. doi: 10.1038/nrclinonc.2015.105. Epub Jun. 30, 2015. PMID: 26122183. (Year: 2015).*
Lichtman MA. A Bacterial Cause of Cancer: An Historical Essay. Oncologist. May 2017;22(5):542-548. doi: 10.1634/theoncologist .2017-0007. Epub Apr. 21, 2017. PMID: 28432224; PMCID: PMC5423514. (Year: 2017).*
Wan Y, Li Y, Yan C, Yan M, Tang Z. Indole: A privileged scaffold for the design of anti-cancer agents. Eur J Med Chem. Dec. 1, 2019;183:111691. doi: 10.1016/j.ejmech.2019.111691. Epub Sep. 11, 2019. PMID: 31536895. (Year: 2019).*

(Continued)

Primary Examiner — Adam Weidner
Assistant Examiner — Laura Ann Essex
(74) Attorney, Agent, or Firm — Knobbe Martens Olson & Bear LLP

(57) ABSTRACT

The present invention relates to compounds of formula (I), their enantiomers and their pharmaceutically acceptable salts, and their use in therapy, particularly for the treatment of cancer or inflammatory diseases.

15 Claims, 26 Drawing Sheets

(56) References Cited

OTHER PUBLICATIONS

Figure 1:
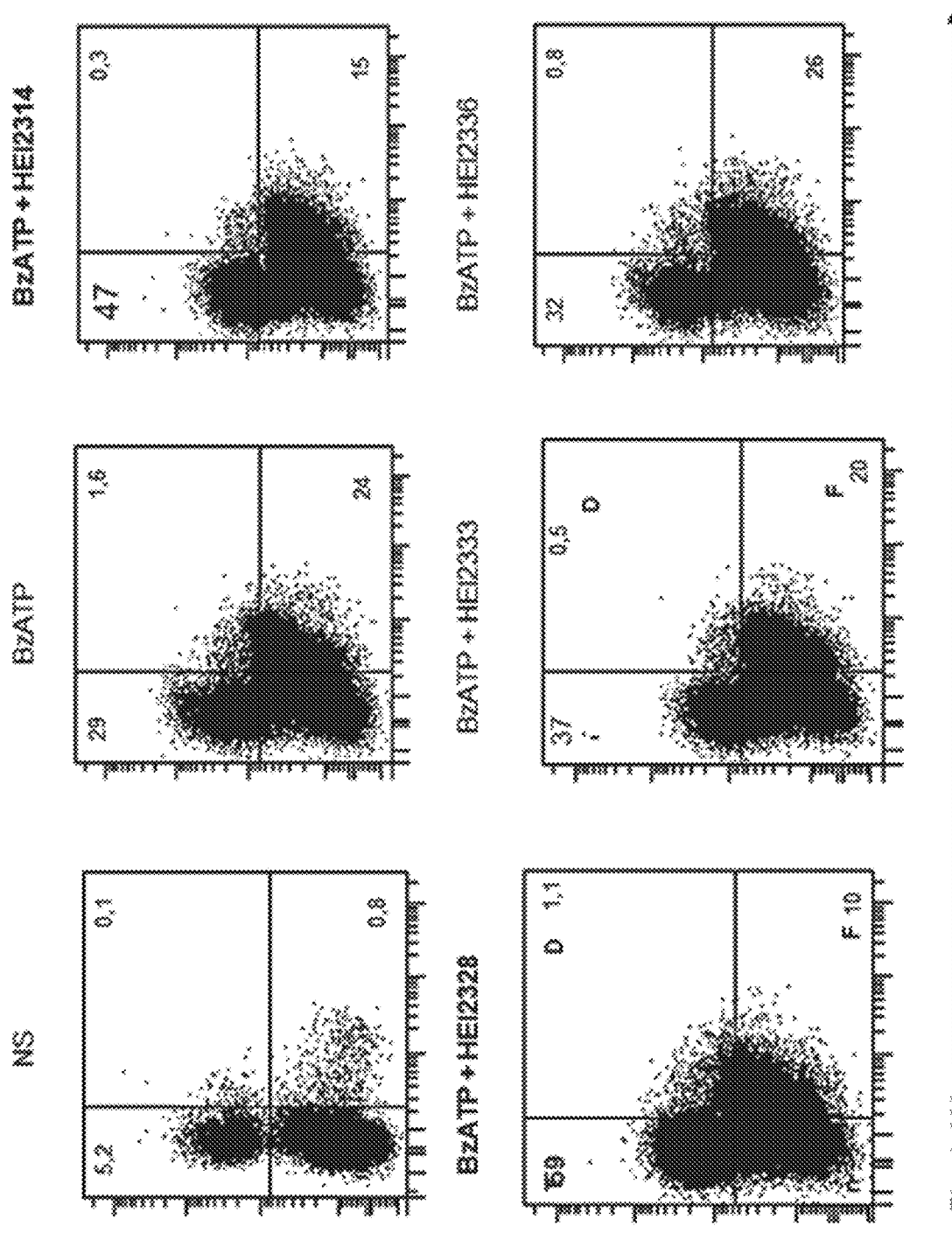

Rashid Hu, Xu Y, Muhammad Y, Wang L, Jiang J. Research advances on anticancer activities of matrine and its derivatives: An updated overview. Eur J Med Chem. Jan. 1, 2019;161:205-238. doi: 10.1016/j.ejmech.2018.10.037. Epub Oct. 19, 2018. PMID: 30359819. (Year: 2018).*
Garewal HS, Ramsey L, Kaugars G, Boyle J. Clinical experience with the micronucleus assay. J Cell Biochem Suppl. 1993;17F:206-12. doi: 10.1002/jcb.240531031. PMID: 8412196. (Year: 1993).*
International Search Report, PCT/EP2019/058013, dated Jul. 4, 2019.
European Search Report, in EP Patent Application No. EP18305361, dated Sep. 7, 2018.
Baudelet, Davy, et al., "Evaluation and comparison of three different separation techniques for analysis of retroamide enantiomers and their biological evaluation against h-P2Xy7 receptor," Journal of chromatography B, Feb. 9, 2015, 986-987: pp. 35-43.
Homerin, Germain, et al., "ZrCl$_4$ as a new catalyst for ester amidation: an efficient synthesis of h-P2X7R antagonists," Tetrahedron Letters, vol. 57, No. 10, Mar. 1, 2016., pp. 1165-1170.
Di Virgilio et al., "The P2X7 Receptor in Infection and Inflammation", Immunity 47: 15-31, Jul. 2017.
Meng Shuangping, 2016, Master's Degree Thesis of Second Military Medical University "A Study of the Role and Mechanism of P2X7 Receptor in the Progression of Colitis-Associated Cancer(CAC)", in 94 pages.
Von Helmet Stamm and Jochen Budny "Verbesserte Synthese von 1.3-Diacyl-2-pyrrolidonan" Chemiker-Zeitung 1979 103: 156-157.
Crusz et al., "Inflammation and cancer: advances and new agents". Nature Reviews, Clinical Oncology, vol. 12, Oct. 2015, pp. 584-596.
Rashid et al., "Research advances on anticancer activities of matrine and its derivatives: An updated overview". European Journal of Medicinal Chemistry, 161(2019) pp. 205-238.
Lichtman et al., "A Bacterial Cause of Cancer: An Historical Essay". The Oncologist, 2017; 22: 542-548.
Alves et al., "Physiological Roles and Potential Therapeutic Applications of the P2X7 Receptor in Inflammation of Pain". Molecules, 2013, 18: 10953-10972.
Wan et al., "Indole: A privileged scaffold for the design of anticancer agents", European Journal of Medicinal Chemistry 183 (2019) 111691 (in 18 pages).
Garewal et al., "Clinical Experience With the Micronucleus Assay". Journal of Cellular Biochemistry, Supplement 17F: 206-212 (1993).

* cited by examiner

P2RX7 MODULATORS IN THERAPY

The present invention concerns compounds of formula (I), their enantiomers and their pharmaceutically acceptable salts, and their use in therapy, particularly for the prevention and/or treatment of cancer or inflammatory diseases.

Inflammation is a key protective response and most of the mechanisms that link inflammation to damage repair and regeneration are conserved within evolution (Karin, M. and Clevers, H. *Reparative inflammation takes charge of tissue regeneration*. Nature, 2016. 529: p. 307-315). Inflammation is a finely tuned response; perturbation of this response leads to many chronic and degenerative diseases. Of particular interest, epidemiologic studies underline the link between chronic inflammation and cancer. In this context, development of new strategies to treat inflammation and resulting pathologies is urgently needed, in view of the long term effectiveness of existing treatments.

The death of normal or tumor cells produces danger-associated molecular patterns (DAMP), such as ATP, which is normally inside the cells. Purinergic receptors from the P2X family are ATP-gated-cation channels formed by three protein monomers. Among the seven receptor members, receptor P2X7 (encoded by gene P2RX7) is the only one having the potential to mediate large pore formation and ultimately cell death in a microenvironment rich of extracellular ATP. P2RX7 is expressed by immune and non-immune cells.

The potential of P2RX7 to establish finely tuned inflammatory responses was already highlighted; also the ability of P2RX7 antagonists to increase tumor incidence in an in situ mouse model of colitis-associated cancer was shown (Cesaro, A., et al., *Amplification loop of the inflammatory process is induced by P2X7R activation in intestinal epithelial cells in response to neutrophil transepithelial migration*. Am J Physiol Gastrointest Liver Physiol, 2010. 299(1): p. G32-42; Hofman, P., et al., *Genetic and Pharmacological Inactivation of the Purinergic P2RX7 Receptor Dampens Inflammation but Increases Tumor Incidence in a Mouse Model of Colitis-Associated Cancer*. Cancer Res, 2015).

Besides, most of the existing treatments against chronic inflammation or cancer deregulate immune cell response.

During the last decade, immunotherapies (anti-PD-1, anti-PD-L1 or anti-CTLA-4 antibodies) revolutionized the treatment of melanoma and lung cancer (NLSCC) (Sharma, P. and J. P. Allison, *The future of immune checkpoint therapy*. Science, 2015. 348(6230): p. 56-61). These therapies reverse immune checkpoints to amplify T cell responses and decrease immunosuppression within the tumor microenvironment (TME). However, some patients with high PD-L1 expression levels are resistant to treatment (McLaughlin, J., et al., *Quantitative Assessment of the Heterogeneity of PD-L1 Expression in Non-Small-Cell Lung Cancer*. JAMA Oncol, 2016. 2(1): p. 46-54). The anti-tumor activity of T lymphocytes is also blunted by myeloid-derived suppressor cells (MDSC) attracted within the TME (Anderson, K. G., I. M. Stromnes, and P. D. Greenberg, *Obstacles Posed by the Tumor Microenvironment to T cell Activity: A Case for Synergistic Therapies*. Cancer Cell, 2017. 31(3): p. 311-325).

Therefore, there is a need for the development of new immunotherapies targeting all actors of immunosuppression. There is also a need for efficient therapies, which would be able to reactivate the immunogenicity of tumors, and/or which would restore the patient's immune system.

The present invention aims to solve these needs: it relates to compounds, which are P2RX7 modulators, and which could be used to treat both chronic inflammatory diseases and cancer.

Surprisingly, the inventors have discovered that said compounds potentiate P2RX7 in presence of extracellular ATP, and are able to restore functional anti-tumor T cell responses. Besides, the inventors further discovered that said compounds act both directly on tumor cells by increasing tumor immunogenicity, as well as on tumor microenvironment by decreasing infiltration of immunosuppressive cells.

Interestingly, the inventors noticed that said compounds are also efficient for reducing clinical signs of inflammation in a murine model of colonic inflammation.

Thus, unexpectedly, said molecules may be able to treat both inflammatory diseases and cancer.

The present invention thus relates to a compound chosen from compounds of formula (I), their enantiomers and their pharmaceutically acceptable salts:

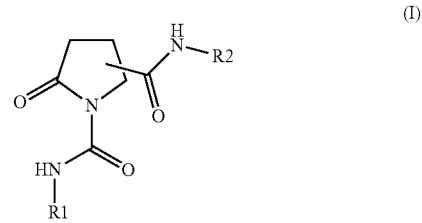

(I)

in which:
R1 represents a C1-C14 alkyl, a cycloalkyl group, an aryl group, an aralkyl group or a heteroaryl group, wherein said aryl, aralkyl or heteroaryl group is not substituted or substituted by at least one group chosen from:

halogen atoms;

C1-C6 alkoxy radicals;

C1-C6 alkyl radicals; and

C1-C6 halogenoalkyl radicals, and R2 represents an aryl group, an aralkyl group or a cycloalkyl group, wherein said aryl group or said aralkyl group is not substituted or substituted by at least one group chosen from halogen atoms.

Preferably, the compound of the invention is different from the following compound:

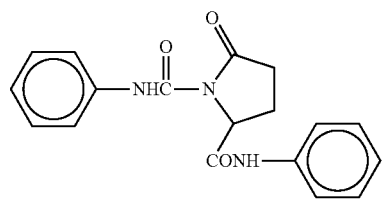

Preferably, the compound of the invention (of formula (I) or (II)) is such that R1 and R2 do not each simultaneously represent a non-substituted phenyl.

Preferably, the compound of the invention (of formula (I) or (II)) is such that R1 and R2 do not each simultaneously represent the following heteroaryl group:

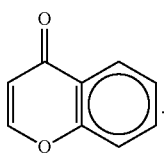

Said heteroayl group is a chromone group.

Preferably the compound of the invention is chosen from compounds of formula (I'), their enantiomers and their pharmaceutically acceptable salts:

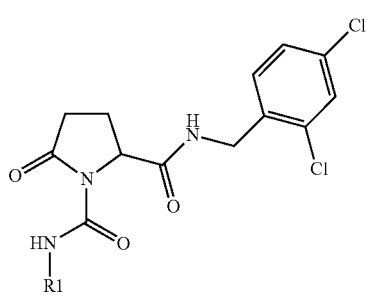

(I')

in which R1 represents a C1-C14 alkyl, a cycloalkyl group, an aryl group, an aralkyl group or a heteroaryl group, wherein said aryl, aralkyl or heteroaryl group is not substituted or substituted by at least one group chosen from:
halogen atoms;
C1-C6 alkoxy radicals;
C1-C6 alkyl radicals; and
C1-C6 halogenoalkyl radicals.

Preferably, the compounds of formula (I) are the enantiomers (S); the enantiomers (S) have the following formula (II):

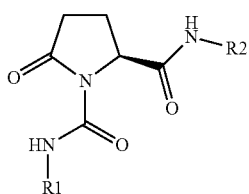

(II)

in which R1 and R2 are as defined above.

More preferably, the compounds of the invention have the following formula (II'):

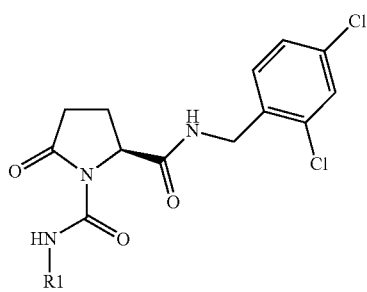

(II')

in which R1 is as defined above.

By "pharmaceutically acceptable salts", it is meant any salt prepared using an inorganic acid such as hydrochloric acid, sulfuric acid, phosphoric acid or the like, or an organic acid such as acetic acid, citric acid, maleic acid, succinic acid, tartaric acid, lactic acid, malic acid, oxalic acid, fumaric acid, methanesulfonic acid or the like.

The halogen atom is preferably chosen from F, Br, I and Cl, more preferably Cl.

By "C1-C14 alkyl", it is meant a linear hydrocarbon group comprising from 1 to 14 carbon atoms, in particular from 1 to 12 carbon atoms, or a branched hydrocarbon group comprising from 3 to 6 carbon atoms. Examples of C1-C14 alkyl groups include methyl, ethyl, n-propyl, isopropyl, n-butyl, isobutyl, tert-butyl, n-pentyl, isopentyl, n-hexyl, and dodecyl groups, and preferably methyl, n-butyl, n-pentyl, n-hexyl, n-dodecyl, isopropyl or tert-butyl.

Similarly, by "C1-C6 alkyl", it is meant a linear hydrocarbon group comprising from 1 to 6 carbon atoms or a branched hydrocarbon group comprising from 3 to 6 carbon atoms. Examples of C1-C6 alkyl groups include methyl, ethyl, n-propyl, isopropyl, n-butyl, isobutyl, tert-butyl, n-pentyl, isopentyl and n-hexyl, and preferably methyl, n-butyl, n-pentyl, n-hexyl, isopropyl or tert-butyl.

By "C1-C6 alkoxy", it is meant an —O-alkyl group wherein the alkyl moiety is a C1-C6 alkyl. Preferably the C1-C6 alkoxy is methoxy.

By "C1-C6 halogenoalkyl", it is meant a C1-C6 alkyl, which is substituted on at least one of its hydrogen atoms by one or more halogen atoms. Preferably the C1-C6 halogenoalkyl is trifluoromethyl.

By "cycloalkyl", it is meant a cyclic saturated hydrocarbon group comprising from 1 to 12 carbon atoms. Preferably the cycloalkyl is chosen from cyclohexylmethyl, adamantyl and cyclohexyl, By "aryl", it is meant a monocyclic or polycyclic aromatic hydrocarbon group, which may be optionally substituted. Preferably, the aryl group is a phenyl. It may also be a biphenyl. The aryl may be not substituted, or substituted by at least one halogen atom, one C1-C6 alkoxy radical, and/or one C1-C6 halogenoalkyl radical.

Preferably the aryl radical is 2-chlorophenyl, 4-chlorophenyl, 2-bromophenyl, 2-iodophenyl, 2,4-dichlorophenyl, 3,4-dichlorophenyl, 2,4-dimethoxyphenyl, 3-trifluoromethylphenyl, 3,5-bis(trifluoromethyl)phenyl or 2,4,6-trimethylphenyl.

By "aralkyl", it is meant an aryl group linked to the remaining part of formula (I) by an alkyl group. The aralkyl may be not substituted, or substituted by at least one halogen atom, one C1-C6 alkoxy radical, one C1-C6 alkyl radical or one C1-C6 halogenoalkyl radical. Preferably the aralkyl is benzyl or phenethyl, substituted or not substituted.

Preferably the aralkyl is chosen from benzyl, 2-chlorobenzyl, 2,4-dichlorobenzyl, 3,4-dichlorobenzyl and 2,4-dichlorophenethyl.

By "heteroaryl", it is meant an aryl group in which at least one carbon atom of the aromatic ring is substituted by a heteroatom, and which may be optionally substituted. The heteroatom may be nitrogen, oxygen, phosphorus or sulfur. Preferably the heteroatom is nitrogen. Examples of heteroaryl groups include pyridine, pyrrole, thiophene, furane, pyrimidine, pyrazine, triazine, imidazole, thiazole, oxazole, and isoxazole groups.

Preferably, the heteroaryl group is a pyridine group such as 2- or 3-pyridino. The heteroaryl may be not substituted, or substituted by at least one halogen atom, one C1-C6 alkoxy radical, and/or one C1-C6 halogenoalkyl radical.

Preferably the heteroaryl radical is 6-chloropyridin-3-yl or thiophen-2-yl.

More preferably, the compound of the invention is chosen from the following compounds (i.e. all enantiomers (S)) and their pharmaceutically acceptable salts:

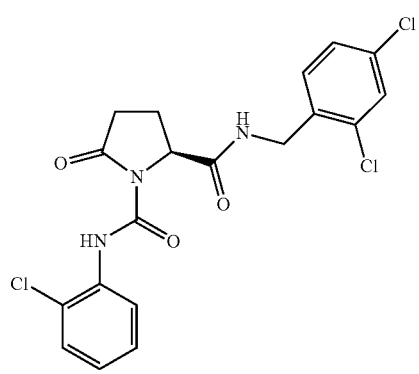

(this compound is called HEI 2314 in the examples of present invention)

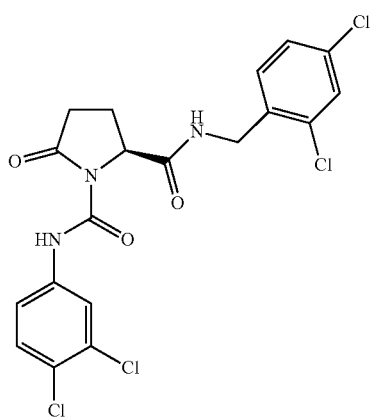

(this compound is called HEI 2338 in the examples of present invention)

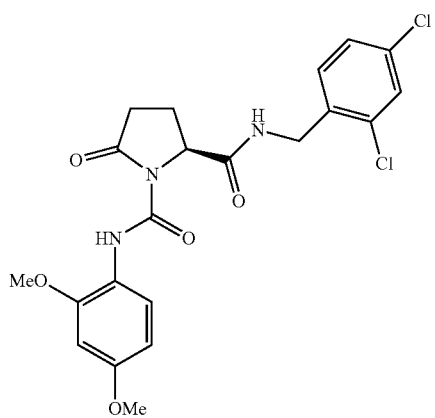

(this compound is called HEI 2333 in the examples of present invention)

-continued

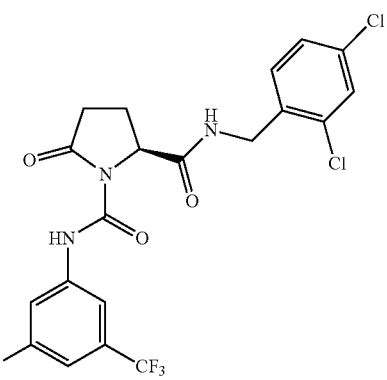

(this compound is called HEI 2336 in the examples of present invention)

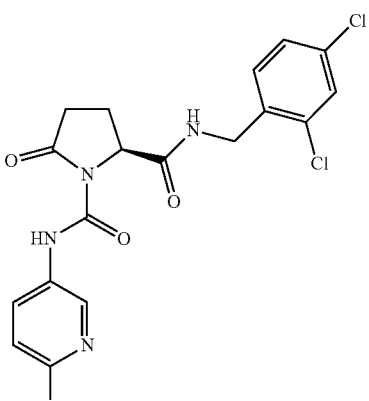

(this compound is called HEI 3090 in the examples of present invention)

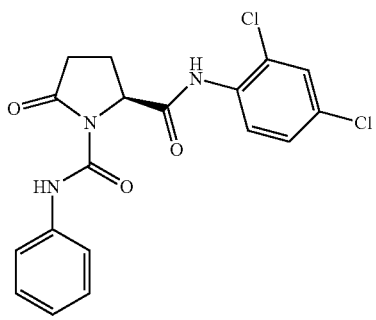

(this compound is called HEI 2347 in the examples of present invention)

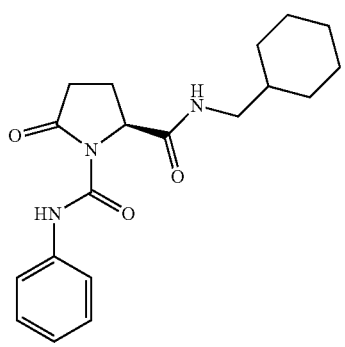

(this compound is called HEI 2346 in the examples of present invention)

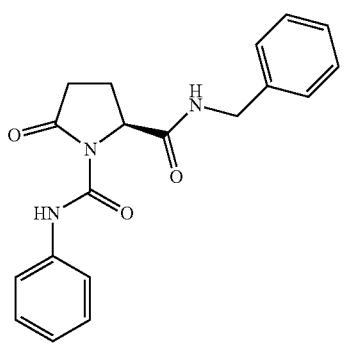

(this compound is called HEI 2269 in the examples of present invention)

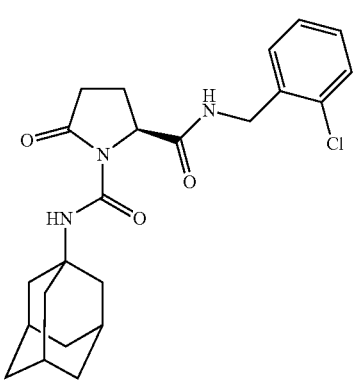

(this compound is called HEI 2298 in the examples of present invention)

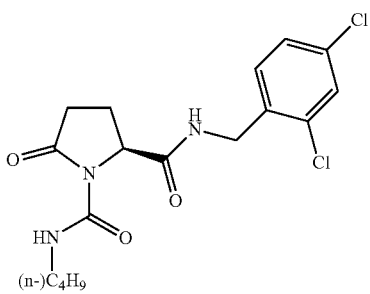

(this compound is called HEI 2535 in the examples of present invention)

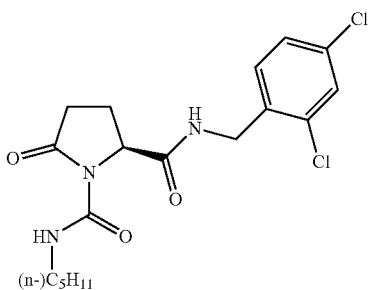

(this compound is called HEI 2541 in the examples of present invention)

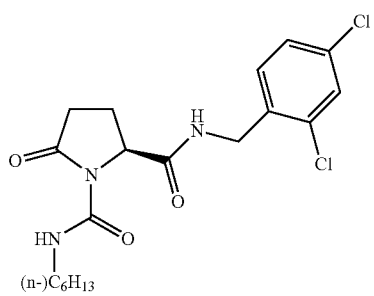

(this compound is called HEI 2534 in the examples of present invention)

(this compound is called HEI 2542 in the examples of present invention)

(this compound is called HEI 2537 in the examples of present invention)

(this compound is called HEI 2538 in the examples of present invention)

-continued

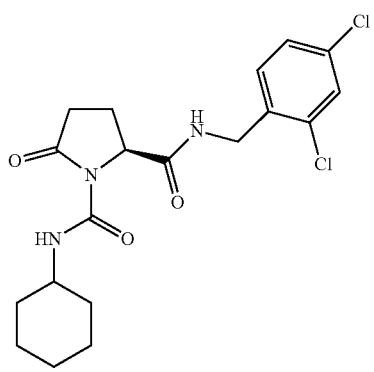

(this compound is called HEI 2315 in the examples of present invention)

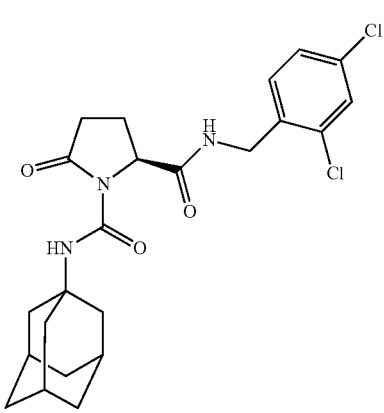

(this compound is called HEI 2329 in the examples of present invention)

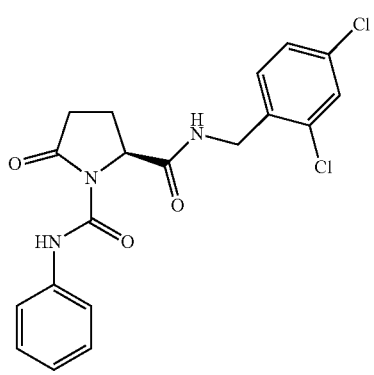

(this compound is called HEI 2339 in the examples of present invention)

-continued

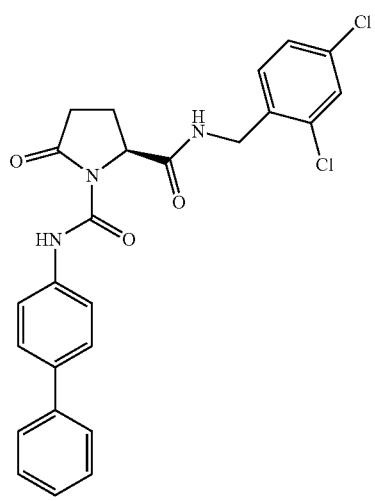

(this compound is called HEI 2761 in the examples of present invention)

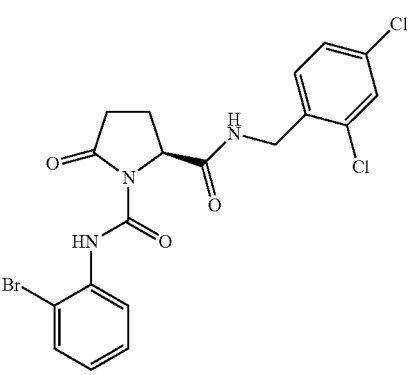

(this compound is called HEI 2760 in the examples of present invention)

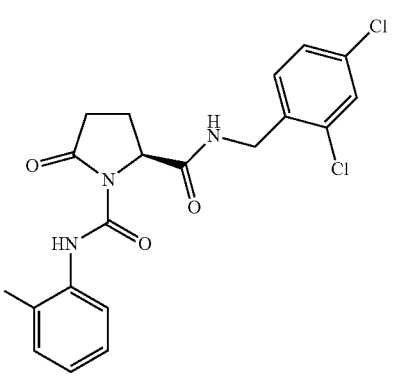

(this compound is called HEI 2759 in the examples of present invention)

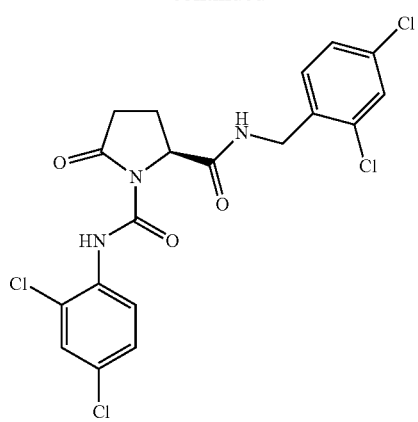

(this compound is called HEI 2331 in the examples of present invention)

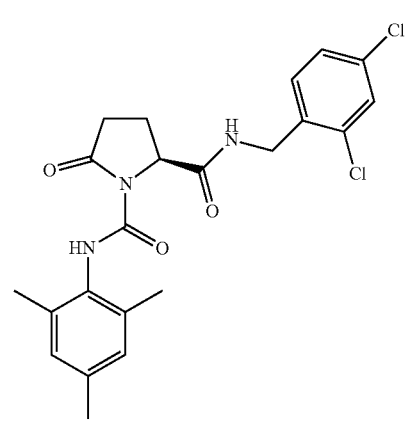

(this compound is called HEI 2338 in the examples of present invention)

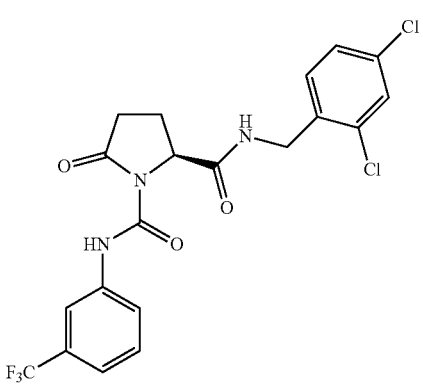

(this compound is called HEI 2337 in the examples of present invention)

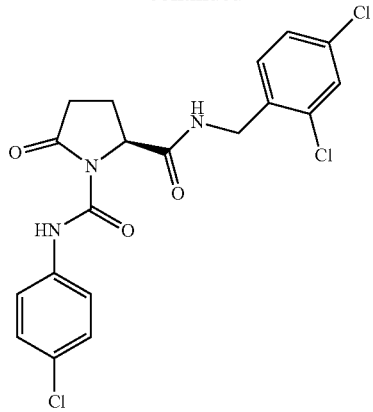

(this compound is called HEI 2278 in the examples of present invention)

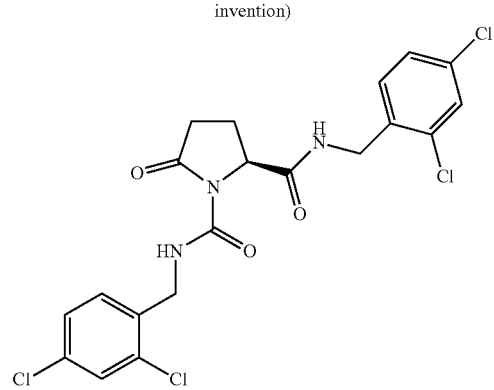

(this compound is called HEI 2817 in the examples of present invention)

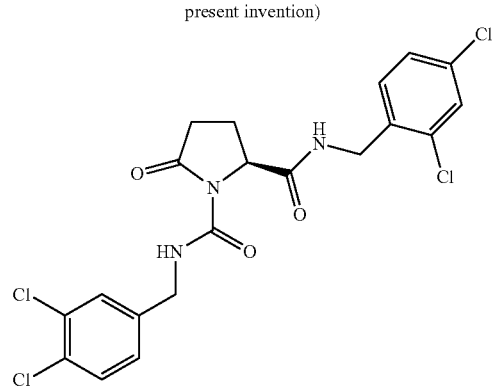

(this compound is called HEI 2820 in the examples of present invention)

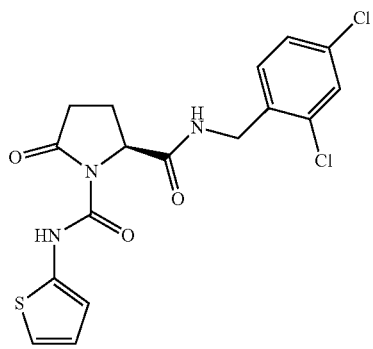

(this compound is called HEI 2548 in the examples of present invention)

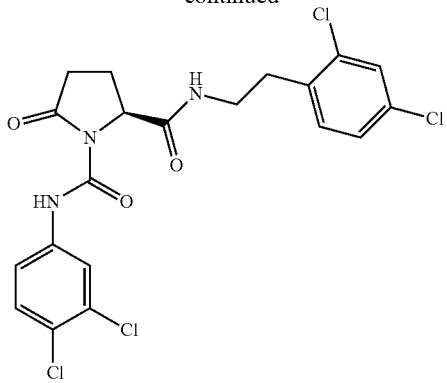

(this compound is called HEI 2773 in the examples of present invention)

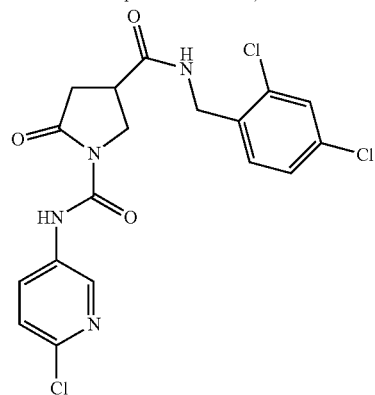

(this compound is called HEI 3127 in the examples of present invention)

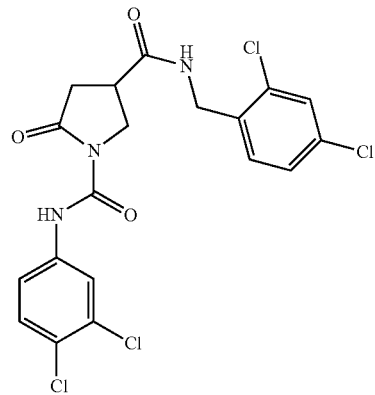

(this compound is called HEI 3204 in the examples of present invention)

As shown in the examples, the compounds of the invention are P2RX7 modulators. They potentiate the action of P2RX7, in the presence of ATP.

Thus, the present invention further relates to the use of a P2RX7 modulator, preferably a P2RX7 compound which potentiates the action of P2RX7 in the presence of ATP, for preventing and/or treating an inflammatory disease and/or a cancer.

By "P2RX7 modulator", it is meant a compound which is able, in the presence of ATP, to induce cell death via large pore opening. By "ATP", it is meant ATP (adenosine triphosphate) per se, but also its derivatives, particularly its benzophenone derivatives such as BzATP (3'-O-(4-benzoyl)benzoyl ATP). Preferably, the P2RX7 modulator is able to increase P2RX7 channel activity (i.e. entry of $Ca^{2+}$ and/or dyes such as Topro3) after short stimulation (such as from 5 to 15 minutes) and to induce cell death via large pore opening at longer stimulation (such as 1 hr). The test which may be used in order to determine whether a given compound is a P2RX7 modulator is described in FIGS. 2, 14 and 15 and in example 2, study 2. Said test is briefly summarized as follows:

Culture cells, which do not express any of the P2X receptors, are transfected with an expression vector coding for mP2rx7 gene. The opening of large pore is assayed with a probe adequate for measuring cell death (such as Topro3 from Invitrogen). In each experiment, cells are treated with BzATP (3'-O-(4-benzoyl)benzoyl ATP), or non-treated, in presence of the tested compound. When indicated, the probe adequate for measuring cell death (such as Topro3) is added.

Fluorescence is assayed by flow cytometry.

Each compound is tested in absence or presence of BzATP.

The tested compound is a P2RX7 modulator if it significantly increases the opening of large pore (thus cell death) in the presence of BzATP, as compared to BzATP alone, and as compared to the tested compound alone.

For example, the compounds of formula (I) (especially of formula (I')) are P2RX7 modulators because they potentiate the effect of P2RX7 on large pore opening in the presence of ATP, thereby causing cell death. Preferably, they potentiate the effect of P2RX7 on $Ca^{2+}$ entry and large pore opening in the presence of ATP.

The human P2RX7 protein is available in Uniprot under accession number Q99572.

Preferably, the compounds of formula (I) according to the invention are agonists of P2RX7. By "agonist" of P2RX7, it is meant a compound which binds to P2RX7 and which activates said P2RX7 to produce the biological response. The potency of an agonist is inversely related to its $EC_{50}$ value. The $EC_{50}$ can be measured for a given agonist by determining the concentration of agonist needed to elicit half of the maximum biological response of the agonist.

Preparation of the Compounds of the Invention

The compounds of formula (I) (and (I'), (II), (II')) according to the present invention may be prepared by a process which is easy to perform. Said process is as follows, and as indicated in Example 1:

A mixture of 5-oxopyrrolidine-2-carboxamide derivative or 5-oxopyrrolidine-3-carboxamide derivative (and especially N-(2,4-dichlorobenzyl)-5-oxopyrrolidine-(2S)-carboxamide in the case of formula (II')) and the corresponding isocyanate in a solvent such as toluene was stirred for some time (for example from 1 to 24 hours) at reflux under nitrogen atmosphere.

The reaction scheme is as follows:

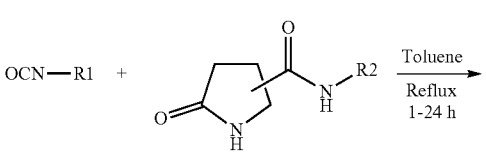

-continued

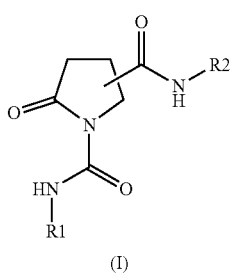

(I)

Preferably the reaction scheme for obtaining compounds of formula (I') is as follows:

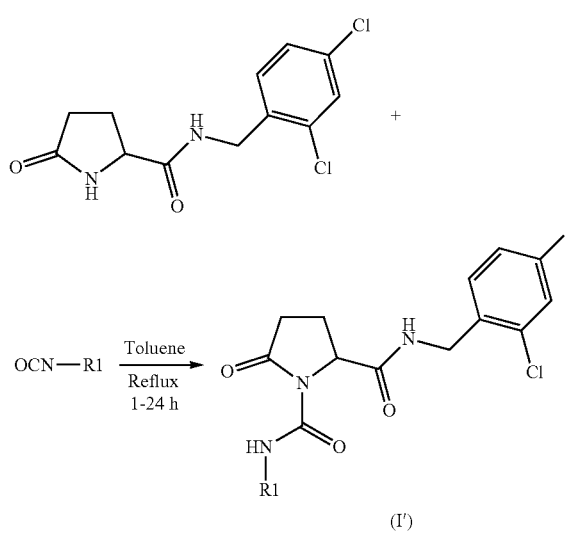

More preferably the reaction scheme for obtaining compounds of formula (II') (i.e. (S) enantiomers) is as follows:

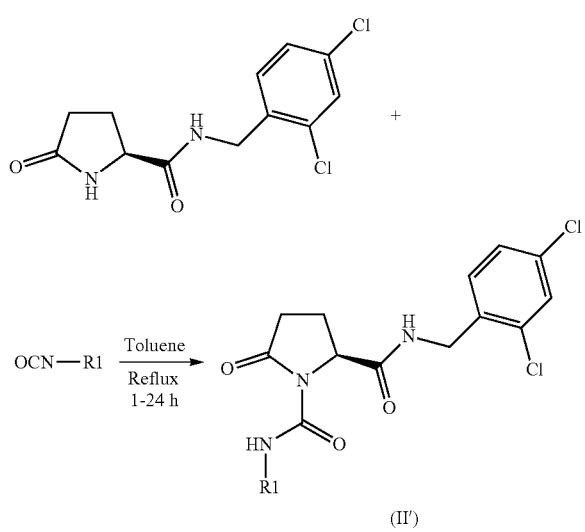

The resulting mixture may then be purified, for example by direct crystallization in methanol (MeOH) or on a silica column, to afford pure compound.

Therapeutic Applications of the Compounds of the Invention

As explained above, and as shown in the examples, the inventors demonstrated that the compounds of the invention are useful in therapy.

Thus, the invention also relates to the use of at least one compound of formula (I), preferably at least one compound of formula (I'), (II) or (II'), its enantiomers or its pharmaceutically acceptable salts, as a medicament.

Particularly, the compounds of formula (I) (preferably the compounds of formula (I'), (II) or (II')), their enantiomers and/or their pharmaceutically acceptable salts may be used for preventing and/or treating an inflammatory disease and/or a cancer.

By "treatment" is meant the curative treatment of inflammatory disease or cancer, respectively. A curative treatment is defined as a treatment that completely treat (cure) or partially treat inflammatory disease or cancer (i.e. induces tumor growth stabilization, retardation or regression), respectively.

The invention also relates to products comprising a) at least one compound chosen from the compounds of formula (I) (preferably compounds of formula (I'), (II) or (II')), their enantiomers and their pharmaceutically acceptable salts, and b) at least one additional therapy, as combination products for a simultaneous, separate or sequential use in the treatment and/or prevention of a cancer.

It also relates to the use of at least one compound of formula (I), preferably at least one compound of formula (I'), (II) or (II'), its enantiomers or its pharmaceutically acceptable salts, for preventing and/or treating a cancer in combination or in association with at least one additional therapy.

It further relates to the use of at least one compound of formula (I), preferably at least one compound of formula (I'), (II) or (II'), its enantiomers or its pharmaceutically acceptable salts, for preventing and/or treating a cancer in a subject treated by at least one additional therapy. The term "subject" refers to any subject and typically designates a patient, in particular a subject undergoing a treatment of cancer such as immunotherapy, chemotherapy and/or radiotherapy.

The invention also relates to at least one compound chosen from the compounds of formula (I) (preferably compounds of formula (I'), (II) or (II')), their enantiomers and their pharmaceutically acceptable salts, for use as an adjuvant cancer therapy. An adjuvant therapy is a therapy for treating cancer that is given besides a primary or initial therapy (here called the "additional therapy"), to maximize its effectiveness.

Said additional therapy b) may be immunotherapy, chemotherapy and/or radiotherapy. Preferably the additional therapy b) is immunotherapy and/or chemotherapy.

By "immunotherapy", it is meant a therapy with is able to induce, enhance or suppress an immune response. Said immunotherapy is preferably chosen from cytokines, chemokines, growth factors, growth inhibitory factors, hormones, soluble receptors, decoy receptors; monoclonal or polyclonal antibodies, mono-specific, bi-specific or multi-specific antibodies, monobodies, polybodies; vaccination; or adoptive specific immunotherapy.

Preferably the immunotherapy is chosen from monoclonal or polyclonal antibodies, mono-specific, bi-specific or multi-specific antibodies, monobodies, polybodies, such as anti-angiogenic agents like Bevacuzimab (mAb, inhibiting VEGF-A, Genentech); IMC-1121B (mAb, inhibiting VEGFR-2, ImClone Systems); CDP-791 (Pegylated DiFab, VEGFR-2, Celltech); 2C3 (mAb, VEGF-A, Peregrine Pharmaceuticals); VEGF-trap (soluble hybrid receptor VEGF-A, PIGF (placenta growth factor) Aventis/Regeneron).

Preferably the immunotherapy is a monoclonal antibody, preferably an anti-checkpoint antibody.

The anti-checkpoint antibodies comprise antibodies directed against an immune checkpoint, which may be chosen from PD1, PDL1, PDL2, CTLA4, BTLA, CD27, CD40, OX40, GITR (also called "Tumor necrosis factor receptor superfamily member 18" or TNFRSF18), CD137 (also called 4-1BB or TNFRS9), CD28, ICOS, IDO (indoleamine 2,3-dioxygenase), B7H3 (also called CD276), KIR2DL2 (also called killer cell immunoglobulin-like receptor 2DL2), NKG2 (a family of the C-type lectin receptors), LAG3 (also called Lymphocyte Activation Gene-3) and CD70. Preferably the anti-checkpoint antibodies are anti-PD1, anti-PDL1, anti-PDL2 or anti-CTLA4 antibodies. Anti-PD1 antibodies include nivolumab and pembrolizumab. Anti-CTLA4 antibodies include ipilimumab and tremelimumab.

Preferably, the invention also relates to products comprising:
a) at least one compound chosen from the compounds of formula (I) (preferably compounds of formula (I'), (II) or (II')), their enantiomers and their pharmaceutically acceptable salts, and
b) at least one additional therapy chosen from anti-checkpoint antibodies, preferably chosen from anti-PD1 antibodies, more preferably chosen from nivolumab and pembrolizumab, as combination products for a simultaneous, separate or sequential use in the treatment and/or prevention of a cancer.

The "chemotherapy" or "chemotherapeutic agent" refers to compounds which are used in the treatment of cancer and that have the functional property of inhibiting a development or progression of aneoplasm in a human, particularly a malignant (cancerous) lesion.

Chemotherapeutic agents have different modes of actions, for example, by influencing either DNA or RNA and interfering with cell cycle replication.

Examples of chemotherapeutic agents that act at the DNA level or on the RNA level are:
- anti-metabolites, such as Azathioprine, Cytarabine, Fludarabine phosphate, Fludarabine, Gemcitabine, cytarabine, Cladribine, capecitabine 6-mercaptopurine, 6-thioguanine, methotrexate, 5-fluoroouracil and hyroxyurea;
- alkylating agents, such as Melphalan, Busulfan, Cisplatin, Carboplatin, Cyclophosphamide, Ifosphamide, Dacarabazine, Fotemustine, Procarbazine, Chlorambucil, Thiotepa, Lomustine, Temozolomide;
- anti-mitotic agents, such as Vinorelbine, Vincristine, Vinblastine, Docetaxel, Paclitaxel;
- topoisomerase inhibitors, such as Doxorubincin, Amsacrine, Irinotecan, Daunorubicin, Epirubicin, Mitomycin, Mitoxantrone, Idarubicin, Teniposide, Etoposide, Topotecan;
- antibiotics, such as actinomycin and bleomycin;
- asparaginase;
- anthracyclines or taxanes.

Other chemotherapeutic agents are tyrosine kinase inhibitors (TKI). Anumber of TKIs are in late and early stage development for treatment of various types of cancer. Examplary TKIs include, but are not limited to: BAY 43-9006 (Sorafenib, Nexavar®) and SU11248 (Sunitinib, Sutent®), Imatinib mesylate (Gleevec®, Novartis); Gefitinib (Iressa®, AstraZeneca); Erlotinib hydrochloride (Tarceva®, Genentech); Vandetanib (Zactima®, AstraZeneca), Tipifarnib (Zarnestra®, Janssen-Cilag); Dasatinib (Sprycel®, Bristol Myers Squibb); Lonafarnib (Sarasar®, Schering Plough); Vatalanib succinate (Novartis, Schering AG); Lapatinib (Tykerb®, GlaxoSmithKline); Nilotinib (Novartis); Lestaurtinib (Cephalon); Pazopanib hydrochloride (GlaxoSmithKline); Axitinib (Pfizer); Canertinib dihydrochloride (Pfizer); Pelitinib (National Cancer Institute, Wyeth); Tandutinib (Millennium); Bosutinib (Wyeth); Semaxanib (Sugen, Taiho); AZD-2171 (AstraZeneca); VX-680 (Merck, Vertex); EXEL-0999 (Exelixis); ARRY-142886 (ArrayBioPharma, AstraZeneca); PD-0325901 (Pfizer); AMG-706 (Amgen); BIBF-1120 (Boehringer Ingelheim); SU-6668 (Taiho); CP-547632 (OSI); (AEE-788 (Novartis); BMS-582664 (Bristol-Myers Squibb); JNK-401 (Celgene); R-788 (Rigel); AZD-1152 HQPA (AstraZeneca); NM-3 (Genzyme Oncology); CP-868596 (Pfizer); BMS-599626 (Bristol-Myers Squibb); PTC-299 (PTC Therapeutics); ABT-869 (Abbott); EXEL-2880 (Exelixis); AG-024322 (Pfizer); XL-820 (Exelixis); OSI-930 (OSI); XL-184 (Exelixis); KRN-951 (Kirin Brewery); CP-724714 (OSI); E-7080 (Eisai); HKI-272 (Wyeth); CHIR-258 (Chiron); ZK-304709 (Schering AG); EXEL-7647 (Exelixis); BAY-57-9352 (Bayer); BIBW-2992 (Boehringer Ingelheim); AV-412 (AVEO); YN-968D1 (Advenchen Laboratories); Staurosporin, Midostaurin (PKC412, Novartis); Perifosine (AEterna Zentaris, Keryx, National Cancer Institute); AG-024322 (Pfizer); AZD-1152 (AstraZeneca); ON-01910Na (Onconova); and AZD-0530 (AstraZeneca).

The inflammatory disease is preferably a chronic inflammatory disease, and may be chosen from rheumatoid arthritis, Crohn's disease, inflammatory bowel disease (IBD), osteoartrosis, osteoporosis, dermatitis, psoriasis, asthma, respiratory distress syndrome and chronic obstructive pulmonary disease (COPD).

The cancer is for example selected from a colon cancer, a colorectal cancer, a melanoma, a breast cancer, a thyroid cancer, a prostate cancer, an ovarian cancer, a lung cancer, a pancreatic cancer, a glioma, a cervical cancer, an endometrial cancer, a head and neck cancer, a liver cancer, a renal cancer, a skin cancer, a stomach cancer, a testis cancer, an urothelial cancer or an adrenocortical carcinoma, but also non solid cancers such as lymphoma.

The cancer can be a metastatic cancer or not. The cancer can be susceptible to immunotherapy or not. Preferably, the cancer is a lung cancer, preferably Lewis lung cancer.

Herein described is also a method for preventing and/or treating cancer, comprising administering to a subject in need thereof with an effective amount of at least one compound of formula (I) as defined above, preferably at least one compound of formula (I'), (II) or (II'), its enantiomers or its pharmaceutically acceptable salts.

The term "subject" refers to any subject and typically designates a patient, in particular a subject undergoing a treatment of cancer such as immunotherapy, chemotherapy and/or radiotherapy, or a subject at risk, or suspected to be at risk, of developing a cancer.

Herein described is also a method for preventing and/or treating an inflammatory disease, comprising administering to a subject in need thereof with an effective amount of at least one compound of formula (I) as defined above, preferably at least one compound of formula (I'), (II) or (II'), its enantiomers or its pharmaceutically acceptable salts.

The term "subject" refers to any subject and typically designates a patient, in particular a subject undergoing a treatment of inflammatory disease, or a subject at risk, or suspected to be at risk, of developing an inflammatory disease.

In any case, the subject is preferably a mammal, even more preferably a human being, for example a human being suffering of a cancer or from an inflammatory disease.

The compound of the invention is preferably administered at a therapeutically effective amount or dose. As used herein, "a therapeutically effective amount or dose" refers to an amount of the compound of the invention which prevents, removes, slows down the cancer or inflammatory disease, or reduces or delays one or several symptoms or disorders caused by or associated with said disease in the subject, preferably a human being. The effective amount, and more generally the dosage regimen, of the compound of the invention and pharmaceutical compositions thereof may be determined and adapted by the one skilled in the art. An effective dose can be determined by the use of conventional techniques and by observing results obtained under analogous circumstances. The therapeutically effective dose of the compound of the invention will vary depending on the disease to be treated or prevented, its gravity, the route of administration, any co-therapy involved, the patient's age, weight, general medical condition, medical history, etc.

Typically, the amount of the compound to be administrated to a patient may range from about 0.01 to 500 mg/kg of body weight for a human patient. In a particular embodiment, the pharmaceutical composition according to the invention comprises 0.01 mg/kg to 300 mg/kg of the compound of the invention, preferably from 0.01 mg/kg to 3 mg/kg, for instance from 25 to 300 mg/kg.

In a particular aspect, the compounds of the invention can be administered to the subject by parenteral route, topical route, oral route or intravenous injection. The compound or the nanoparticle of the invention may be administered to the subject daily (for example 1, 2, 3, 4, 5, 6 or 7 times a day) during several consecutive days, for example during 2 to 10 consecutive days, preferably from 3 to 6 consecutive days. Said treatment may be repeated during 1, 2, 3, 4, 5, 6 or 7 weeks, or every two or three weeks or every one, two or three months. Alternatively, several treatment cycles can be performed, optionally with a break period between two treatment cycles, for instance of 1, 2, 3, 4 or 5 weeks. The compound or the nanoparticle of the invention can for example be administered as a single dose once a week, once every two weeks, or once a month. The treatment may be repeated one or several times per year.

Doses are administered at appropriate intervals which can be determined by the skilled person. The amount chosen will depend on multiple factors, including the route of administration, duration of administration, time of administration, the elimination rate of the selected compound of formula (I), or of the various products used in combination with said compound, the age, weight and physical condition of the patient and his/her medical history, and any other information known in medicine.

The administration route can be oral, topical or parenteral, typically rectal, sublingual, intranasal, intra-peritoneal (IP), intra-venous (IV), intra-arterial (IA), intra-muscular (IM), intra-cerebellar, intrathecal, intratumoral and/or intradermal. The pharmaceutical composition is adapted for one or several of the above-mentioned routes. The pharmaceutical composition is preferably administered by injection or by intravenous infusion of suitable sterile solutions, or in the form of liquid or solid doses via the alimentary canal.

Another object of the invention is a composition comprising, in a pharmaceutically acceptable carrier, at least one compound of formula (I), preferably at least one compound of formula (I'), (II) or (II'), its enantiomers or its pharmaceutically acceptable salts.

The carrier must be "acceptable" in the sense of being compatible with the other ingredients of the formulations and not deleterious to the recipient thereof.

The pharmaceutical composition can be formulated as solutions in pharmaceutically compatible solvents or as gels, oils, emulsions, suspensions, or dispersions in suitable pharmaceutical solvents or vehicles, or as pills, tablets, capsules, powders, suppositories, etc. that contain solid vehicles in a way known in the art, possibly through dosage forms or devices providing sustained and/or delayed release. For this type of formulation, an agent such as cellulose, lipids, carbonates or starches are used advantageously.

Agents or vehicles that can be used in the formulations (liquid and/or injectable and/or solid) are excipients or inert vehicles, i.e. pharmaceutically inactive and non-toxic vehicles. Mention may be made, for example, of saline, physiological, isotonic and/or buffered solutions, compatible with pharmaceutical use and known to those skilled in the art. The compositions may contain one or more agents or vehicles chosen from dispersants, solubilizers, stabilizers, preservatives, etc.

Particular examples are methylcellulose, hydroxymethylcellulose, carboxymethylcellulose, cyclodextrins, polysorbate 80, mannitol, gelatin, lactose, liposomes, vegetable oils or animal, acacia, etc. Preferably, vegetable oils are used.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations suitable for parenteral administration conveniently comprise a sterile oily or aqueous preparation of the active ingredient which is preferably isotonic with the blood of the recipient. Every such formulation can also contain other pharmaceutically compatible and non-toxic auxiliary agents, such as, e.g. stabilizers, antioxidants, binders, dyes, emulsifiers or flavoring substances.

The figures used in the present application are the following and serve as illustrative purposes only:

FIG. 1: HEI2314 and HEI2328 increase large pore opening in presence of ATP in heterologous cell system expressing mouse P2RX7.

Calcium channel activity (Fluo4AM probe) and large pore opening (Topro3 probe) were analysed by FACS on mP2RX7 HEK cells. Cells were non stimulated (NS) or treated with BzATP (500 µM) alone or in the presence of HEI2314, HEI2328, HEI2333 or HEI2336 (used at 50 µM). Each panel showed representative dot plots and red numbers indicated the percentage of positive cells in each sub panel.

Figure 2:
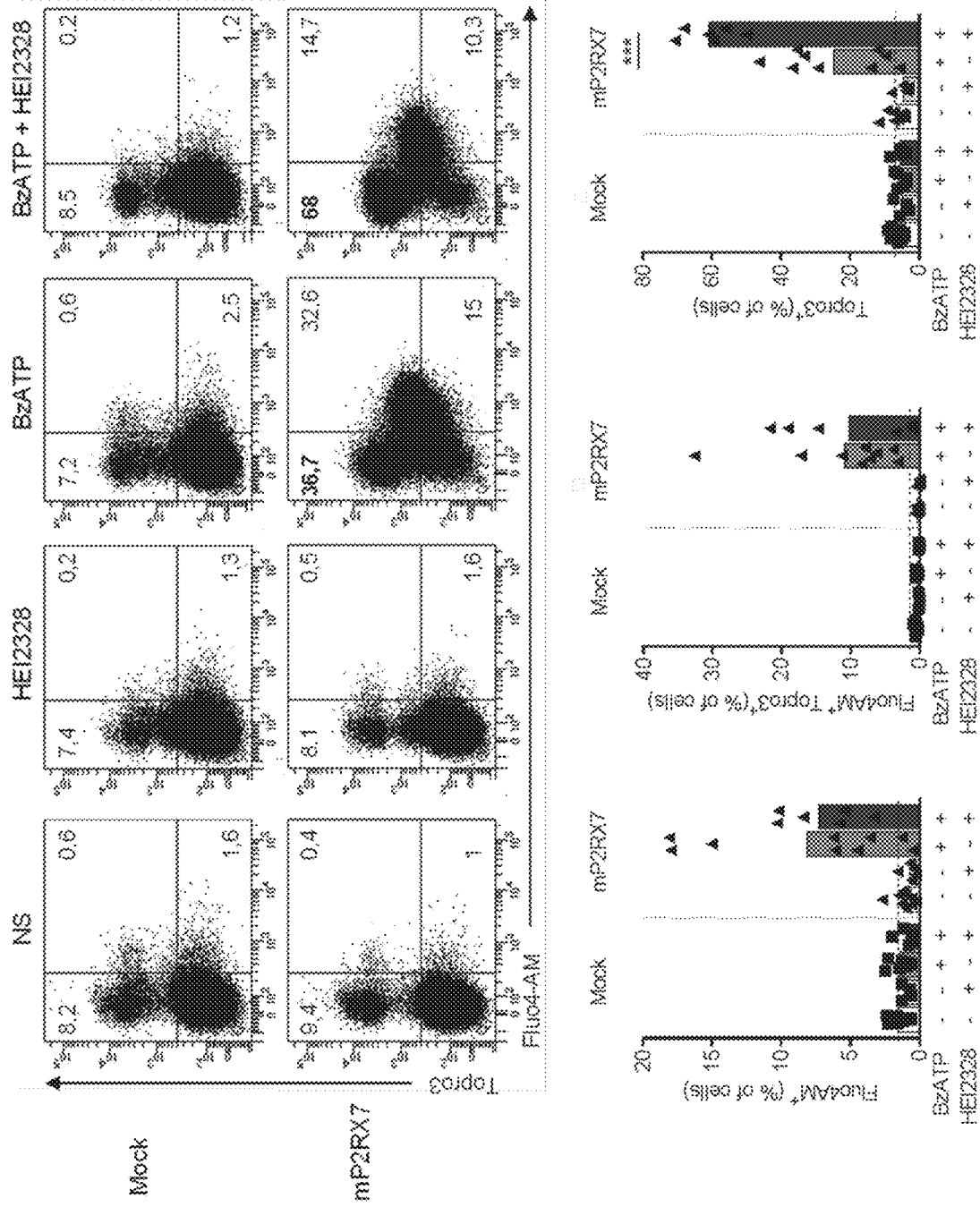

FIG. 2: mP2RX7 and ATP are required to mediate large pore opening in response to HEI2328.

Calcium channel activity (Fluo4AM probe) and large pore opening (Topro3 probe) were analysed by FACS on mock and mP2RX7 HEK cells. Cells were non stimulated (NS) or treated with BzATP (500 µM) alone or in the presence of HEI2328 used at 50 µM. Each panel showed representative dot plots and red numbers indicated the percentage of positive cells in each sub panel. Histograms showed results from 9 independent experiments. ***, $p<0.001$ (Mann-Whitney test).

Figure 3:
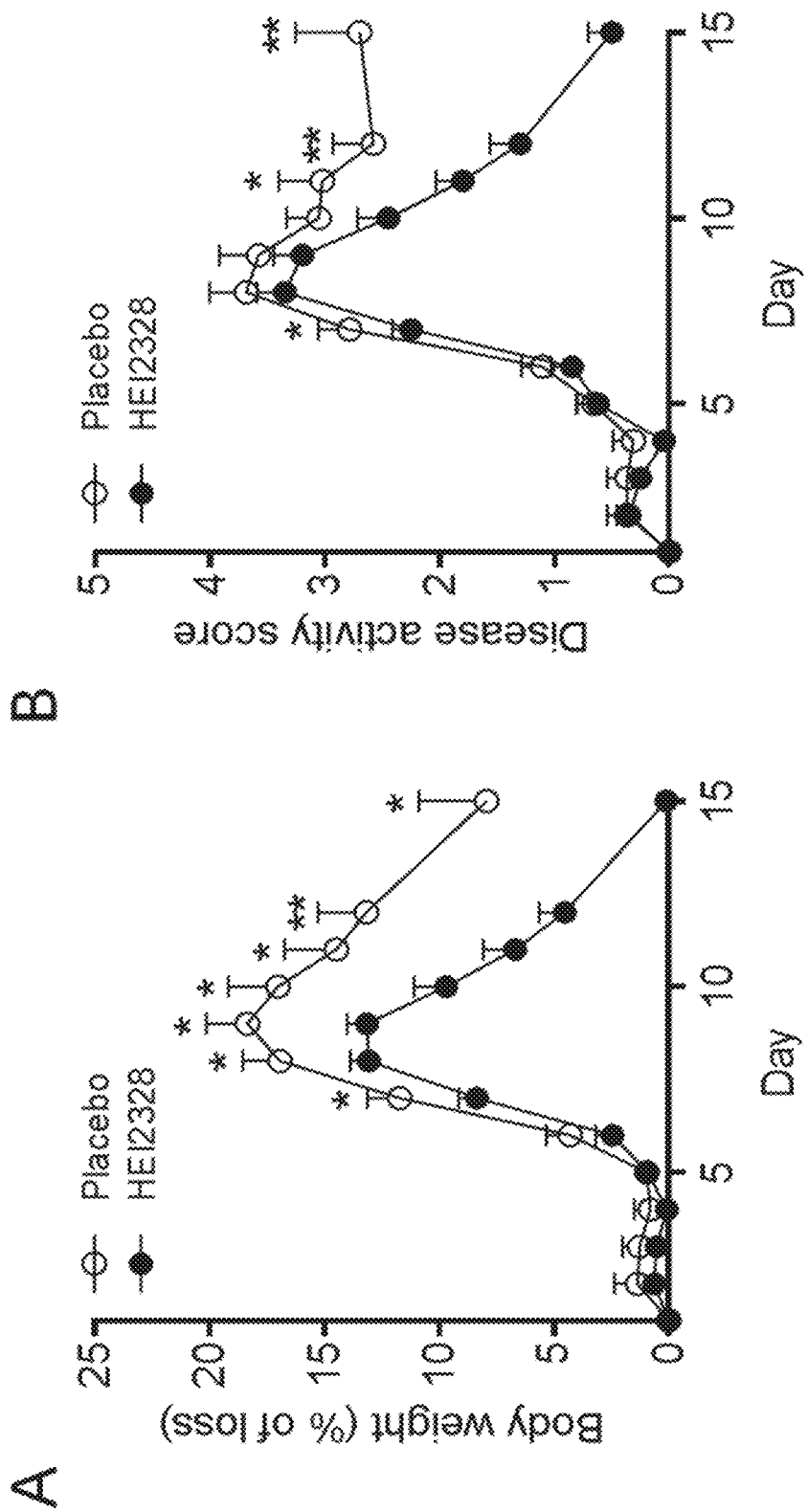

FIG. 3: HEI2328 significantly ameliorates DSS-induced colitis in vivo.

(A) Body weight loss and (B) clinical scores from C57BL/6J treated with 3% DSS during 5 days (J1 to J5), followed by 10 days of normal tap water. The treated group received HEI2328 (ip, 2.3 mg/kg in PBS, 10% DMSO). Data are representative of 2 independent experiments (n=20). Mean±SEM are shown. *, p<0.05; **, p<0.01 (Mann-Whitney test).

Figure 4:
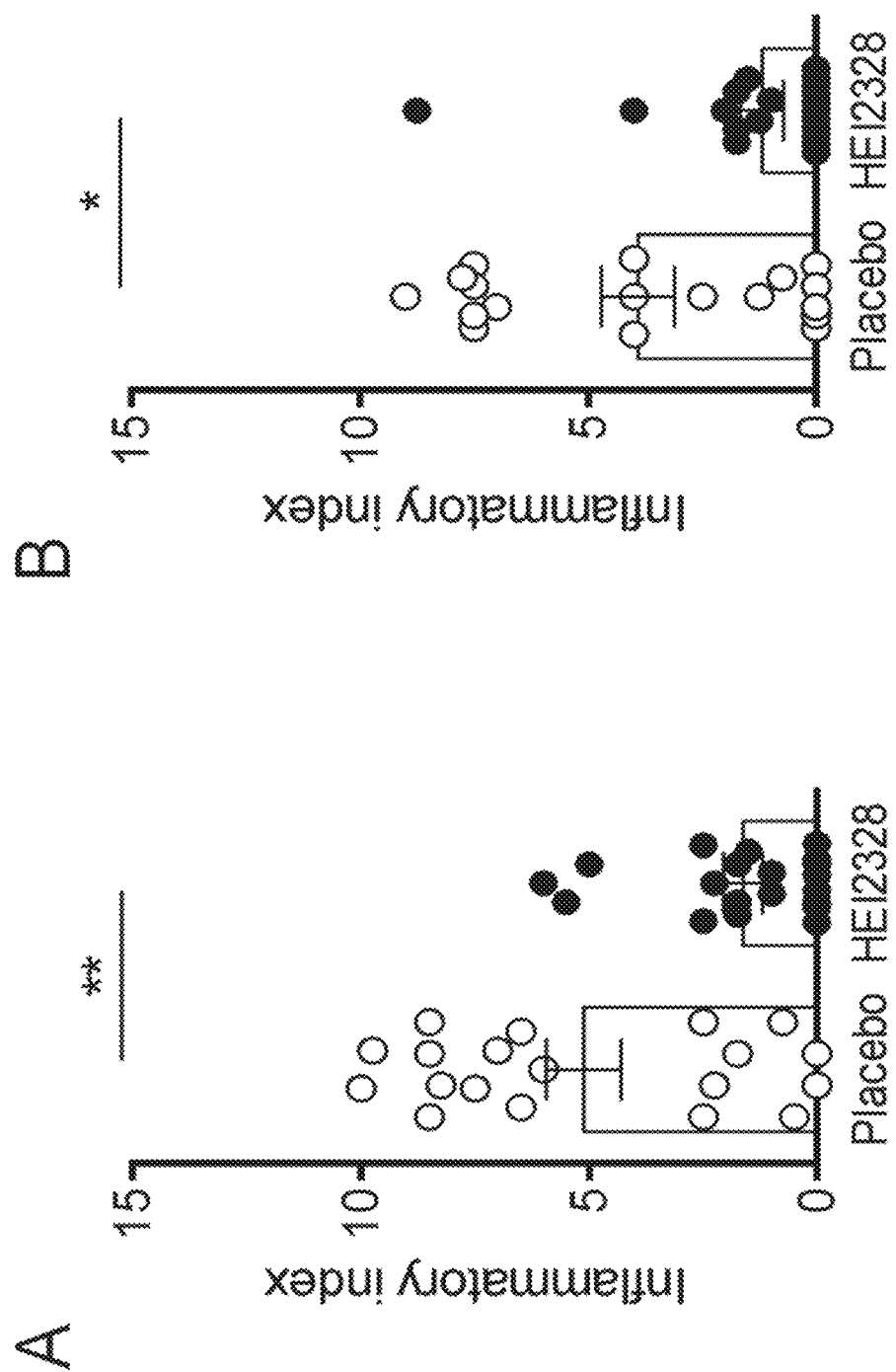

FIG. 4: HEI2328 significantly decreases inflammatory lesions in the colon of DSS-treated mice.

The inflammatory index was scored in a longitudinal (A) and a transversal section of the colon (B). Data are representative of 2 independent experiments (n=20). Mean±SEM are shown. *, p<0.05; **, p<0.01 (Mann-Whitney test).

Figure 5:
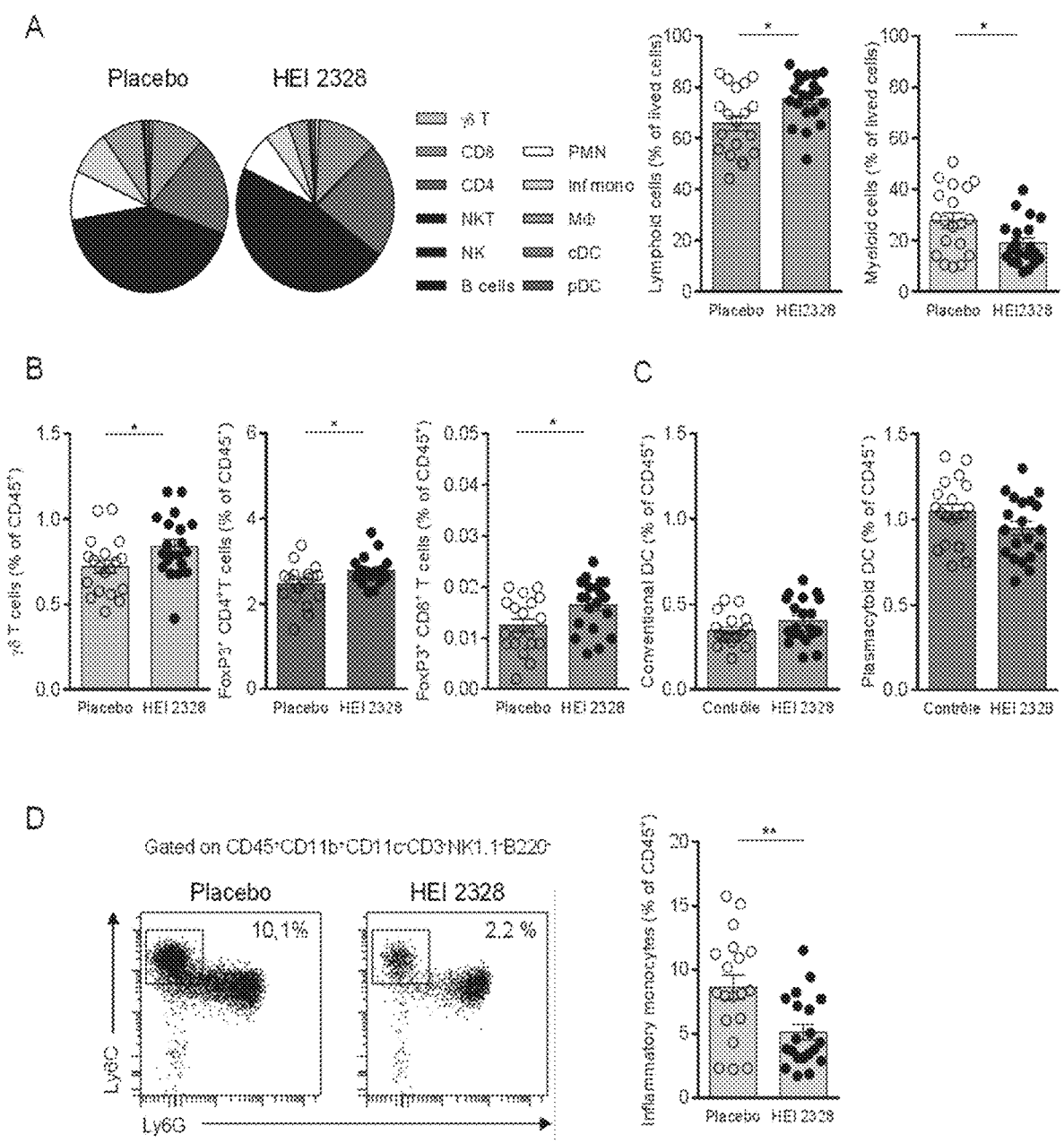

FIG. 5: HEI2328 decreases the proportion of inflammatory monocytes within the spleen.

(A-D) Phenotypic analysis of immune cells in spleen of 20 mice treated with HEI2328 or non treated. Data are representative of 2 independent experiments (n=20). Mean±SEM are shown. *, p<0.05; **, p<0.01 (Mann-Whitney test).

Figure 6:
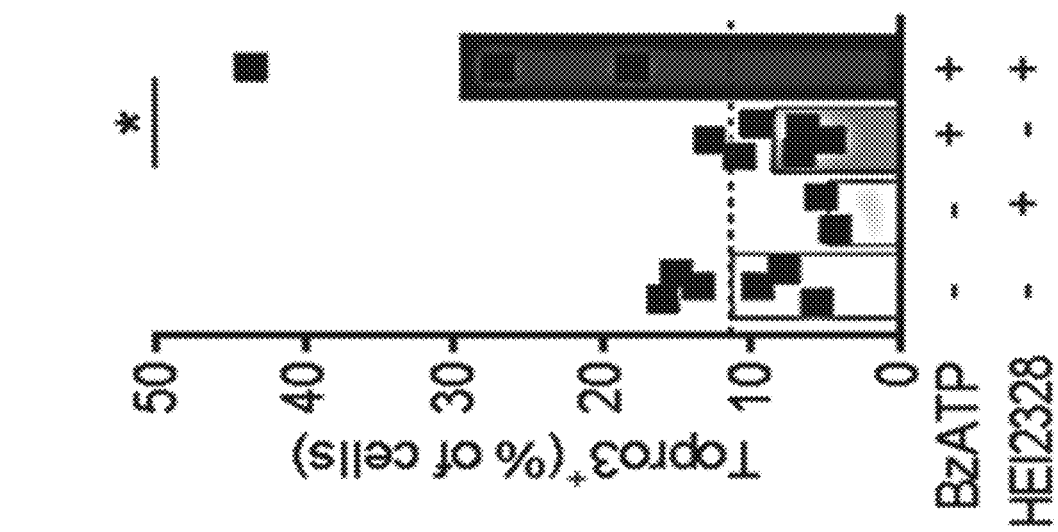
Figure 6:
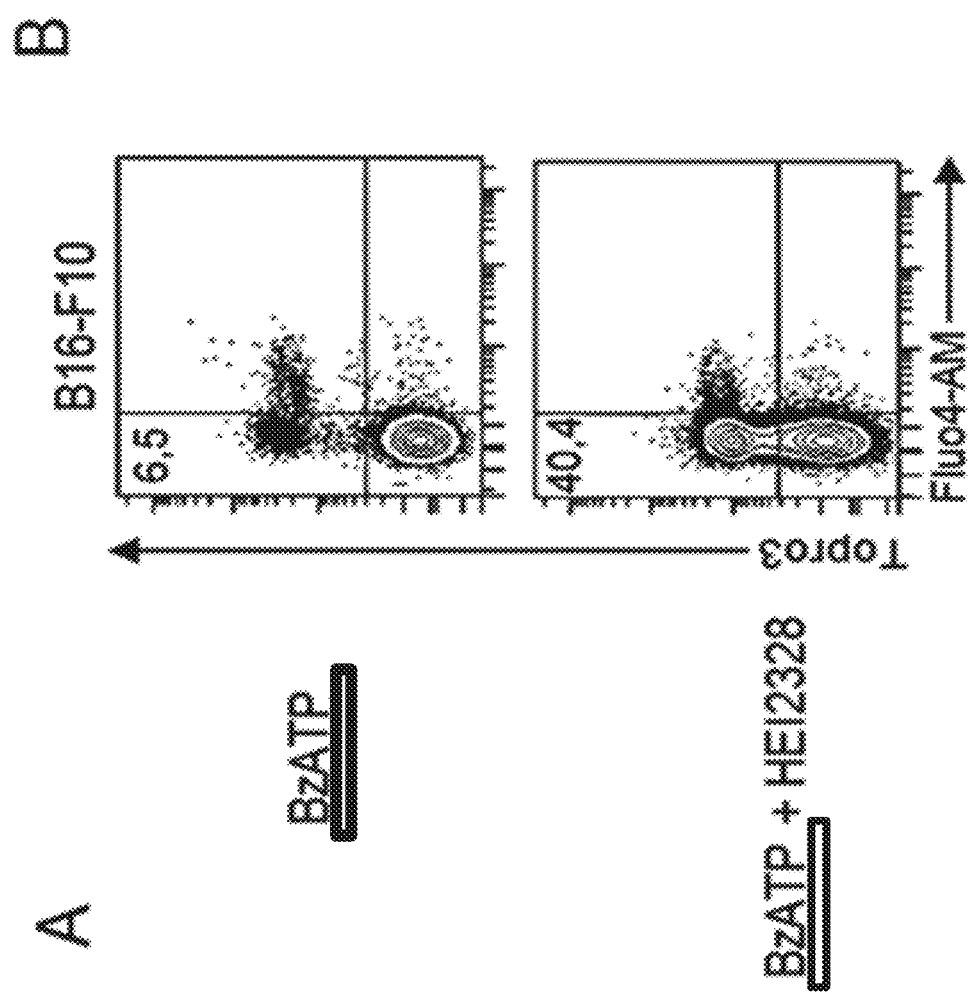

FIG. 6: HEI2328 increases large pore opening in presence of ATP in B16F10 melanoma cell line.

Calcium channel activity (Fluo4AM probe) and large pore opening (Topro3 probe) were analysed by FACS. Unstimulated (NS) or cells treated with HEI2328 (50 μM) alone or with BzATP (500 μM) were analysed. (A) Representative dots plots. Numbers highlighted the percentage of positive cells. (B) Histogram showed results from 3 independent experiments. *, p<0.05 (Mann-Whitney test).

Figure 7:
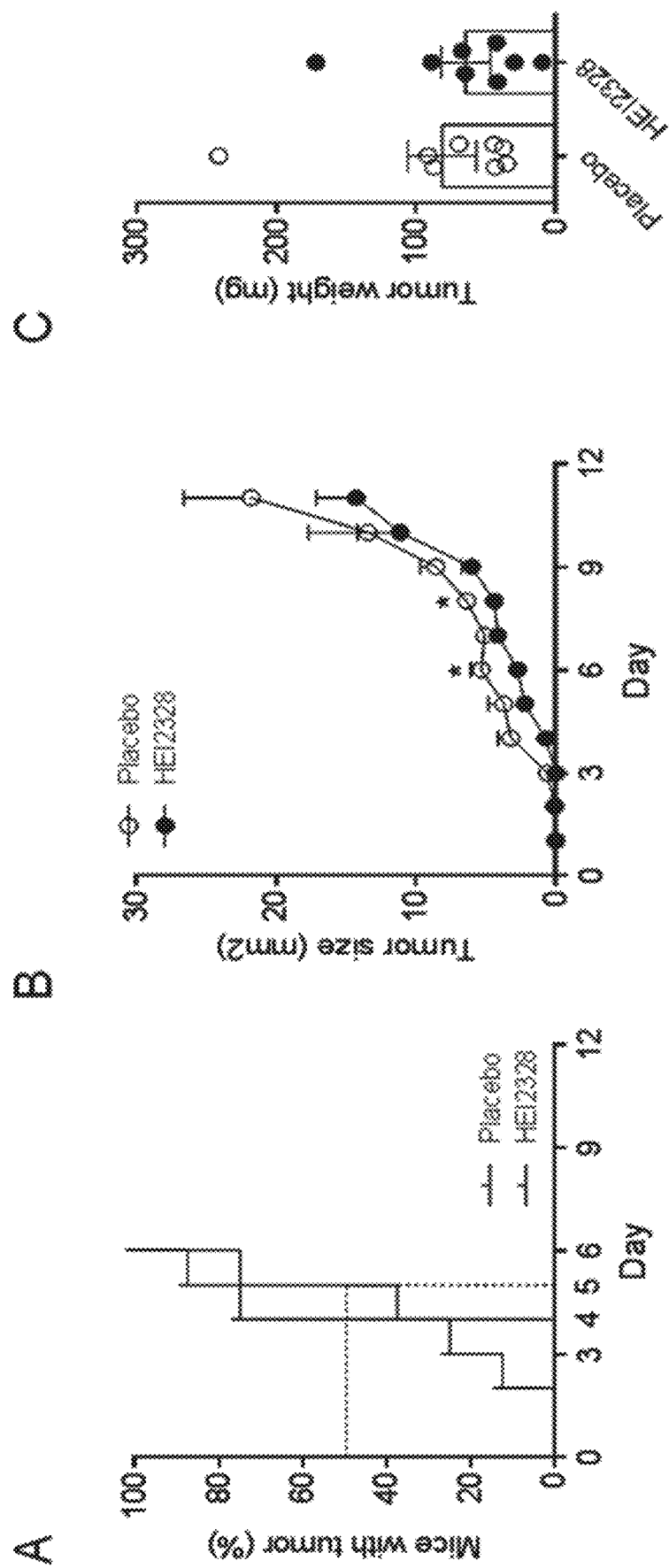

FIG. 7: HEI2328 decreased tumor growth in vivo.

$5 \times 10^5$ B16F10 cells were injected sub cutaneously in the right flank of C57BL/6 mice. Mice received HEI2328 (n=8, ip, 2.3 mg/kg in 10% DMSO/PBS) daily or placebo (n=8, 10% DMSO/PBS). A. incidence of tumor appearance B. Tumor size (mm2) and C. tumor weight at sacrifice day (J12). *, p<0.05 (Mann-Whitney test).

Figure 8:
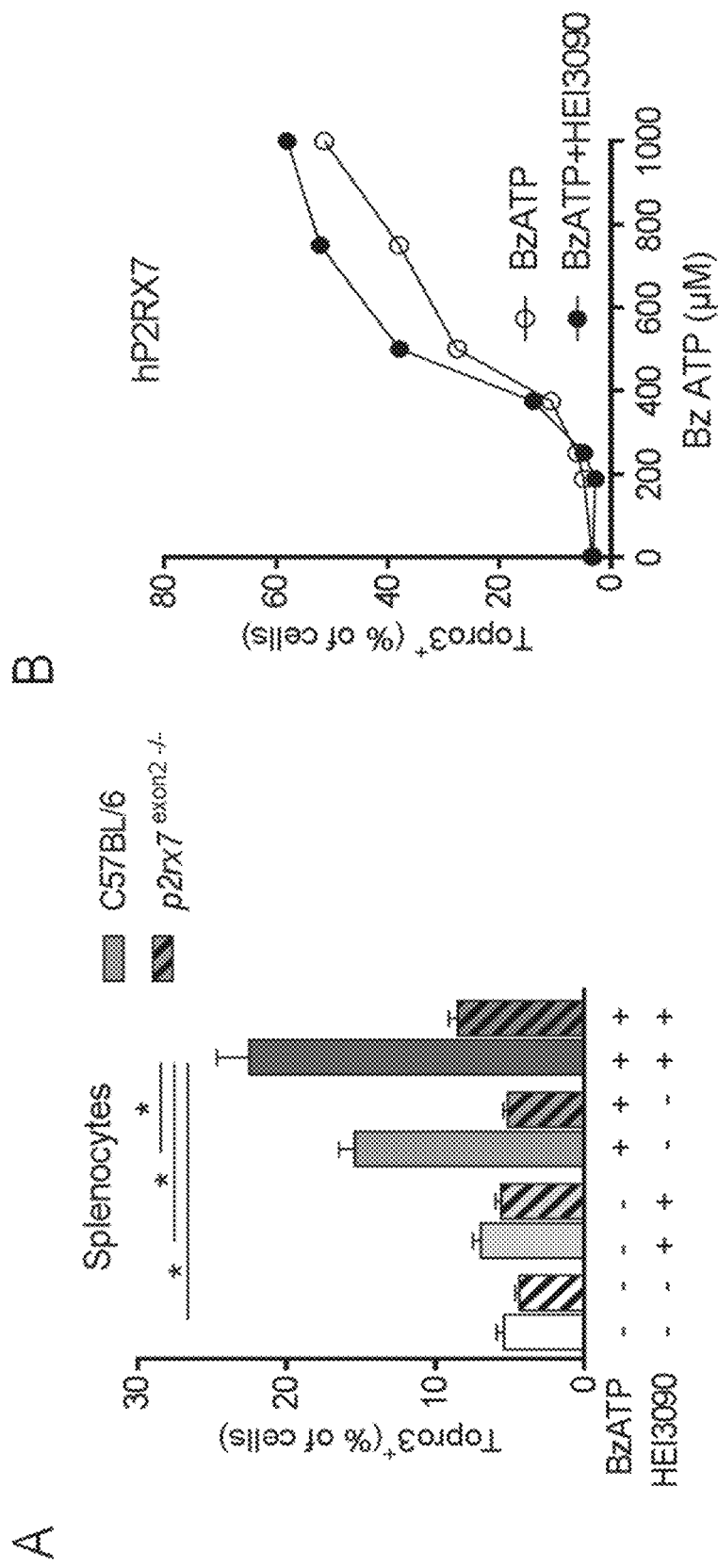

FIG. 8: HEI3090 increased large pore opening in presence of BzATP.

A. Splenocytes from control or $p2rx7^{exon2\ KO}$ mice were isolated and treated with HEI3090 (50 μM) in presence of absence of BzATP (500 μM). B. Large pore opening induced by increasing concentration of BzATP in presence or absence of HEI3090 in human P2RX7 expressing cells.

Figure 9:
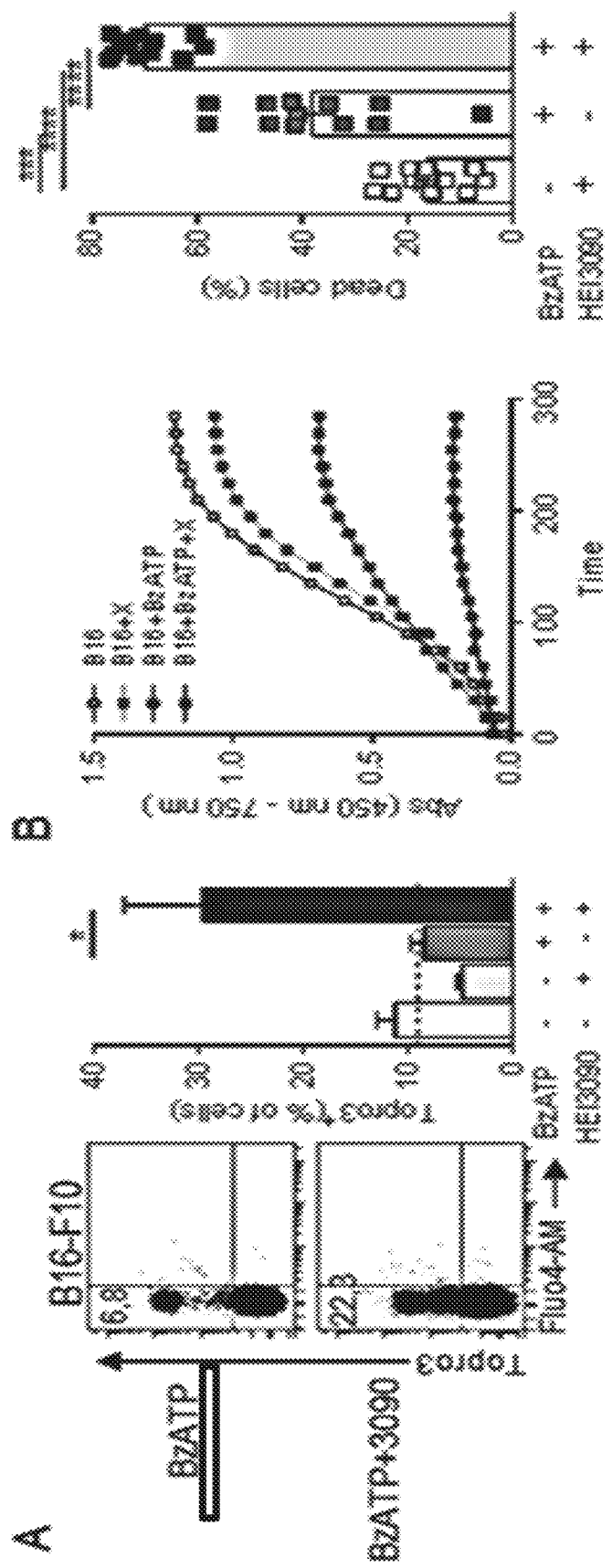

FIG. 9: HEI3090 induced B16F10 cell death in presence of BzATP.

A. Large pore opening. Dot plot of representative experiment. Numbers highlighted the percentage of positive cells. Histogram showed results from 3 independent experiments. *, p<0.05 Mann-Whitney test. B. representative curve of XTT absorbance over the time. Histogram showed the percentage of dead cell. Mean±SEM are shown. *, p<0.001; **, p<0.0001 Mann-Whitney test.

Figure 10:
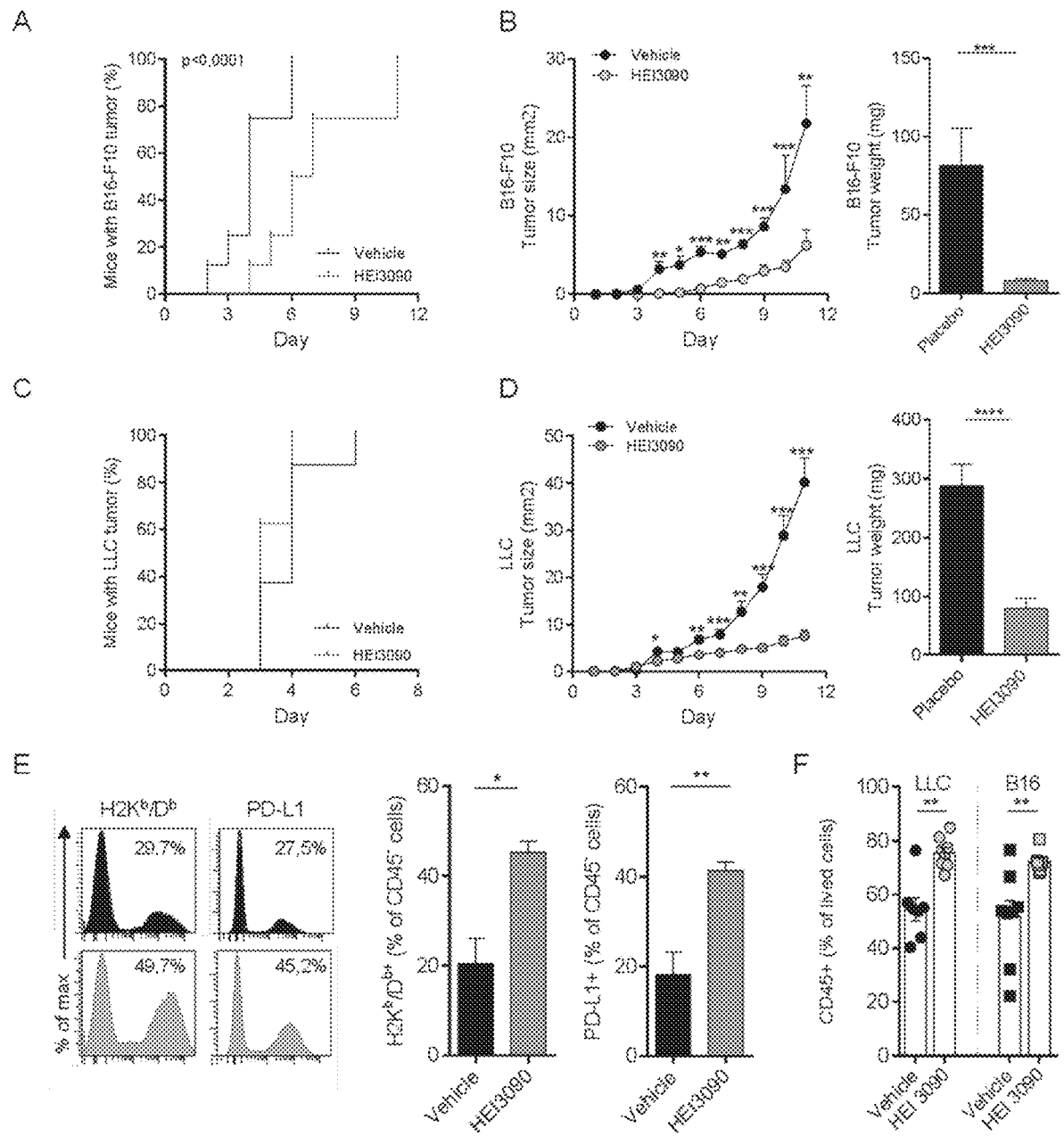

FIG. 10: HEI3090 is a potent tumor suppressor in mice.

$5 \times 10^5$ LLC or $5 \times 10^5$ B16F10 cells were injected sub cutaneously in the right flank of C57BL6 mice. Mice received HEI3090 (ip, 2.5 mg/kg in 10% DMSO/PBS) daily or placebo (10% DMSO/PBS). A,C. incidence of tumor appearance B,D. Tumor size (mm2) and tumor weight at sacrifice day (J12). E. HEI-treated tumors are more immunogenic. Expression of CMH1 ($H2K^b/D^b$) and PD-L1 by LLC (black) and B16F10 (grey) tumors is shown in dot plots. Numbers highlighted the percentage of tumor cells positive for $H2K^b/D^b$ and PD-L1. Histograms showed the mean±SEM. F. CD-45 positive infiltrates is increased in LLC and B16F10 tumors. *, p<0.05; , p<0.01; *, p<0.001 Mann-Whitney test.

Figure 11:
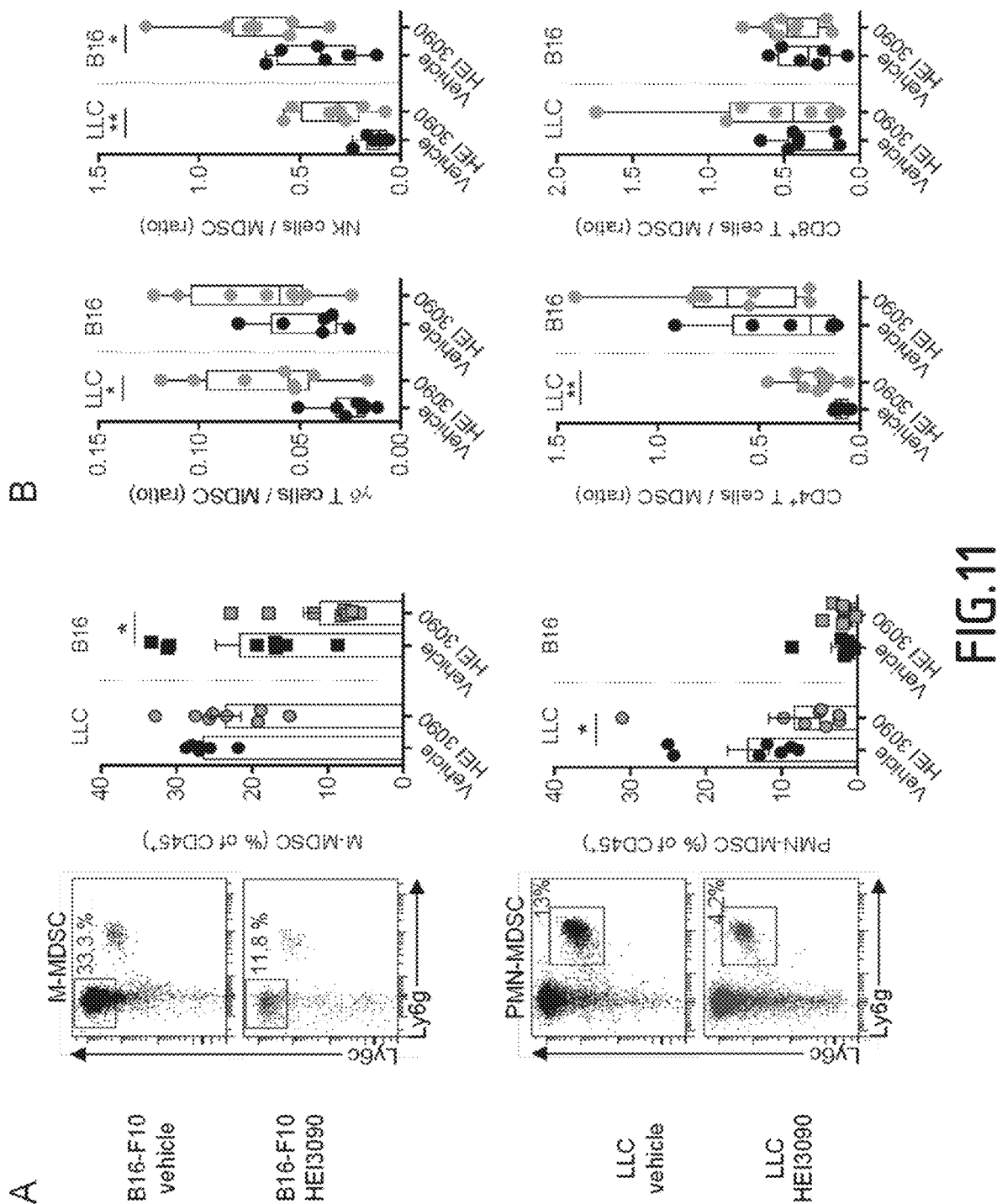

FIG. 11: HEI3090 modified tumor infiltrates toward a less immunosuppressive environment.

$5 \times 10^5$ LLC or $5 \times 10^5$ B16F10 cells were injected sub cutaneously in the right flank of C57BL6 mice. Mice received HEI3090 (ip, 2.5 mg/kg in 10% DMSO/PBS) daily or placebo (10% DMSO/PBS). A. The quantity of immunosuppressive cells is reduced. Dot plot of representative experiment. Numbers highlighted the percentage of M-MDSC and PMN-MDSC. Histogram showed results from 8 mice. B. The quantity of effector T cells (TyS, NK, CD4+) is increased. Histogram showed results from 8 mice. *, p<0.05; **, p<0.01 Mann-Whitney test.

Figure 12:
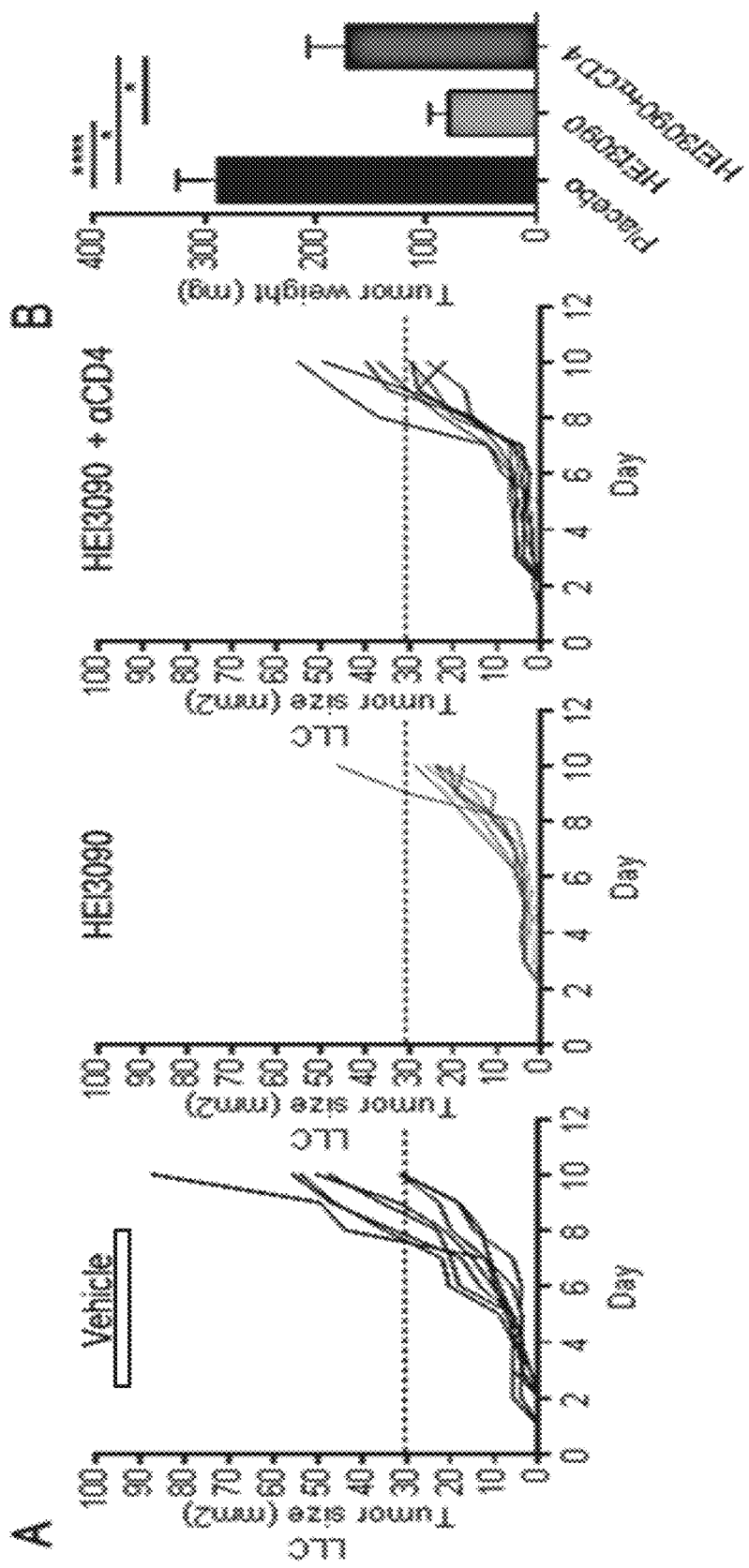

FIG. 12: T CD4+ cells are partly required to mediate HEI3090 anti tumor effect.

$5 \times 10^5$ LLC cells were injected sub cutaneously in the right flank of C57BL6 mice. Mice received HEI3090 (ip, 2.5 mg/kg in 10% DMSO/PBS) alone or in presence of anti CD4 antibody daily or placebo (10% DMSO/PBS). A. Tumor growth from the 3 groups was followed daily. B. tumor weight at sacrifice day (J12). *, p<0.05; ****, p<0.0001 (Mann-Whitney test).

Figure 13:
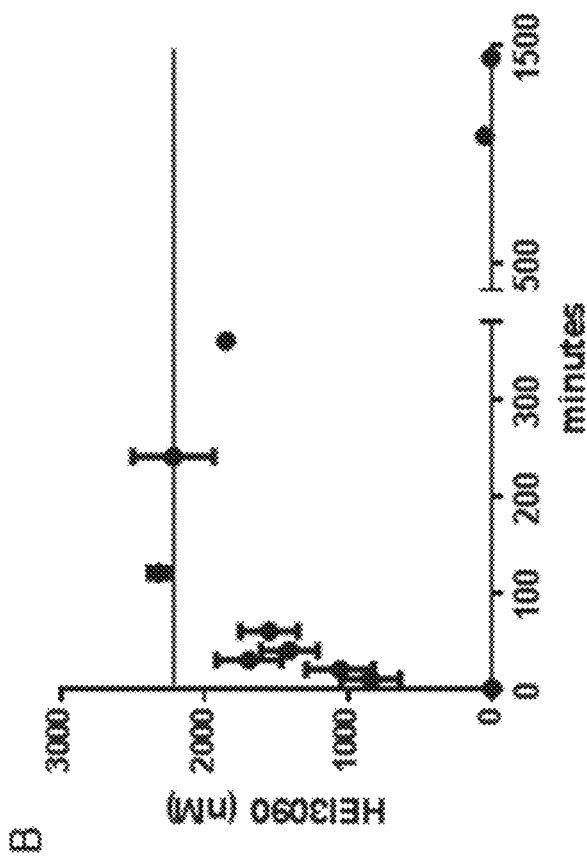

FIG. 13: ADME (absorption, distribution, metabolism and excretion) studies.

A. HEI-2328 and -3090 are stable molecules. Mouse liver microsomes from BD Gentest (ref 5345001) were incubated with HEI-2314, -2328, -2333 and -3090 at 1 μM for 0, 5, 10, 20, 30 and 40 min. The stability of the compounds was assayed by mass spectrometry.

B. HEI 3090 is found within plasma until 18 h after intraperitoneal administration. Intraperitoneal administration of HEI-3090 (0.166 mg/mL in 10% DMSO) was performed and serum was taken at 0, 10, 20, 30, 0, 60, 120, 240, 360, 1080 and 1440 min. Plasmatic concentration was determined by LC-MS/MS and reached a maximum of 2.5 μM.

Figure 14:
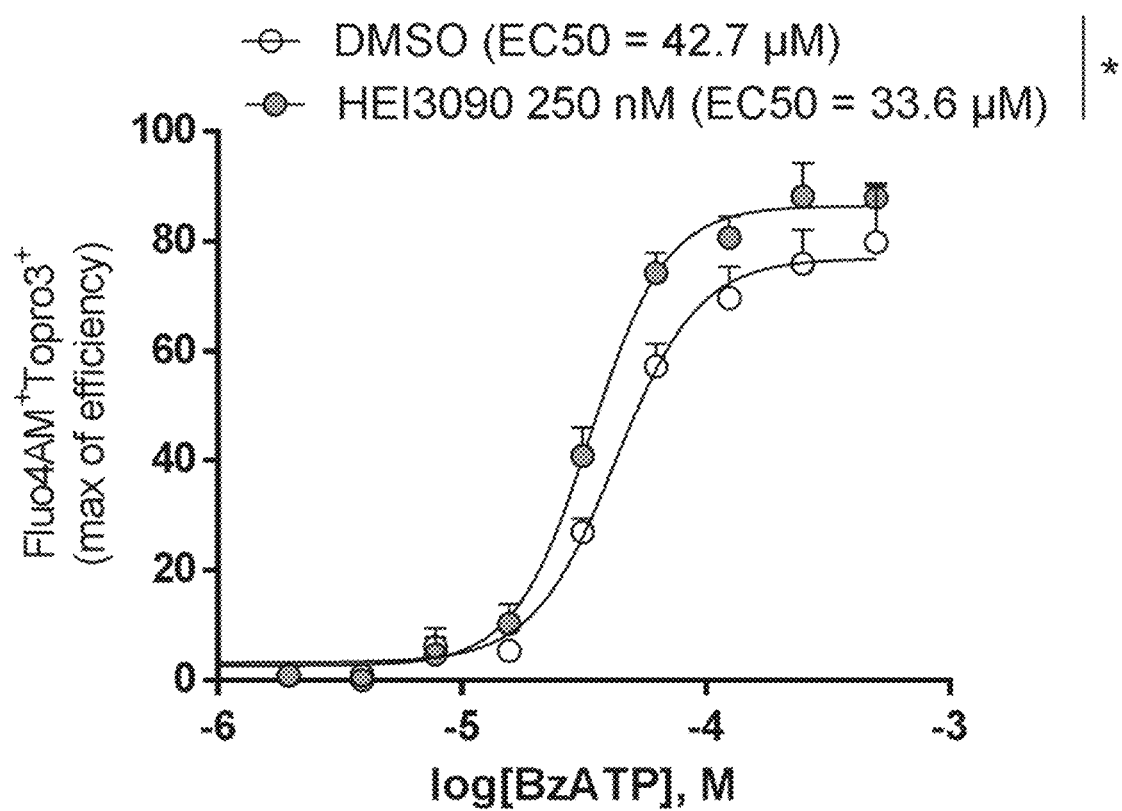

FIG. 14: HEI-3090 is a positive allosteric modulator of mouse P2RX7.

Calcium influx (Fluo-AM positive cells) and large cation permeation (Topro3 positive cells) were assayed by FACS 15 min after stimulation of HEK cells transfected with the mouse P2RX7 treated with increasing doses of BzATP.

In the presence of HEI3090 the EC50 is decreased by 22%.

Figure 15:
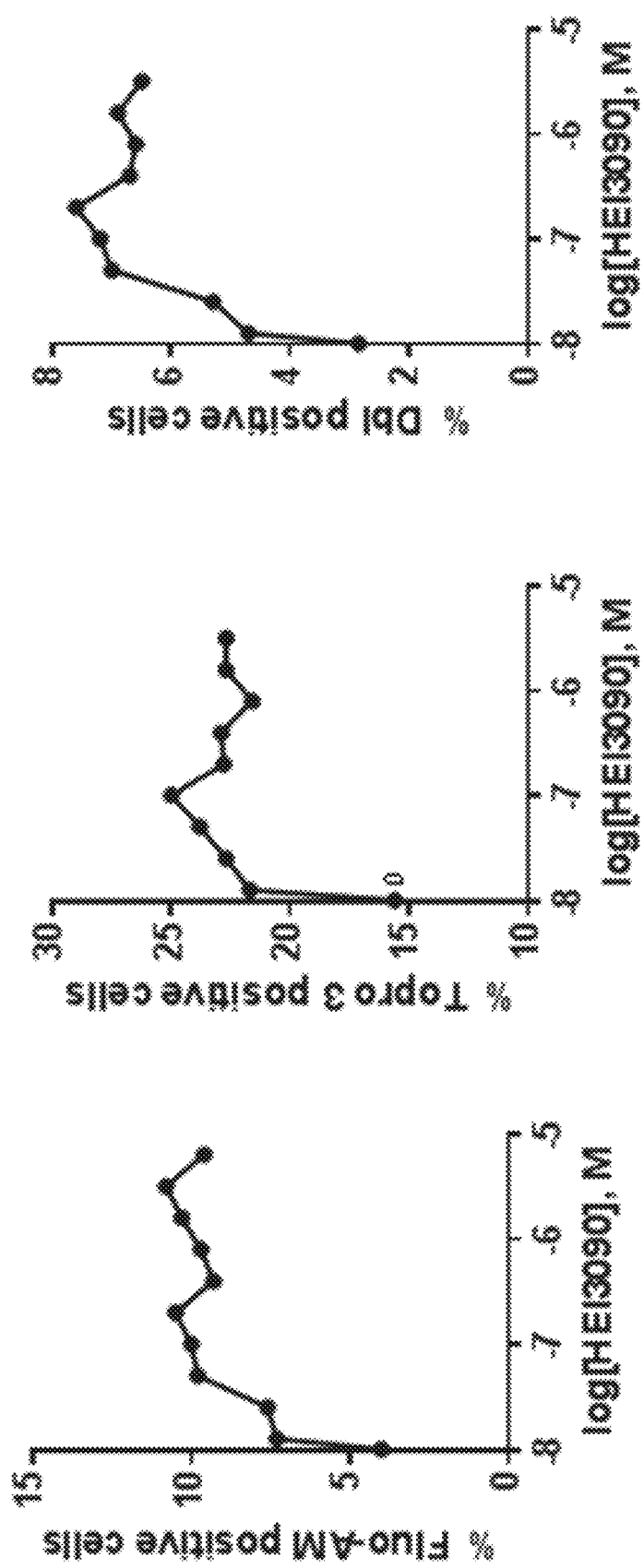

FIG. 15: HEI-3090 is a positive allosteric modulator of human P2RX7.

Calcium influx (Fluo-AM positive cells) and large cation permeation (Topro3 positive cells) were assayed by FACS 15 min after stimulation of HEK cells transfected with the human P2RX7 that were treated with increasing doses of HEI3090 in the presence of 7.8 μM BzATP. In the presence of HEI3090 both Ca and large cation influx are increased by 3 fold, indicating that the molecule is a positive allosteric modulator.

Figure 16:
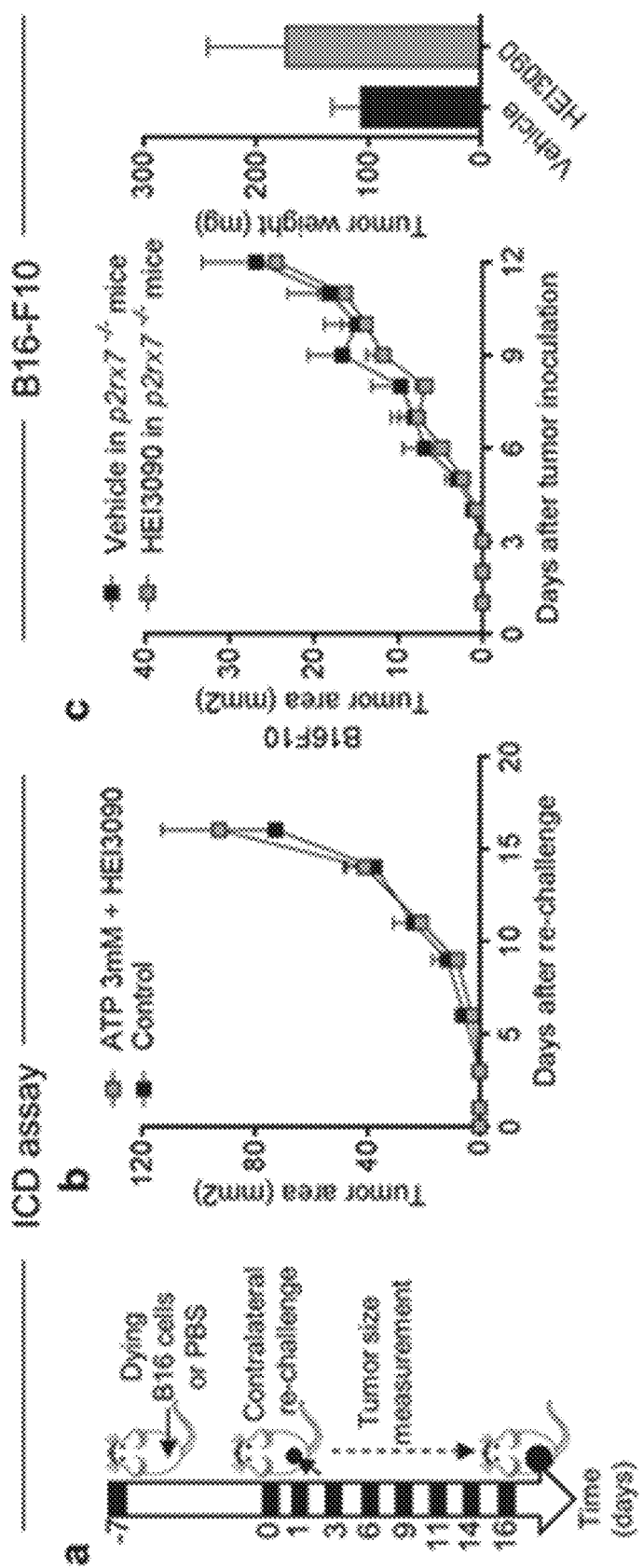
Figure 16:
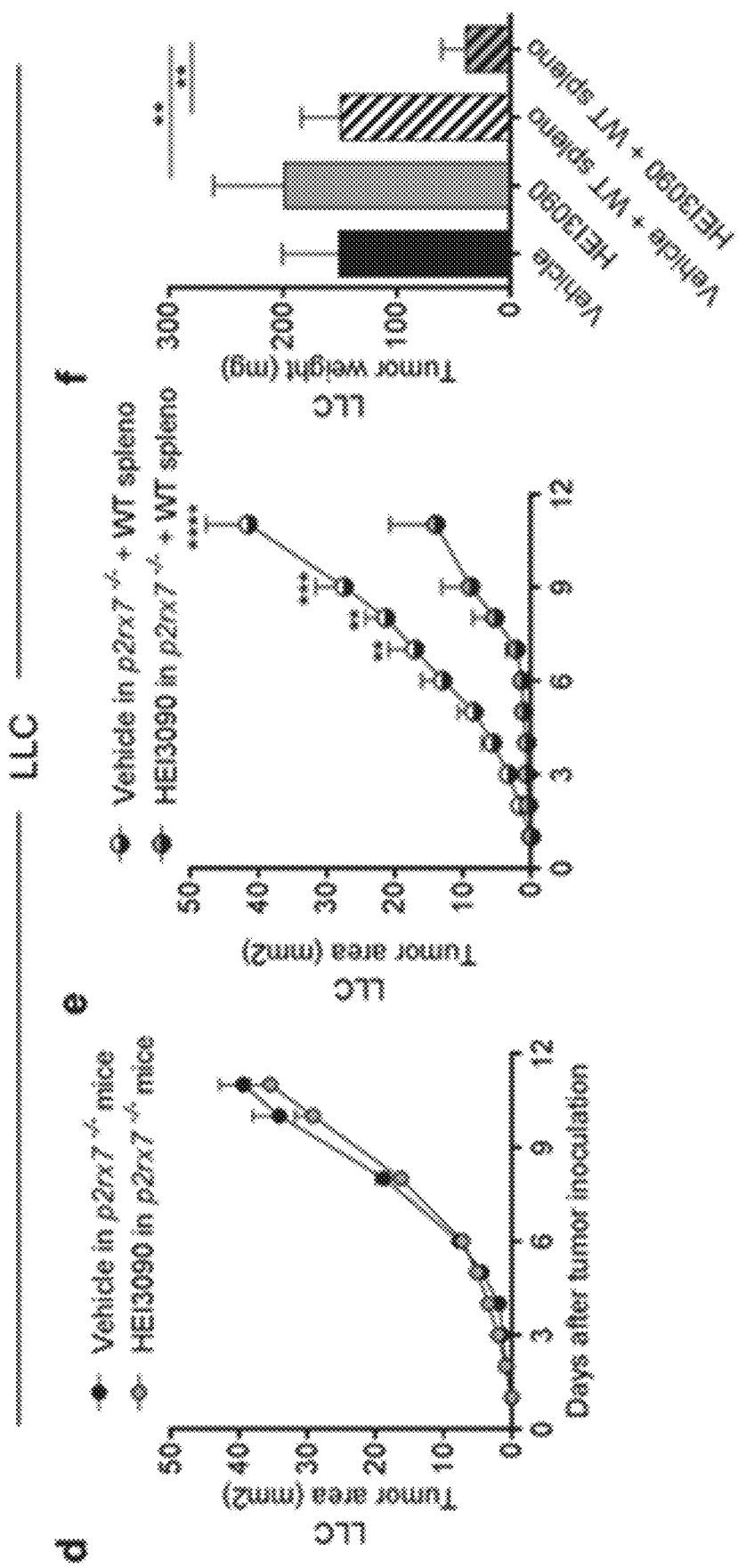

FIG. 16: HEI3090 promotes its anti-tumor effect by stimulating P2RX7 expressing immune cells and not immunogenic cell death (ICD).

a-b. In vivo assay for the evaluation of HEI3090 as an inducer of immunogenic cell death.

To induce B16-F10 death, cells were exposed to 3 mM ATP and 50 μM HEI3090 and 1.105 dying cells, or PBS as control, were injected sc in the right flank (n=4). 7 days later, 0.5.105 live B16-F10 cells were injected s.c. in the contralateral flank. (a). Curves shown mean of tumor growth in the contralateral site (b).

(c-f) Effect of HEI3090 on tumor growth in p2rx7 deficient mice ($p2rx7^{-/-}$). 5.105 B16-F10 (c) or 5.105 LLC (d) were injected s.c. into the flank of $p2rx7^{-/-}$ mice. Mice were treated i.p. with vehicle (PBS, 10% DMSO) or with HEI3090 (1.5 mg/kg in PBS, 10% DMSO) from day 1 to day 12. (e,f) p2rx7⁻/⁻ mice were adoptively transferred with 5.106 splenocytes from WT C57BL/6J mice and injected s.c into the flank with 5.105 LLC. Then mice were treated i.p. with vehicle (PBS, 10% DMSO) or with HEI3090 (1.5 mg/kg in PBS, 10% DMSO) from day 1 to day 12.

Figure 17:
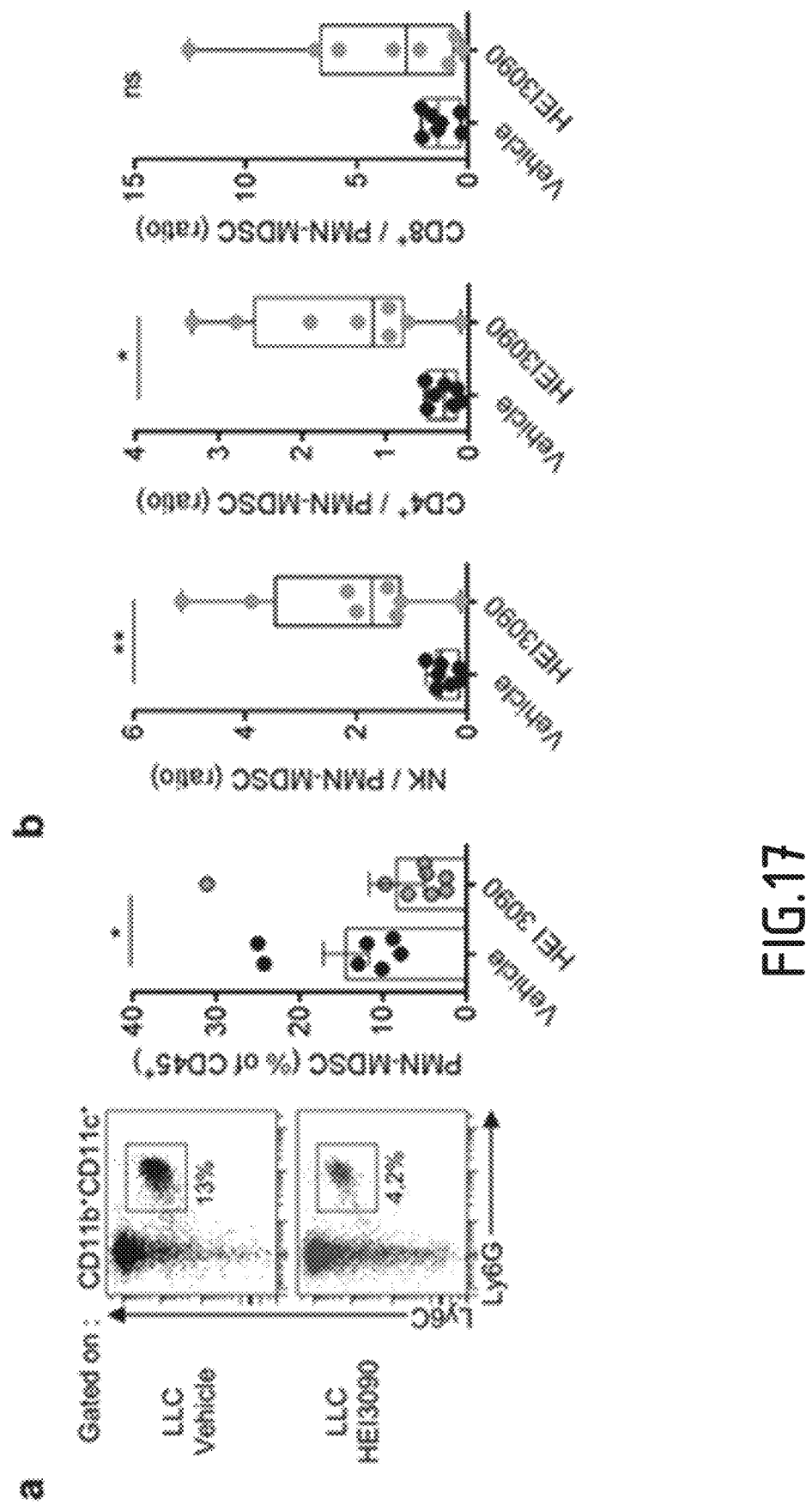
Figure 17:
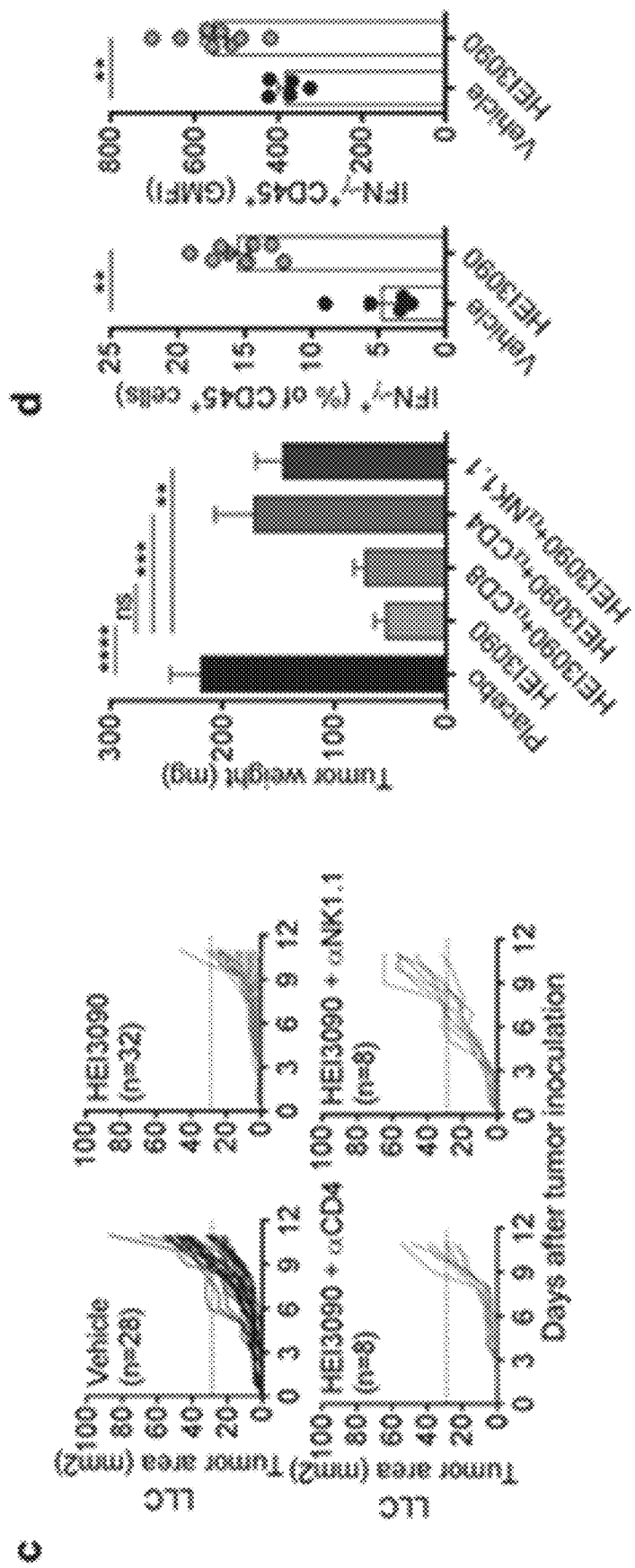
Figure 17:
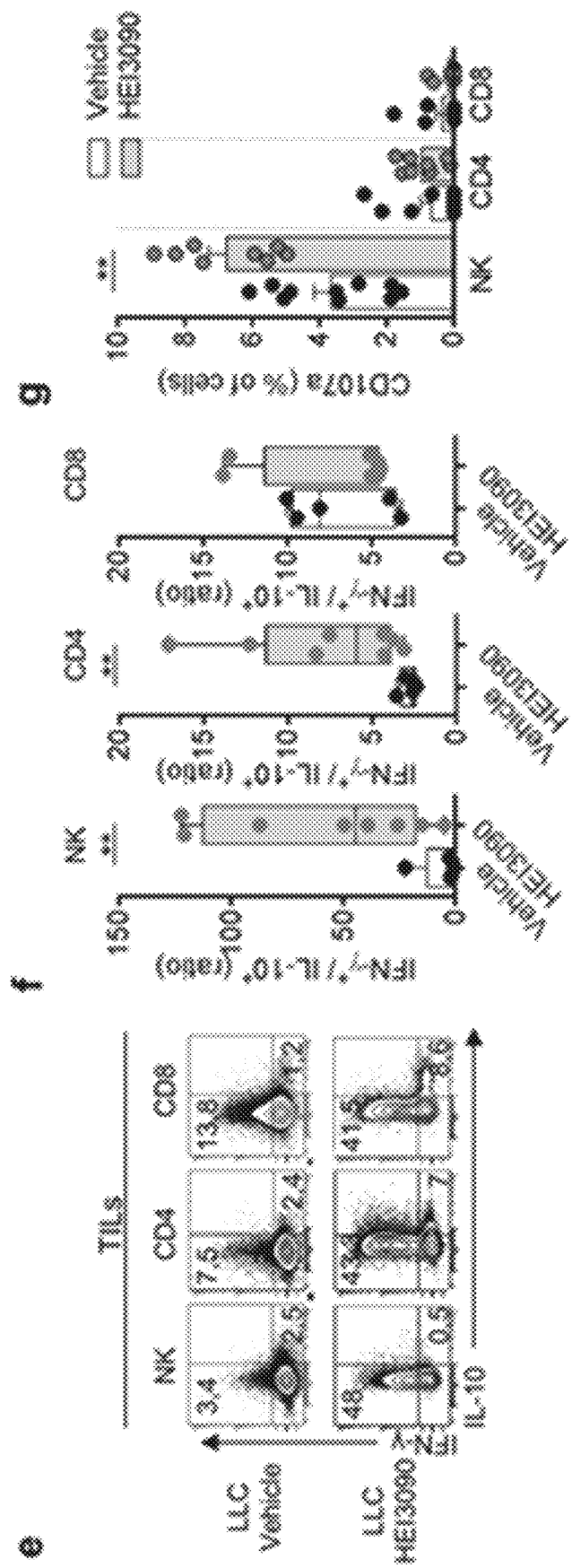

FIG. 17: HEI3090 stimulates effective functions of NK cells and CD4+ T cells (supplementary results of FIG. 12).

a, b. Phenotypic flow cytometry analyses of tumor infiltrating cells. LLC tumors were collected at day 12. Proportion of PMN-MDSC among CD45+ within LLC tumors from mice treated with vehicle or HEI3090 (a). Ratio of NK, CD4+ or CD8+ T cells on PMN-MDSC (b).

c, d. 5.105 LLC were injected s.c. into the flank of C57BL6/J mice. Then mice were treated i.p. with vehicle (PBS, 10% DMSO) or with HEI3090 (1.5 mg/kg in PBS, 10% DMSO) or with HEI3090 and depleting antibody against NK1.1, CD4+ or CD8+ T cells. Antibodies were administered i.p every 3 days (200 µg/injection). Spaghetti plots and tumor weight at day 12 (d). Each curve represents one mouse.

e-g Functional flow cytometry analyses of tumor infiltrating immune cells or splenocytes. Tumors were stimulated with PMA/ionomycine and production of IFN-γ and IL-10 were simultaneously analyzed in CD45+, NK, CD4+ or CD8+ T cells. Graphs shown proportion of IFN-γ producing cells into CD45+ cells or geometric mean of fluorescence (e). Representative dot plots of IFN-γ and IL-10 staining into TILs (f). Ratios of IFN-γ on IL-10 positive cells on each TIL. Degranulation assay of splenocytes from LLC tumor bearing mice treated with vehicle or HEI3090 (g) Splenocytes were re-stimulated with LLC in vitro and CD107a positive cells in NK, CD4+ and CD8+ T cells were represented.

Figure 18:
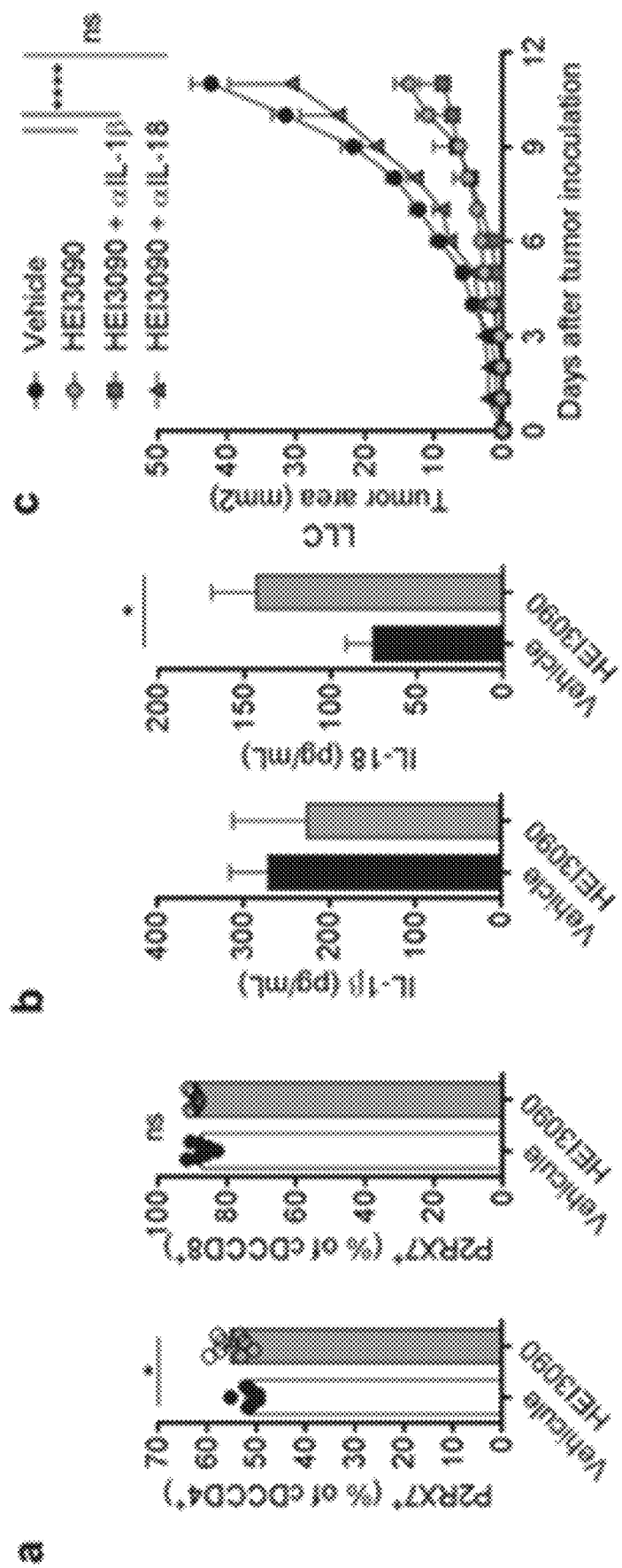
Figure 18:
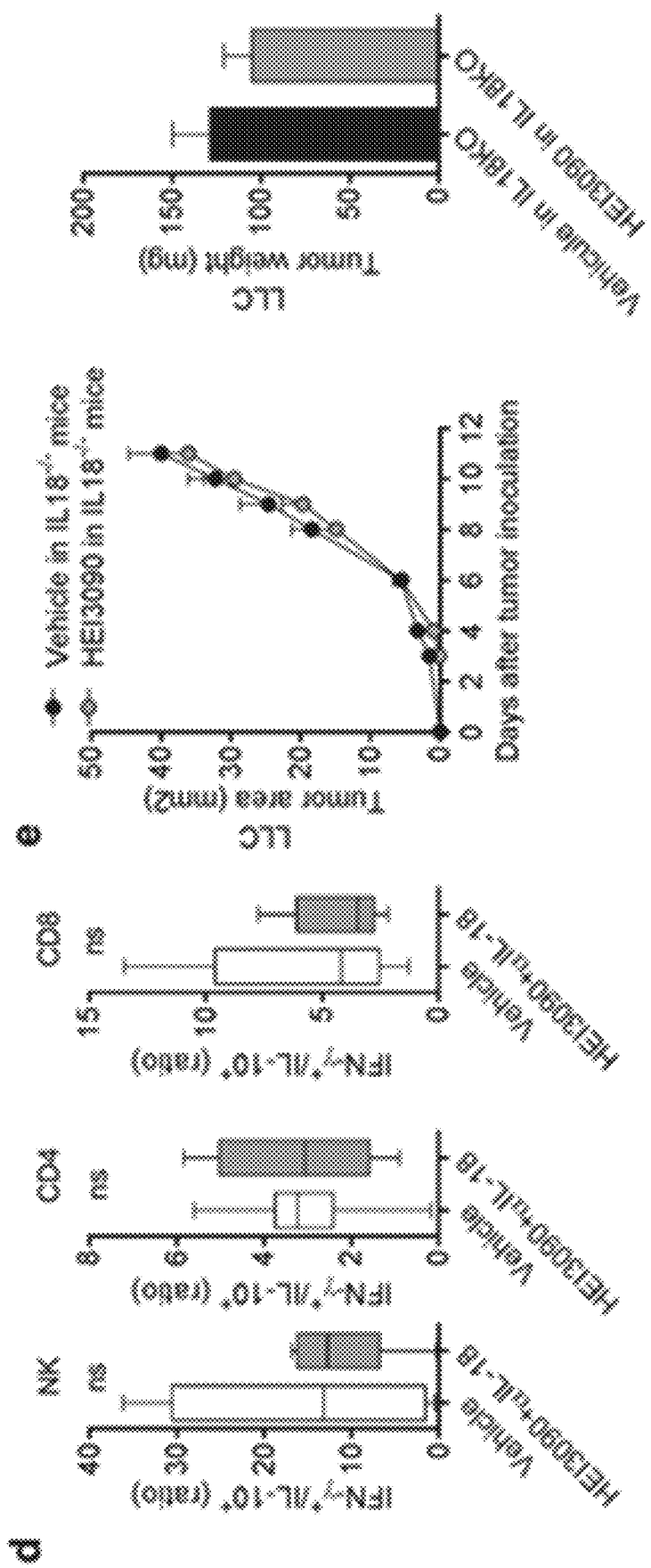
Figure 18:
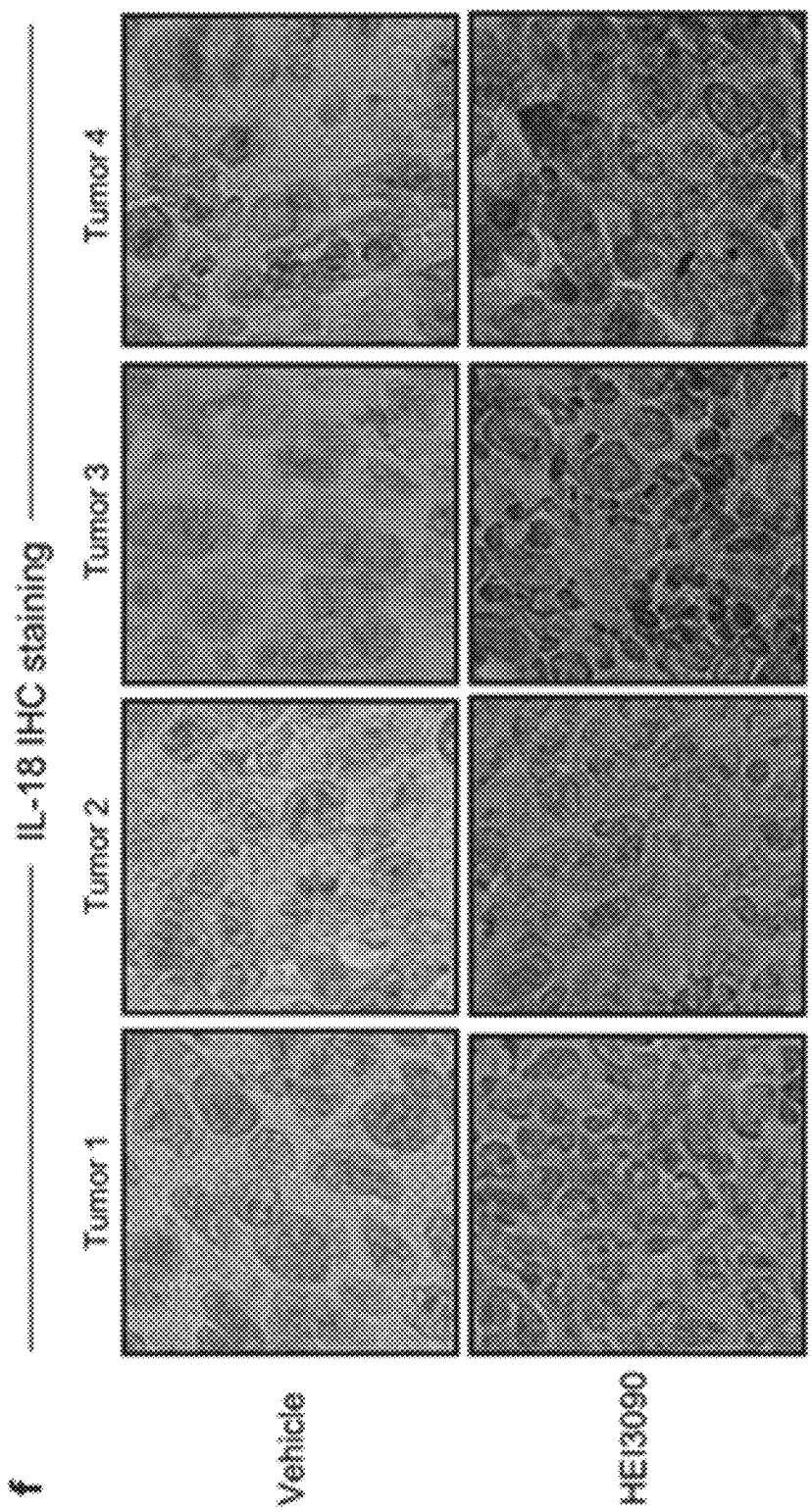

FIG. 18: HEI3090 induces IL-18 production in vivo.

a. Flow cytometry analyses of P2RX7 expression among conventional dendritic cells CD4+ or CD8+ within LLC tumors.

b. Protein levels of IL-1p and IL-18 in serum of LLC tumor bearing mice treated with vehicle or HEI3090, determined by ELISA.

c. 5.105 LLC were injected s.c. into the flank of C57BL6/J mice. Then mice were treated i.p. with vehicle (PBS, 10% DMSO) or with HEI3090 (1.5 mg/kg in PBS, 10% DMSO) or with HEI3090 and neutralizing antibody against IL-1p or IL-18 from day 1 to day 12. Antibodies were administered i.p every 3 days (200 µg/injection).

d. Flow cytometry analyses of IFN-γ and IL-10 production of intra-tumor NK, CD4+T or CD8+ T cells. Graph present ratio of IFN-γ on IL10 positive cells.

e. Effect of HEI3090 on tumor growth in IL-18 deficient mice (IL-18⁻/⁻). 5.105 LLC were injected s.c. into the flank of IL-18⁻/⁻ mice. Mice were treated i.p. with vehicle (PBS, 10% DMSO) or with HEI3090 (1.5 mg/kg in PBS, 10% DMSO) from day 1 to day 12.

f. IL-18 IHC staining in 4 LLC tumors from C57BL/6J mice treated with vehicle and 4 LLC tumors from C57BL/6J mice treated with HEI3090.

Figure 19:
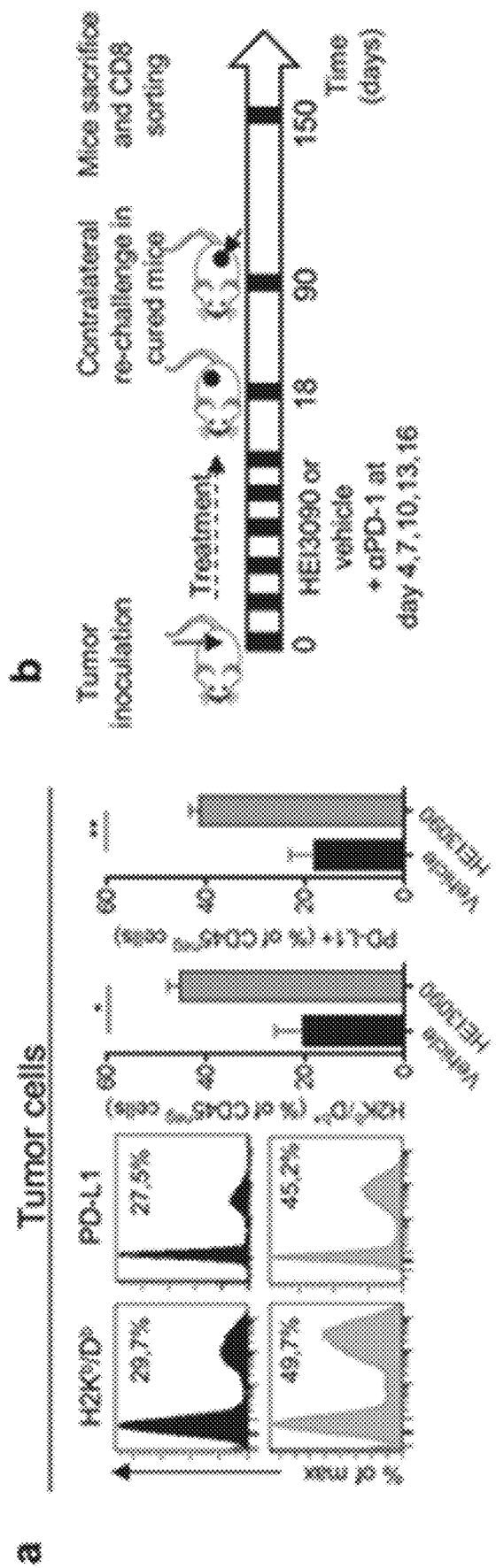
Figure 19:
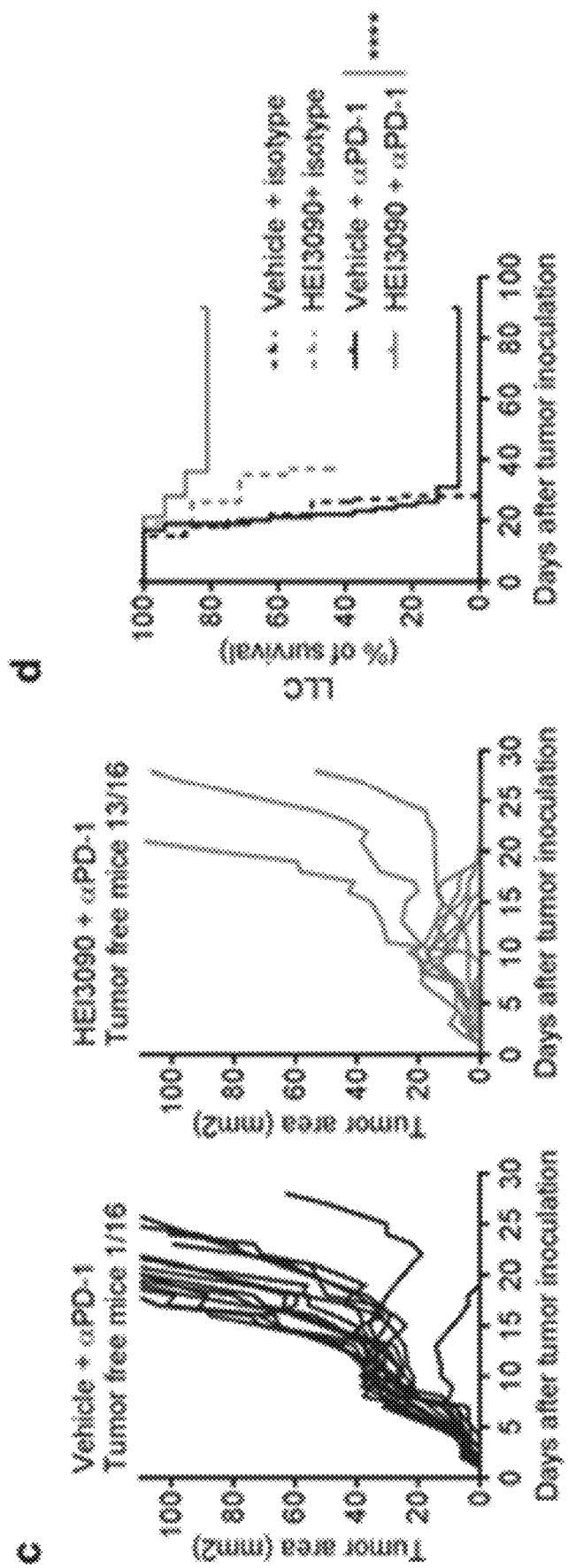
Figure 19:
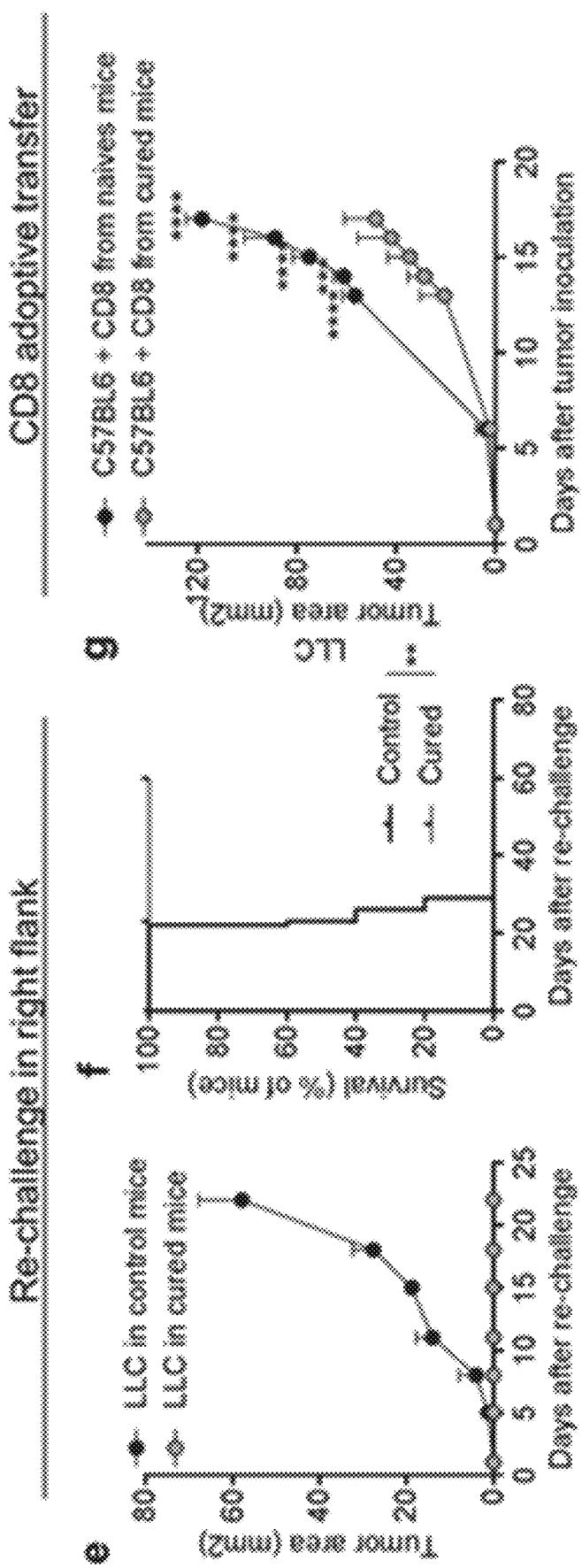

FIG. 19: Combination of HEI3090 and anti-PD-1 immune checkpoint inhibitor cured LLC tumor bearing mice (supplementary results of FIG. 10).

a. Flow cytometry analyses of MHC-1 and PD-L1 expression on CD45 negative cells in LLC tumors from mice treated with vehicle or HEI3090.

b-g Effect of HEI3090 and anti PD-1 checkpoint inhibitor on LLC tumor growth. 5.105 LLC were injected s.c. into the flank of C57BL6J mice. Mice were treated i.p. with vehicle (PBS, 10% DMSO) or with HEI3090 (1.5 mg/kg in PBS, 10% DMSO) from day 1 to day 18. Each mouse received 200 µg of anti PD-1 i.p. at day 4.7.10.13 and 16. Tumor sizes were measured from day 1 to day 90. Mice were sacrificed when tumor reached 100 mm2. For contralateral re-challenge, cured mice or naive age matched C57BL6J mice were injected s.c. in the opposite flank with 2.105 LLC. At day 150, re-challenged treated mice or C57BL/6J naive mice were sacrificed to sort CD8+ T cells. 2.105 CD8+ T cells were adoptively transferred in other C57BL6J naive mice. Then mice were injected s.c with 2.105 LLC (b). Spaghetti plots of LLC tumor growth of vehicle and anti-PD-1 treated mice or HEI3090 and anti-PD-1 treated mice (c). Each curve represents one mouse. Survival curves of mice treated with vehicle or HEI3090 and isotype control or vehicle or HEI3090 and anti-PD-1 (d). Tumor growth and survival curves after re-challenge of cured mice treated with HEI3090 and anti-PD-1 or age matched C57BL/6J mice (e,f). Tumor growth after i.v. injection of CD8+ T cells from naïve mice or re-challenged treated mice (g).

EXAMPLES

Example 1: Synthesis of Compounds HEI 2314, HEI 2328, HEI 2333, HEI 2336 and HEI 3090

General procedure for the synthesis of the compounds of the invention:

A mixture of N-(2,4-dichlorobenzyl)-5-oxopyrrolidine-2-carboxamide (1 equiv), and the corresponding isocyanate (1 equiv) in toluene was stirred for 1-24 hours at reflux under nitrogen atmosphere. The resulting mixture was purified by direct crystallization in MeCOH to afford pure compound.

The reaction scheme is as follows:

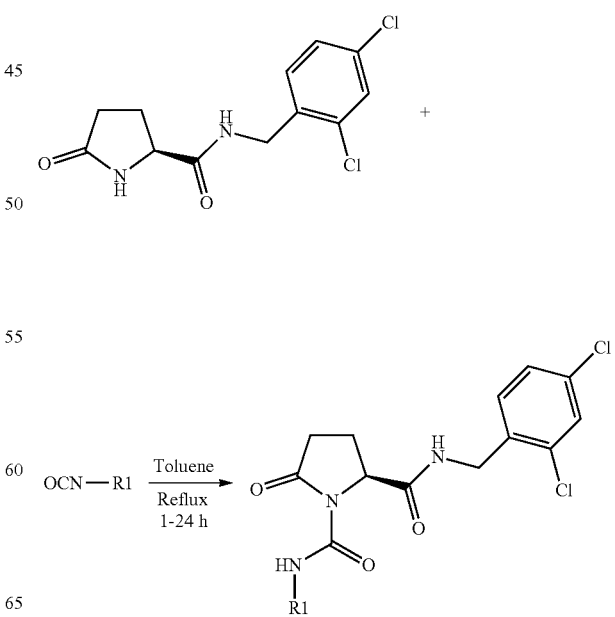

a) Synthesis of compound HEI_2347:

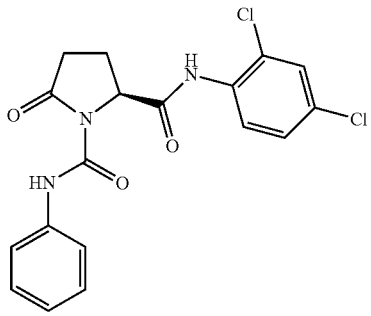 [SMILES: O=C(Nc1ccc(Cl)cc1Cl)[C@@H]1CCC(=O)N1C(=O)Nc1ccccc1]

(S)—N²-(2,4-Dichlorophenyl)-5-oxo-N¹-phenylpyrrolidine-1,2-dicarboxamide (HEI_2347). The general procedure was followed using (S)—N-(2,4-dichlorobenzyl)-5-oxo-pyrrolidine-2-carboxamide (0.90 g, 3.3 mmol), and phenyl isocyanate (0.39 g, 3.3 mmol). The desired product crystallizes in MeCOH as a white powder, which was filtered to afford pure HEI_2347 in 81% yield (1.05 g, 2.7 mmol). mp 214-217° C. (MeOH); TLC Rf (CH$_2$Cl$_2$/MeOH: 98/2) 0.9; $^1$H NMR (DMSO-d$_6$, 400 MHz) δ ppm 1.98-2.10 (m, 1H, CH$_2$CH$_2$CH), 2.38-2.48 (m, 1H, CH$_2$CH$_2$CH), 2.60-2.81 (m, 2H, CH$_2$CH$_2$CH), 5.08 (dd, J=5.6, 2.4 Hz, 1H, CH$_2$CH$_2$CH), 7.10 (t, J=7.2 Hz, 1H, ArH), 7.34 (t, J=7.2 Hz, 2H, ArH), 7.42 (dd, J=8.8, 2.4 Hz, 1H, ArH), 7.51 (d, J=7.2 Hz, 2H, ArH), 7.68 (d, J=2.4 Hz, 1H, ArH), 7.73 (d, J=8.8 Hz, 1H, ArH), 10.08 (br s, 1H, NH), 10.51 (br s, 1H, NH); $^{13}$C NMR (DMSO-d$_6$, 100 MHz) δ ppm 21.4 (CH$_2$), 31.7 (CH$_2$), 58.8 (CH), 119.6 (2 CH), 123.9 (CH), 127.3 (CH), 127.5 (CH), 127.6 (CH), 129.0 (C), 129.1 (2 CH), 129.7 (C), 133.6 (C), 137.2 (C), 149.3 (C), 170.2 (C), 177.8 (C); LC-MS (APCI$^+$) m/z: 392.1 (MH$^+$), tr 4.38 min: IR ν (cm$^{-1}$): 3275, 2922, 1723, 1693, 1662, 1559, 1473, 1219, 1100, 819; Anal. Calcd for C$_{18}$H$_{15}$Cl$_2$N$_3$O$_3$: C, 55.12; H, 3.85; N, 10.71. Found: C, 54.91; H, 3.89; N, 10.75%.

b) Synthesis of compound HEI_2346:

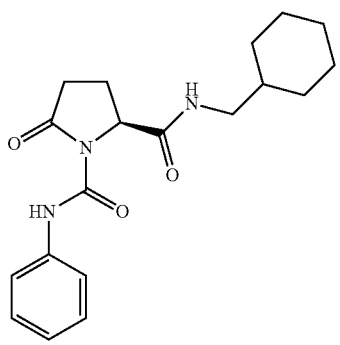 [SMILES: O=C(NCC1CCCCC1)[C@@H]1CCC(=O)N1C(=O)Nc1ccccc1]

(S)—N²-(Cyclohexylmethyl)-5-oxo-N¹-phenylpyrrolidine-1,2-dicarboxamide (HEI_2346). The general procedure was followed using (S)—N-cyclohexylmethyl-5-oxo-pyrrolidine-2-carboxamide (0.40 g, 1.8 mmol), and phenyl isocyanate (0.21 g, 1.8 mmol). The desired product was purified on a silica column (EtOAc/n-heptane 4/6 to 5/5) to afford pure HEI_2346 as a white solid in 88% yield (1.05 g, 8.8 mmol). mp 122-127° C. (EtOAc/n-heptane); TLC Rf (EtOAc/n-heptane: 1/1) 0.3; $^1$H NMR (CDCl$_3$, 400 MHz) δ ppm 0.85-0.97 (m, 2H, cyclohex-H), 1.08-1.28 (m, 3H, cyclohex-H), 1.45-1.46 (m, 1H, cyclohex-H), 1.60-1.74 (m, 5H, cyclohex-H), 2.15-2.25 (m, 1H, CH$_2$CH$_2$CH), 2.30-2.40 (m, 1H, CH$_2$CH$_2$CH), 2.55-2.62 (m, 1H, CH$_2$CH$_2$CH), 3.00-3.20 (m, 3H, NHCH$_2$ and CH$_2$CH$_2$CH), 4.79 (dd, J=8.4, 1.6 Hz, 1H, CH$_2$CH$_2$CH), 6.59 (s, 1H, NHCH$_2$), 7.11 (t, J=7.6 Hz, 1H, ArH), 7.32 (t, J=7.6 Hz, 2H, ArH), 7.47 (d, J=7.6 Hz, 2H, ArH), 10.56 (br s, 1H, NHAr); $^{13}$C NMR (CDCl$_3$, 100 MHz) δ ppm 21.6 (CH$_2$), 25.9 (2 CH$_2$), 26.4 (CH$_2$), 30.8 (2 CH$_2$), 32.8 (CH$_2$), 38.0 (CH$_2$), 46.0 (CH), 59.4 (CH), 120.5 (2 CH), 124.6 (CH), 129.1 (2 CH), 137.1 (C), 150.6 (C), 170.3 (C), 177.8 (C); LC-MS (APCI$^+$) m/z: 344.2 (MH$^+$), tr 4.16 min; IR ν (cm$^{-1}$): 3289, 2922, 2851, 1718, 1654, 1552, 1446, 1217, 747; Anal. Calcd for C$_{19}$H$_{25}$N$_3$O$_3$: C, 66.45; H, 7.34; N, 12.24. Found: C, 66.71; H, 7.42; N, 11.68%.

c) Synthesis of compound HEI_2269:

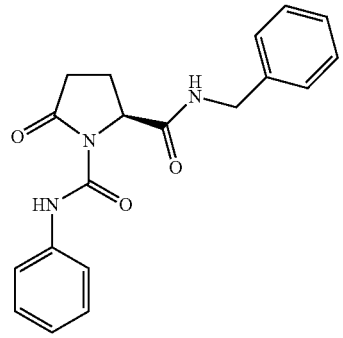 [SMILES: O=C(NCc1ccccc1)[C@@H]1CCC(=O)N1C(=O)Nc1ccccc1]

(S)—N²-Benzyl-5-oxo-N¹-phenylpyrrolidine-1,2-dicarboxamide (HEI_2269). The general procedure was followed using (S)—N-benzyl-5-oxo-pyrrolidine-2-carboxamide (0.35 g, 1.4 mmol), and phenyl isocyanate (0.15 g, 1.4 mmol). The desired product was purified on a silica column (CH$_2$Cl$_2$/MeOH l/O to 98/2) to afford pure HEI_2269 as a white solid in 70% yield (0.33 g, 1.0 mmol). mp 164-165° C. (CH$_2$Cl$_2$/MeOH); TLC Rf (CH$_2$Cl$_2$/MeOH: 97/3) 0.2; $^1$H NMR (DMSO-d$_6$, 400 MHz) δ ppm 1.90-2.10 (m, 2H, CH$_2$CH$_2$CH), 2.22-2.40-2.42 (m, 2H, CH$_2$CH$_2$CH), 4.27 (m, 3H, CH$_2$CH$_2$CH and NHCH$_2$), 7.25 (m, 3H, ArH), 7.28-7.41 (m, 5H, ArH), 7.47 (t, J=7.6 Hz, 2H, ArH), 8.39 (t, J=5.2 Hz, 1H, NHCH$_2$), 8.51 (br s, 1H, NHAr); $^{13}$C NMR (DMSO-d$_6$, 100 MHz) δ ppm 27.4 (CH$_2$), 30.1 (CH$_2$), 42.1 (CH$_2$), 55.7 (CH), 126.7 (CH), 126.8 (2 CH), 127.2 (2 CH), 127.7 (CH), 128.3 (2 CH), 128.7 (2 CH), 132.2 (C), 139.5 (C), 155.6 (C), 171.0 (C), 173.1 (C); LC-MS (APCI$^+$) m/z: 338.2 (MH$^+$), tr 3.07 min; IR ν (cm$^{-1}$): 3367, 3183, 1705, 1645, 1416, 1175, 701; Anal. Calcd for C$_{19}$H$_{19}$N$_3$O$_3$: C, 67.64; H, 5.68; N, 12.45. Found: C, 67.72; H, 5.82; N, 12.13%.

d) Synthesis of compound HEI_2298:

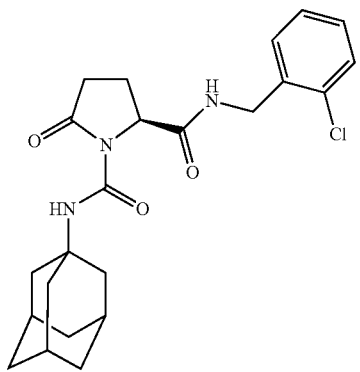 [SMILES: O=C(NCc1ccccc1Cl)[C@@H]1CCC(=O)N1C(=O)NC12CC3CC(CC(C3)C1)C2]

(S)—N$^1$-Adamantyl-N$^2$-(2-chlorobenzyl)-5-oxopyrrolidine-1,2-dicarboxamide (HEI_2298). The general procedure was followed using (S)—N-(2-chlorobenzyl)-5-oxo-pyrrolidine-2-carboxamide (1.43 g, 5.6 mmol), and adamantyl isocyanate (1.00 g, 5.6 mmol). The desired product was purified on a silica column (EtOAc/n-heptane 4/6 to 6/4) to afford pure HEI_2298 as a white solid in 62% yield (1.50 g, 3.5 mmol). mp 79-80° C. (EtOAc/n-heptane); TLC Rf (CH$_2$C2/MeOH: 98/2) 0.6; $^1$H NMR (CDCl$_3$, 400 MHz) δ ppm 1.68 (s, 6H, ADM-H), 1.98 (s, 6H, ADM-H), 2.09 (s, 3H, ADM-H), 2.10-2.18 (m, 1H, CH$_2$CH$_2$CH), 2.38-2.45 (m, 1H, CH$_2$CH$_2$CH), 2.46-2.52 (m, 1H, CH$_2$CH$_2$CH), 2.89-2.97 (m, 1H, CH$_2$CH$_2$CH), 4.51 (dd, J=14.2, 5.0 Hz, 1H, NHCH$_2$), 4.55 (dd, J=14.2, 5.0 Hz, 1H, NHCH$_2$), 4.76 (dd, J=8.8, 1.6 Hz, 1H, CH$_2$CH$_2$CH), 7.14 (t, J=5.0 Hz, 1H, ArH), 7.21 (m, 2H, ArH), 7.35 (m, 2H, ArH and NHCH$_2$), 8.39 (br s, 1H, NHAr); $^{13}$C NMR (CDCl$_3$, 100 MHz) δ ppm 21.1 (CH$_2$), 29.5 (2 CH$_2$), 32.9 (CH$_2$), 36.4 (2 CH$_2$), 41.6 (CH$_2$), 41.7 (2 CH$_2$), 51.9 (CH), 59.0 (CH), 127.1 (2 CH), 128.9 (2 CH), 129.6 (2 CH), 129.7 (C), 133.6 (C), 135.4 (C), 151.4 (C), 170.5 (C), 177.3 (C); LC-MS (APCI$^+$) m/z: 430.1 (MH$^+$), tr 4.60 min; IR v (cm$^{-1}$): 3289, 2906, 2849, 1715, 1663, 1538, 1223, 1033, 749; Anal. Calcd for C$_{23}$H$_{28}$ClN$_3$O$_3$: C, 64.25; H, 6.56; N, 9.77. Found: C, 64.32; H, 6.89; N, 9.58%.

e) Synthesis of compound HEI_2535:

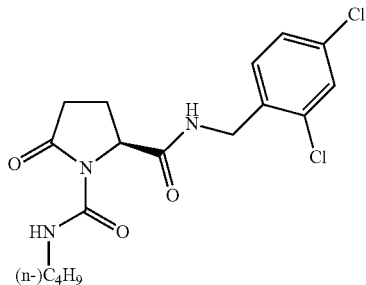

(S)—N-Butyl-N$^2$-(2,4-dichlorobenzyl)-5-oxopyrrolidine-1,2-dicarboxamide (HEI_2535)

The general procedure was followed using (S)—N-(2,4-dichlorobenzyl)-5-oxo-pyrrolidine-2-carboxamide (1.97 g, 6.9 mmol), and n-butyl isocyanate (0.75 g, 7.6 mmol). The desired product crystallizes in MeCOH as a white powder, which was filtered to afford pure HEI_2535 in 71% yield (1.89 g, 4.9 mmol). mp 162-163° C. (MeOH); TLC Rf (CH$_2$C2/MeOH: 99/1) 0.4; $^1$H NMR (CDCl$_3$, 400 MHz) ppm 0.92 (t, J=7.4 Hz, 3H, CH$_3$CH$_2$), 1.35 (m, 2H, CH$_3$CH$_2$), 1.51 (quint, J=7.8 Hz, 2H, CH$_2$CH$_2$CH$_2$), 2.12 (td, J=18.0, 11.3, 8.7 Hz, 1H, CH$_2$CH$_2$CH), 2.39 (m, 1H, CH$_2$CH$_2$CH), 2.49 (td, J=17.7, 9.4, 2.0 Hz, 1H, CH$_2$CH$_2$CH), 2.92 (td, J=17.5, 11.3, 9.4 Hz, 1H, CH$_2$CH$_2$CH), 3.27 (dq, J=7.1, 1.6 Hz, 2H, CH$_2$NHCO), 4.47 (dd, J=6.0, 2.8 Hz, 2H, NHCH$_2$Ar), 4.75 (dd, J=9.0, 1.6 Hz, 1H, CH$_2$CH$_2$CH), 7.08 (br t, J=5.7 Hz, 1H, NHCH$_2$Ar), 7.20 (dd, J=8.2, 2.3 Hz, 1H, ArH), 7.29 (d, J=8.2 Hz, 1H, ArH), 7.36 (d, J=2.0 Hz, 1H, ArH), 8.43 (br t, J=5.9 Hz, 1H, NHCH$_2$CH$_2$); $^{13}$C NMR (CDCl$_3$, 100 MHz) δ ppm 13.7 (CH$_3$), 20.0 (CH$_2$), 21.1 (CH$_2$), 31.6 (CH$_2$), 32.5 (CH$_2$), 39.7 (CH$_2$), 41.1 (CH$_2$), 59.0 (CH), 127.3 (CH), 129.3 (CH), 130.6 (CH), 133.9 (C), 134.0 (C), 134.1 (C), 153.1 (C), 170.3 (C), 177.2 (C); IR v (cm$^{-1}$): 3270, 1712, 1683, 1649, 1465, 1236, 1101, 810, 653; Anal. Calcd for C$_{17}$H$_{21}$Cl$_2$N$_3$O$_3$: C, 52.86; H, 5.48; N, 10.88. Found: C, 52.50; H, 5.88; N, 11.11%.

f) Synthesis of compound HEI_2541

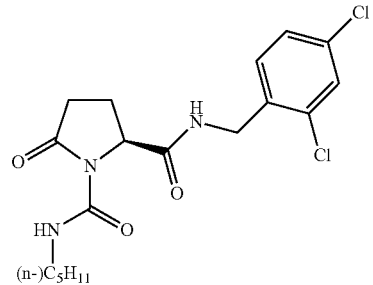

(S)—N$^2$-(2,4-Dichlorobenzyl)-5-oxo-N$^1$-pentylpyrrolidine-1,2-dicarboxamide (HEI_2541)

The general procedure was followed using (S)—N-(2,4-dichlorobenzyl)-5-oxo-pyrrolidine-2-carboxamide (1.73 g, 6.0 mmol), and n-pentyl isocyanate (0.75 g, 6.6 mmol). The desired product crystallizes in MeCOH as a white powder, which was filtered to afford pure HEI_2541 in 70% yield (1.67 g, 4.2 mmol). mp 159-160° C. (MeOH); TLC Rf (CH$_2$Cl$_2$/MeOH: 99/1) 0.7; $^1$H NMR (CDCl$_3$, 400 MHz) ppm 0.96 (t, J=6.9 Hz, 3H, CH$_3$CH$_2$), 1.39 (m, 4H, CH$_2$(CH$_2$)$_2$CH$_2$), 1.59 (quint, J=7.3 Hz, 2H, CH$_3$CH$_2$), 2.19 (m, 1H, CH$_2$CH$_2$CH), 2.41 (m, 1H, CH$_2$CH$_2$CH), 2.56 (td, J=17.6, 9.4, 1.9 Hz, 1H, CH$_2$CH$_2$CH), 2.99 (td, J=17.6, 11.3, 9.3 Hz, 1H, CH$_2$CH$_2$CH), 3.32 (qd, J=7.4, 2.8 Hz, 2H, CH$_2$(CH$_2$)), 4.54 (dd, J=7.5, 6.3 Hz, 2H, NHCH$_2$Ar), 4.82 (dd, J=9.1, 1.6 Hz, 1H, CH$_2$CH$_2$CH), 7.18 (br t, J=6.0 Hz, 1H, NHCH$_2$Ar), 7.26 (dd, J=8.2, 2.4 Hz, 1H, ArH), 7.36 (d, J=8.2 Hz, 1H, ArH), 7.43 (d, J=2.3 Hz, 1H, ArH), 8.51 (br t, J=5.7 Hz, 1H, NH(CH$_2$)$_2$); $^{13}$C NMR (CDCl$_3$, 100 MHz) δ ppm 13.9 (CH$_3$), 21.2 (CH$_2$), 22.3 (CH$_2$), 29.0 (CH$_2$), 29.2 (CH$_2$), 32.5 (CH$_2$), 40.0 (CH$_2$), 41.1 (CH$_2$), 59.0 (CH), 127.3 (CH), 129.3 (CH), 130.5 (CH), 133.9 (C), 134.1 (C), 153.1 (C), 170.4 (C), 177.2 (2 C); IR v (cm$^{-1}$): 3318, 1710, 1664, 1561, 1530, 1358, 1259, 830, 630; Anal. Calcd for C$_{18}$H$_{23}$Cl$_2$N$_3$O$_3$: C, 54.01; H, 5.79; N, 10.50. Found: C, 53.70; H, 5.95; N, 10.59%.

g) Synthesis of compound HEI_2534:

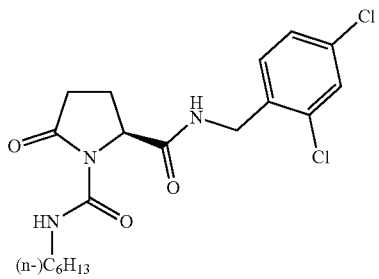

(S)—N²-(2,4-Dichlorobenzyl)-N-hexyl-5-oxopyrrolidine-1,2-dicarboxamide (HEI_2534)

The general procedure was followed using (S)—N-(2,4-dichlorobenzyl)-5-oxo-pyrrolidine-2-carboxamide (1.54 g, 5.4 mmol), and n-hexyl isocyanate (0.75 g, 5.9 mmol). The desired product crystallizes in MeCOH as a white powder, which was filtered to afford pure HEI_2534 in 66% yield (1.47 g, 3.5 mmol). mp 141-142° C. (MeOH); TLC Rf (CH$_2$C2/MeOH: 99/1) 0.4; $^1$H NMR (CDCl$_3$, 400 MHz) 0.90 (t, J=6.9 Hz, 3H, CH$_3$CH$_2$), 1.32 (m, 6H, CH$_2$(CH$_2$)$_3$CH$_2$), 1.54 (q, J=6.7 Hz, 2H, CH$_3$CH$_2$), 2.14 (m, 1H, CH$_2$CH$_2$CH), 2.41 (m, 1H, CH$_2$CH$_2$CH), 2.52 (td, J=17.5, 9.3, 2.0 Hz, 1H, CH$_2$CH$_2$CH), 2.94 (td, J=17.9, 11.4, 9.6 Hz, 1H, CH$_2$CH$_2$CH), 3.82 (dq, J=7.3, 1.7 Hz, 2H, CH$_2$(CH$_2$)$_4$), 4.50 (dd, J=5.8, 4.5 Hz, 2H, NHCH$_2$Ar), 4.77 (dd, J=8.6, 1.4 Hz, 1H, CH$_2$CH$_2$CH), 7.11 (br t, J=5.5 Hz, 1H, NHCH$_2$Ar), 7.22 (dd, J=8.2, 2.0 Hz, 1H, ArH), 7.31 (d, J=8.2 Hz, 1H, ArH), 7.39 (d, J=2.1 Hz, 1H, ArH), 8.46 (br t, J=5.7 Hz, 1H, NH(CH$_2$)$_2$); $^{13}$C NMR (CDCl$_3$, 100 MHz) δ ppm 14.0 (CH$_3$), 21.1 (CH$_2$), 22.5 (CH$_2$), 26.5 (CH$_2$), 29.5 (CH$_2$), 31.4 (CH$_2$), 32.5 (CH$_2$), 40.1 (CH$_2$), 41.1 (CH$_2$), 59.0 (CH), 127.3 (CH), 129.3 (CH), 130.6 (CH), 133.9 (C), 134.0 (C), 134.1 (C), 153.1 (C), 170.3 (C), 177.2 (C); IR v (cm$^{-1}$): 3313, 2926, 2865, 1708, 1664, 1355, 1253, 1153, 829, 654; Anal. Calcd for C$_{19}$H$_{25}$Cl$_2$N$_3$O$_3$: C, 55.08; H, 6.08; N, 10.14. Found: C, 55.02; H, 6.15; N, 10.27%.

h) Synthesis of compound HEI_2542:

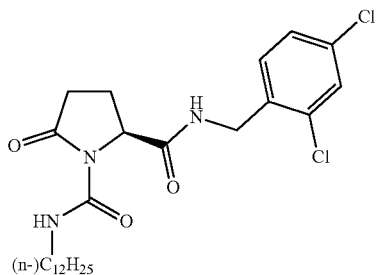

(S)—N²-(2,4-Dichlorobenzyl)-N-dodecyl-5-oxopyrrolidine-1,2-dicarboxamide (HEI_2542)

The general procedure was followed using (S)—N-(2,4-dichlorobenzyl)-5-oxo-pyrrolidine-2-carboxamide (0.93 g, 3.2 mmol), and n-dodecyl isocyanate (0.75 g, 3.5 mmol). The desired product crystallizes in MeCOH as a white powder, which was filtered to afford pure HEI_2542 in 49% yield (0.78 g, 1.6 mmol). mp 124-125° C. (MeOH); TLC Rf (CH$_2$C2/MeOH: 99/1) 0.8; $^1$H NMR (CDCl$_3$, 400 MHz) ppm 0.88 (t, J=6.6 Hz, 3H, CH$_3$CH$_2$), 1.26 (m, 18H, CH$_2$(CH$_2$)$_9$CH$_2$), 1.53 (quint, J=6.7 Hz, 2H, CH$_3$CH$_2$), 2.13 (m, 1H, CH$_2$CH$_2$CH), 2.40 (m, 1H, CH$_2$CH$_2$CH), 2.51 (td, J=17.6, 9.3, 1.8 Hz, 1H, CH$_2$CH$_2$CH), 2.93 (td, J=17.7, 11.3, 9.5 Hz, 1H, CH$_2$CH$_2$CH), 3.29 (q, J=7.2 Hz, 2H, CH$_2$(CH$_2$)$_{10}$), 4.48 (dd, J=6.2 Hz, 2H, NHCH$_2$Ar), 4.76 (dd, J=8.9, 1.2 Hz, 1H, CH$_2$CH$_2$CH), 7.11 (br t, J=5.9 Hz, 1H, NHCH$_2$Ar), 7.21 (dd, J=8.3, 2.2 Hz, 1H, ArH), 7.30 (d, J=8.2 Hz, 1H, ArH), 7.37 (d, J=2.1 Hz, 1H, ArH), 8.45 (br t, J=6.0 Hz, 1H, NH(CH$_2$)$_2$); $^{13}$C NMR (CDCl$_3$, 100 MHz) δ ppm 14.1 (CH$_3$), 21.1 (CH$_2$), 22.7 (CH$_2$), 26.9 (CH$_2$), 29.3 (CH$_2$), 29.3 (CH$_2$), 29.5 (CH$_2$), 29.5 (CH$_2$), 29.6 (CH$_2$), 29.6 (CH$_2$), 29.6 (CH$_2$), 31.9 (CH$_2$), 32.5 (CH$_2$), 40.1 (CH$_2$), 41.1 (CH$_2$), 59.0 (CH), 127.3 (CH), 129.3 (CH), 130.5 (CH), 133.9 (C), 133.9 (C), 134.1 (C), 153.1 (C), 170.3 (C), 177.2 (C); IR v (cm$^{-1}$): 3302, 2918, 2850, 1718, 1658, 1541, 1349, 1251, 832, 648; Anal. Calcd for C$_{25}$H$_{37}$Cl$_2$N$_3$O$_3$: C, 60.2; H, 7.48; N, 8.43. Found: C, 59.8; H, 7.5; N, 8.5%.

i) Synthesis of compound HEI_2537:

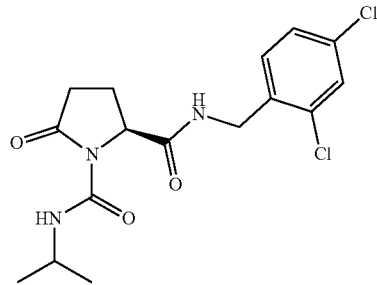 [SMILES: CC(C)NC(=O)N1C(=O)CC[C@H]1C(=O)NCc1ccc(Cl)cc1Cl]

(S)—N²-(2,4-Dichlorobenzyl)-5-oxo-N¹-(propan-2-yl)pyrrolidine-1,2-dicarboxamide (HEI_2537)

The general procedure was followed using (S)—N-(2,4-dichlorobenzyl)-5-oxo-pyrrolidine-2-carboxamide (2.30 g, 8.0 mmol), and propan-2-yl isocyanate (0.75 g, 8.8 mmol). The desired product was purified on a silica column (EtOAc/n-heptane 1/9 to I/O) to afford pure HEI_2537 as a yellow solid in 55% yield (1.65 g, 4.4 mmol). mp 111-112° C. (EtOAc/n-heptane); TLC Rf (CH$_2$C2/MeOH: 99/1) 0.4; $^1$H NMR (CDCl$_3$, 400 MHz) δ ppm 1.20 (dd, J=6.5, 2.7 Hz, 6H, (CH$_3$)$_2$CH), 2.12 (td, J=18.1, 11.4, 9.0 Hz, 1H, CH$_2$CH$_2$CH), 2.38 (m, 1H, CH$_2$CH$_2$CH), 2.50 (td, J=17.5, 9.3, 1.8 Hz, 1H, CH$_2$CH$_2$CH), 2.86 (td, J=17.6, 11.4, 9.4 Hz, 1H, CH$_2$CH$_2$CH), 3.95 (m, 1H, (CH$_3$)$_2$CH), 4.48 (d, J=6.2 Hz, 2H, NHCH$_2$), 4.76 (dd, J=8.6, 1.4 Hz, 1H, CH$_2$CH$_2$CH), 7.18 (br t, J=6.2 Hz, 1H, NHCH$_2$), 7.20 (dd, J=8.3, 2.2 Hz, 1H, ArH), 7.30 (d, J=8.0 Hz, 1H, ArH), 7.37 (d, J=1.8 Hz, 1H, ArH), 8.33 (br t, J=5.7 Hz, 1H, NHCH(CH$_3$)$_2$); $^{13}$C NMR (CDCl$_3$, 100 MHz) δ ppm 21.1 (CH$_2$), 22.6 (CH$_3$), 22.7 (CH$_3$), 32.6 (CH$_2$), 41.1 (CH$_2$), 42.4 (CH), 59.0 (CH), 127.3 (CH), 129.3 (CH), 130.5 (CH), 133.9 (C), 134.1 (C), 152.3 (C), 170.4 (C), 177.2 (2 C); IR v (cm$^{-1}$): 3317, 1703, 1643, 1523, 1226, 817, 590; Anal. Calcd for C$_{16}$H$_{19}$Cl$_2$N$_3$O$_3$: C, 51.63; H, 5.14; N, 11.29. Found: C, 51.46; H, 5.55; N, 11.70%.

j) Synthesis of compound HEI_2538:

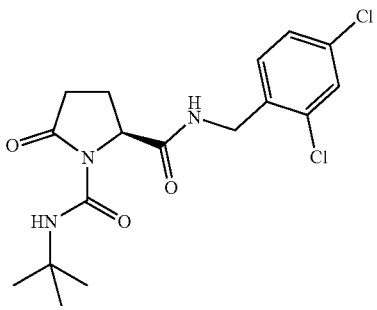 [SMILES: CC(C)(C)NC(=O)N1C(=O)CC[C@H]1C(=O)NCc1ccc(Cl)cc1Cl]

(S)—N$^1$-tert-Butyl-N$^2$-(2,4-dichlorobenzyl)-5-oxopyrrolidine-1,2-dicarboxamide (HEI_2538)

The general procedure was followed using (S)—N-(2,4-dichlorobenzyl)-5-oxo-pyrrolidine-2-carboxamide (1.97 g, 6.9 mmol), and tert-butyl isocyanate (0.75 g, 7.6 mmol). The desired product was purified on a silica column (EtOAc/n-heptane 3/7 to 1/0) to afford pure HEI_2538 as a white solid in 36% yield (0.95 g, 2.5 mmol). mp 99-101° C. (EtOAc/n-heptane); TLC Rf (CH$_2$C2/MeOH: 99/1) 0.7; $^1$H NMR (CDCl$_3$, 400 MHz) δ ppm 1.35 (s, 9H, C(CH$_3$)$_3$), 2.05-2.16 (m, 1H, CH$_2$CH$_2$CH), 2.36 (dd, J=11.9, 2.0 Hz, 1H, CH$_2$CH$_2$CH), 2.49 (ddd, J=17.6, 9.4, 2.0 Hz, 1H, CH$_2$CH$_2$CH), 2.93 (ddd, J=17.7, 11.4, 9.4 Hz, 1H, CH$_2$CH$_2$CH), 4.42 (dd, J=15.2, 5.9 Hz, 1H, NHCH$_2$), 4.53 (dd, J=15.7, 6.7 Hz, 1H, NHCH$_2$), 4.76 (dd, J=8.6, 1.6 Hz, 1H, CH$_2$CH$_2$CH), 7.18 (dd, J=8.2, 2.1 Hz, 1H, ArH), 7.20 (br s, 1H, NHCH$_2$), 7.29 (d, J=8.2 Hz, 1H, ArH, 7.36 (d, J=2.3 Hz, 1H, ArH, 8.48 (br s, 1H, NHC(CH$_3$)$_3$); $^{13}$C NMR (CDCl$_3$, 100 MHz) δ ppm 20.9 (CH$_2$), 28.7 (3 CH$_3$), 32.7 (CH$_2$), 41.0 (CH$_2$), 51.1 (C), 58.8 (CH), 127.2 (CH), 129.2 (CH), 130.3 (CH), 133.8 (C), 133.9 (C), 134.0 (C), 151.7 (C), 170.6 (C), 177.1 (C); IR v (cm$^{-1}$): 3280, 1717, 1689, 1656, 1547, 1267, 1191, 824, 657; Anal. Calcd for C$_{17}$H$_{21}$Cl$_2$N$_3$O$_3$: C, 52.86; H, 5.48; N, 10.88. Found: C, 52.63; H, 6.03; N, 10.91%.

k) Synthesis of compound HEI_2315:

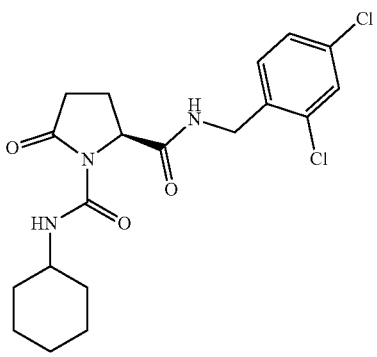 [SMILES: O=C(NCc1ccc(Cl)cc1Cl)[C@@H]1CCC(=O)N1C(=O)NC1CCCCC1]

(S)—N-Cyclohexyl-N$^2$-(2,4-dichlorobenzyl)-5-oxopyrrolidine-1,2-dicarboxamide (HEI_2315)

The general procedure was followed using (S)—N-(2,4-dichlorobenzyl)-5-oxo-pyrrolidine-2-carboxamide (2.00 g, 7.0 mmol), and cyclohexyl isocyanate (0.87 g, 7.0 mmol). The desired product crystallizes in MeCOH as a white powder, which was filtered to afford pure HEI_2315 in 82% yield (2.35 g, 5.7 mmol). mp 137-142° C. (MeOH); TLC Rf (CH$_2$C2/MeOH: 98/2) 0.5; $^1$H NMR (CDCl$_3$, 400 MHz) δ ppm 1.15-1.45 (m, 5H, cyclohex-H), 1.59 (m, 1H, cyclohex-H), 1.71 (m, 2H, cyclohex-H), 1.88 (m, 2H, cyclohex-H), 2.05-2.20 (m, 1H, cyclohex-H), 2.25-2.40 (m, 1H, CH$_2$CH$_2$CH), 2.42-2.56 (m, 1H, CH$_2$CH$_2$CH), 2.82-2.96 (m, 1H, CH$_2$CH$_2$CH), 3.62-3.66 (m, 1H, CH$_2$CH$_2$CH), 4.44 (dd, J=15.2, 5.6 Hz, 1H, NHCH$_2$), 4.51 (dd, J=15.2, 5.6 Hz, 1H, NHCH$_2$), 4.73-4.79 (m, 1H, CH$_2$CH$_2$CH), 7.19 (dd, J=8.4, 2.0 Hz, 1H, ArH), 7.29 (d, J=8.4 Hz, 1H, ArH, 7.30 (br s, 1H, NHCH$_2$), 7.37 (d, J=2.0 Hz, 1H, ArH), 8.42 (d, J=7.6 Hz, 1H, NHCH); $^{13}$C NMR (CDCl$_3$, 100 MHz) δ ppm 21.2 (CH$_2$), 24.5 (CH$_2$), 25.4 (CH$_2$), 32.5 (CH$_2$), 32.7 (CH$_2$), 32.8 (CH$_2$), 41.0 (CH$_2$), 49.0 (CH$_2$), 58.9 (2CH), 127.3 (CH), 129.3 (CH), 130.5 (CH), 133.9 (C), 134.0 (C), 134.1 (C), 152.2 (C), 170.5 (C), 177.2 (C); LC-MS (APCI$^+$) m/z: 412.0 (MH$^+$), tr 4.45 min; IR v (cm$^{-1}$): 3303, 2928, 2853, 1703, 1656, 1534, 1224; Anal. Calcd for C$_{19}$H$_{23}$Cl$_2$N$_3$O$_3$: C, 55.35; H, 5.62; N, 10.19. Found: C, 55.36; H, 6.14; N, 10.39%.

l) Synthesis of compound HEI_2329:

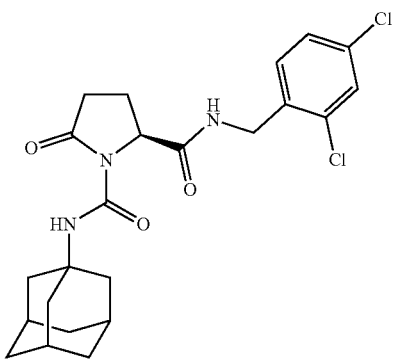 [SMILES: O=C(NCc1ccc(Cl)cc1Cl)[C@@H]1CCC(=O)N1C(=O)NC12CC3CC(CC(C3)C1)C2]

(S)—N$^1$-Adamantyl-N$^2$-(2,4-dichlorobenzyl)-5-oxopyrrolidine-1,2-dicarboxamide (HEI_2329)

The general procedure was followed using (S)—N-(2,4-dichlorobenzyl)-5-oxo-pyrrolidine-2-carboxamide (1.50 g, 5.2 mmol), and adamantyl isocyanate (0.93 g, 5.2 mmol). The desired product crystallizes in MeCOH as a white powder, which was filtered to afford pure HEI_2329 in 97% yield (2.34 g, 5.0 mmol). mp 85-87° C. (MeOH); TLC Rf (CH$_2$C2/MeOH: 98/2) 0.5; $^1$H NMR (CDCl$_3$, 400 MHz) δ ppm 1.64-1.70 (m, 6H, ADM-H), 1.95-1.99 (m, 6H, ADM-H), 2.00-2.16 (m, 4H, ADM-H and CH$_2$CH$_2$CH), 2.30-2.40 (m, 1H, CH$_2$CH$_2$CH), 2.42-2.54 (m, 1H, CH$_2$CH$_2$CH), 2.86-2.98 (m, 1H, CH$_2$CH$_2$CH), 4.45 (dd, J=15.2, 6.0 Hz, 1H, NHCH$_2$), 4.51 (dd, J=15.2, 6.0 Hz, 1H, NHCH$_2$), 4.76 (dd, J=8.8, 1.6 Hz, 1H, CH$_2$CH$_2$CH), 7.17 (dd, J=8.0, 2.0 Hz, 1H, ArH), 7.26 (t, J=6.0 Hz, 1H, NHCH$_2$), 7.28 (d, J=8.0 Hz, 1H, ArH), 7.36 (d, J=2.0 Hz, 1H, ArH), 8.39 (br s, 1H, NHCH); $^{13}$C NMR (CDCl$_3$, 100 MHz) δ ppm 21.1 (CH$_2$), 29.5 (2CH$_2$), 32.9 (CH$_2$), 36.4 (2CH$_2$), 41.1 (CH$_2$), 41.7 (2CH$_2$), 51.9 (CH), 59.0 (CH), 127.4 (CH), 129.4 (CH), 130.5 (CH), 134.0 (C), 134.1 (2C), 134.2 (C), 151.4 (C), 170.7 (C), 177.3 (C); LC-MS (APCI$^+$) m/z: 464.2 (MH$^+$), tr 4.80 min; IR v (cm$^{-1}$): 3289, 2906, 2848, 1715, 1661, 1538, 1222, 1048, 829; Anal. Calcd for $C_{23}H_{27}Cl_2N_3O_3$: C, 59.49; H, 5.86; N, 9.05. Found: C, 59.59; H, 6.26; N, 8.71%.

m) Synthesis of compound HEI_2339:

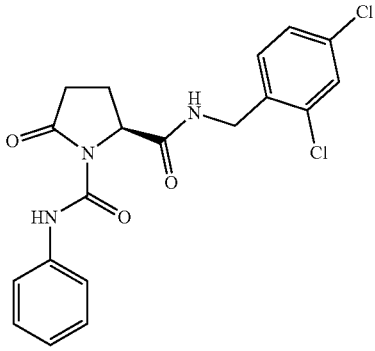 [SMILES: O=C(NCc1ccc(Cl)cc1Cl)[C@@H]1CCC(=O)N1C(=O)Nc1ccccc1]

(S)—$N^2$-(2,4-Dichlorobenzyl)-5-oxo-$N^1$-phenylpyrrolidine-1,2-dicarboxamide (HEI_2339)

The general procedure was followed using (S)—N-(2,4-dichlorobenzyl)-5-oxo-pyrrolidine-2-carboxamide (0.40 g, 1.4 mmol), and phenyl isocyanate (0.17 g, 1.4 mmol). The desired product crystallizes in MeCOH as a white powder, which was filtered to afford pure HEI_2339 in 76% yield (0.43 g, 1.1 mmol). mp 216-219° C. (MeOH); TLC Rf ($CH_2Cl_2$/MeOH: 96/4) 0.8; $^1$H NMR (DMSO-$d_6$, 400 MHz) δ ppm 1.85-1.95 (m, 1H, $CH_2CH_2CH$), 2.30-2.40 (m, 1H, $CH_2CH_2CH$), 2.58-2.79 (m, 2H, $CH_2CH_2CH$), 4.36 (m, 2H, $NHCH_2$), 4.80 (dd, J=9.2, 2.4 Hz, 1H, $CH_2CH_2CH$), 7.11 (t, J=7.2 Hz, 1H, ArH), 7.35 (t, J=7.2 Hz, 2H, ArH), 7.43-7.44 (m, 2H, ArH), 7.51 (d, J=7.2 Hz, 2H, ArH), 7.61-7.62 (m, 1H, ArH), 8.85 (t, J=5.6 Hz, 1H, $NHCH_2$), 10.51 (br s, 1H, NHAr); $^{13}$C NMR (DMSO-$d_6$, 100 MHz) δ ppm 21.4 ($CH_2$), 31.8 ($CH_2$), 40.0 ($CH_2$), 58.7 (CH), 119.5 (2 CH), 123.8 (CH), 127.3 (CH), 128.6 (CH), 129.1 (2 CH), 130.1 (CH), 132.3 (C), 132.9 (C), 135.2 (C), 137.3 (C), 149.4 (C), 171.2 (C), 177.8 (C); LC-MS (APCI$^+$) m/z: 408.1 (MH$^+$), tr 4.37 min; IR ν (cm$^{-1}$): 3276, 1718, 1644, 1543, 1217, 1054, 748; Anal. Calcd for $C_{19}H_{17}Cl_2N_3O_3$: C, 56.17; H, 4.22; N, 10.34. Found: C, 56.12; H, 3.96; N, 10.24%.

n) Synthesis of compound HEI_2761:

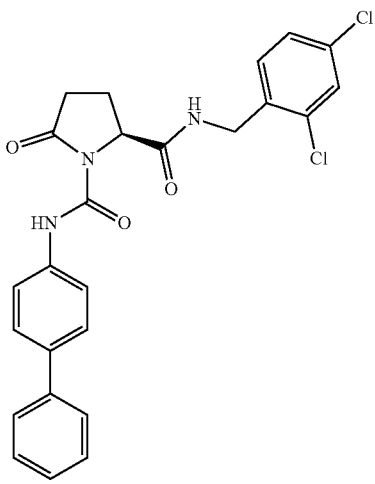 [SMILES: O=C(NCc1ccc(Cl)cc1Cl)[C@@H]1CCC(=O)N1C(=O)Nc1ccc(-c2ccccc2)cc1]

(S)—$N^1$-(Biphenyl-4-yl)-$N^2$-(2,4-dichlorobenzyl)-5-oxopyrrolidine-1,2-dicarboxamide (HEI_2761)

The general procedure was followed using (S)—N-(2,4-dichlorobenzyl)-5-oxo-pyrrolidine-2-carboxamide (1.00 g, 3.5 mmol), and biphenyl-4-yl isocyanate (0.75 g, 3.8 mmol). The desired product crystallizes in MeCOH as a white powder, which was filtered to afford pure HEI_2761 in 65% yield (1.09 g, 2.3 mmol). mp 191-200° C. (MeOH); TLC Rf ($CH_2Cl_2$/MeOH: 98/2)=0.9; $^1$H NMR (CDCl$_3$, 400 MHz) δ ppm 2.16-2.30 (m, 1H, $CH_2CH_2CH$), 2.34-2.43 (m, 1H, $CH_2CH_2CH$), 2.57-2.67 (m, 1H, $CH_2CH_2CH$), 2.99-3.12 (m, 1H, $CH_2CH_2CH$), 4.52 (dd, J=13.4, 6.7 Hz, 2H, $NCH_2Ar$), 4.84 (d, J=8.8 Hz, 1H, $CH_2CH_2CH$), 6.93 (s, 1H, NH), 7.21 (dd, J=8.2, 1.8 Hz, 1H, ArH), 7.30-7.38 (m, 3H, ArH), 7.44 (t, J=7.3 Hz, 2H, ArH), 7.52-7.61 (m, 6H, ArH), 10.60 (s, 1H, NH); $^{13}$C NMR (CDCl$_3$, 100 MHz) δ ppm 21.2 ($CH_2$), 29.7 ($CH_2$), 32.6 ($CH_2$), 41.2 ($CH_2$), 59.2 (CH), 126.8 (2 CH), 126.9 (CH), 127.4 (CH), 127.7 (2 CH), 128.8 (2 CH), 129.4 (2 CH), 130.8 (CH), 133.8 (C), 134.1 (C), 134.2 (C), 136.2 (C), 137.5 (C), 140.5 (C), 150.5 (C), 170.2 (C), 177.5 (C); IR ν (cm$^{-1}$): 3311, 3083, 1715, 1542, 1225, 764, 693; Anal. Calcd for $C_{25}H_{21}Cl_2N_3O_3$: C, 62.25; H, 4.39; N, 8.71. Found: C, 62.06; H, 4.39; N, 8.73%.

o) Synthesis of compound HEI_2314:

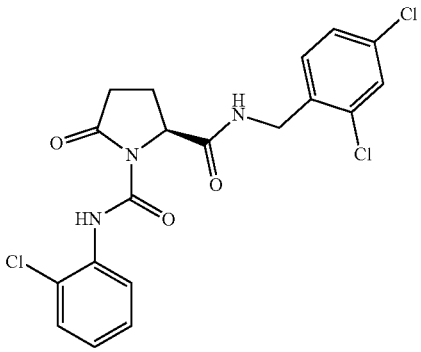

(S)—$N^1$-(2-Chlorophenyl)-$N^2$-(2,4-dichlorobenzyl)-5-oxopyrrolidine-1,2-dicarboxamide (HEI_2314)

The general procedure was followed using (S)—N-(2,4-dichlorobenzyl)-5-oxo-pyrrolidine-2-carboxamide (2.00 g, 7.0 mmol), and 2-chlorophenyl isocyanate (1.07 g, 7.0 mmol). The desired product crystallizes in MeCOH as a white powder, which was filtered to afford pure HEI_2314 in 90% yield (2.75 g, 6.2 mmol). mp 213-219° C. (MeOH); TLC Rf ($CH_2Cl_2$/MeOH: 98/2) 0.5; $^1$H NMR (CDCl$_3$, 400 MHz) δ ppm 2.18-2.36 (m, 2H, $CH_2CH_2CH$), 2.58-2.68 (m, 1H, $CH_2CH_2CH$), 2.95-3.06 (m, 1H, $CH_2CH_2CH$), 4.47 (dd, J=15.6, 5.6 Hz, 1H, $NHCH_2$), 4.54 (dd, J=15.6, 5.6 Hz, 1H, $NHCH_2$), 4.80 (dd, J=8.4, 2.4 Hz, 1H, $CH_2CH_2CH$), 7.06 (t, J=7.6 Hz, 1H, $NHCH_2$), 7.21 (dd, J=8.0, 2.0 Hz, 1H, ArH), 7.26 (t, J=7.6 Hz, 1H, ArH), 7.34 (d, J=8.4 Hz, 1H, ArH), 7.37 (d, J=2.0 Hz, 1H, ArH), 7.40 (m, 2H, ArH), 8.15 (d, J=8.0 Hz, 1H, ArH), 11.04 (br s, 1H, NHAr); $^{13}$C NMR (CDCl$_3$, 100 MHz) δ ppm 21.7 ($CH_2$), 32.3 ($CH_2$), 41.1 ($CH_2$), 59.2 (CH), 121.8 (CH), 124.0 (C), 125.0 (CH), 127.4 (CH), 127.5 (CH), 129.4 (CH), 129.5 (CH), 130.6 (CH), 133.9 (C), 134.0 (C), 134.1 (C), 134.4 (C), 150.3 (C), 171.0 (C), 177.6 (C); LC-MS (APCI$^+$) m/z: 442.0 (MH$^+$), tr 4.45 min; IR ν (cm$^{-1}$): 3271, 1713, 1643, 1597, 1545, 1222, 1054, 749; Anal. Calcd for $C_{19}H_{16}Cl_3N_3O_3$: C, 51.78; H, 3.66; N, 9.53. Found: C, 51.80; H, 3.73; N, 9.59%.

p) Synthesis of compound HEI_2760:

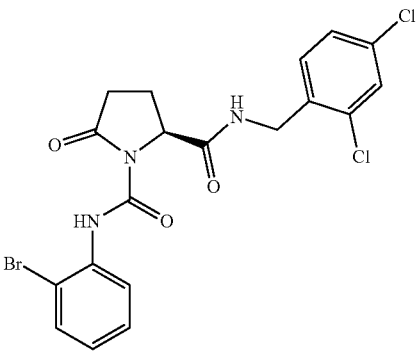 [SMILES: O=C(NCc1ccc(Cl)cc1Cl)[C@@H]1CCC(=O)N1C(=O)Nc1ccccc1Cl]

(S)—$N^1$-(2-Bromophenyl)-$N^2$-(2,4-dichlorobenzyl)-5-oxopyrrolidine-1,2-dicarboxamide (HEI_2760)

The general procedure was followed using (S)—N-(2,4-dichlorobenzyl)-5-oxo-pyrrolidine-2-carboxamide (1.00 g, 3.5 mmol), and 2-bromophenyl isocyanate (0.76 g, 3.8 mmol). The desired product crystallizes in MeCOH as a white powder, which was filtered to afford pure HEI_2760 in 56% yield (0.95 g, 2.0 mmol). mp 217-223° C. (MeOH); TLC Rf (CH$_2$Cl$_2$/MeOH: 95/5) 0.7; $^1$H NMR (CDCl$_3$, 400 MHz) δ ppm 2.18-2.43 (m, 2H, CH$_2$CH$_2$CH), 2.58-2.69 (m, 1H, CH$_2$CH$_2$CH), 2.98-3.11 (m, 1H, CH$_2$CH$_2$CH), 4.52 (dd, J=9.1, 5.7 Hz, 2H, NHCH$_2$), 4.81 (dd, J=9.2, 2.0 Hz, 1H, CH$_2$CH$_2$CH), 6.81 (br s, 1H, NHCH$_2$), 7.00 (ddd, J=7.9, 7.9, 1.6 Hz, 1H, ArH), 7.20 (dd, J=8.6, 2.4 Hz, 1H, ArH), 7.30-7.35 (m, 2H, ArH), 7.37 (d, J=2 Hz, 1H, ArH), 7.58 (dd, J=8.1, 1.8 Hz, 1H, ArH), 8.13 (dd, J=8.4, 2.1 Hz, 1H, ArH), 10.94 (s, 1H, NHAr); $^{13}$C NMR (CDCl$_3$, 100 MHz) δ ppm 21.3 (CH$_2$), 33.4 (CH$_2$), 41.3 (CH$_2$), 59.2 (CH), 111.3 (C), 122.3 (CH), 125.5 (CH), 127.4 (CH), 128.0 (CH), 129.4 (CH), 130.8 (CH), 132.7 (CH), 133.7 (C), 134.1 (C), 134.2 (C), 135.7 (C), 150.5 (C), 170.1 (C), 177.3 (C); IR v (cm$^{-1}$): 3268, 3202, 3063, 1714, 1644, 1541, 1218, 748; Anal. Calcd for $C_{19}H_{16}BrCl_2N_3O_3$: C, 47.04; H, 3.32; N, 8.66. Found: C, 47.03; H, 3.30; N, 8.66%.

q) Synthesis of compound HEI_2759:

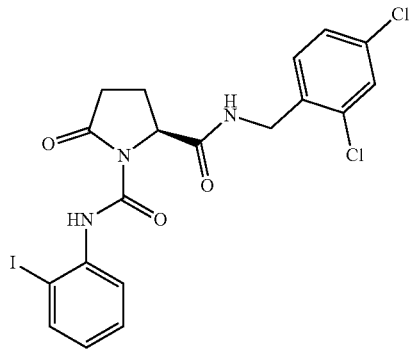 [SMILES: O=C(NCc1ccc(Cl)cc1Cl)[C@@H]1CCC(=O)N1C(=O)Nc1ccccc1I]

(S)—$N^2$-(2,4-Dichlorobenzyl)-$N^1$-(2-iodophenyl)-5-oxopyrrolidine-1,2-dicarboxamide (HEI_2759)

The general procedure was followed using (S)—N-(2,4-dichlorobenzyl)-5-oxo-pyrrolidine-2-carboxamide (1.00 g, 3.5 mmol), and 2-iodophenyl isocyanate (0.94 g, 3.8 mmol). The desired product crystallizes in MeCOH as a white powder, which was filtered to afford pure HEI_2759 in 58% yield (1.07 g, 2.0 mmol). mp 203-207° C. (MeOH); TLC Rf (CH$_2$Cl$_2$/MeOH: 95/5) 0.7; $^1$H NMR (CDCl$_3$, 400 MHz) δ ppm 2.18-2.31 (m, 1H, CH$_2$CH$_2$CH), 2.36-2.45 (m, 1H, CH$_2$CH$_2$CH), 2.59-2.68 (m, 1H, CH$_2$CH$_2$CH), 3.00-3.12 (m, 1H, CH$_2$CH$_2$CH), 4.52 (t, J=5.8 Hz, 2H, NHCH$_2$), 4.82 (dd, J=8.7, 1.7 Hz, 1H, CH$_2$CH$_2$CH), 6.82 (s, 1H, NHCH$_2$), 6.88 (td, J=7.6, 1.6 Hz, 1H, ArH), 7.21 (dd, J=8.1, 2.3 Hz, 1H, ArH), 7.30-7.39 (m, 3H, ArH), 7.84 (dd, J=8.1, 1.5 Hz, 1H, ArH), 7.96 (dd, J=8.3, 1.5 Hz, 1H, ArH), 10.68 (s, 1H, NHAr); $^{13}$C NMR (CDCl$_3$, 100 MHz) δ ppm 21.3 (CH$_2$), 32.5 (CH$_2$), 41.3 (CH$_2$), 59.2 (CH), 90.4 (C), 123.0 (CH), 126.4 (CH), 127.4 (CH), 128.8 (CH), 129.4 (CH), 130.8 (C), 133.8 (C), 134.1 (C), 134.2 (C), 138.5 (C), 139.5 (CH), 150.7 (C), 170.1 (C), 177.2 (C); IR v (cm$^{-1}$): 3265, 3207, 3076, 1714, 1644, 1533, 1217, 754; Anal. Calcd for $C_{19}H_{16}Cl_2IN_3O_3$: C, 42.88; H, 3.03; N, 7.90. Found: C, 42.82; H, 2.98; N, 8.04%.

r) Synthesis of compound HEI_2331

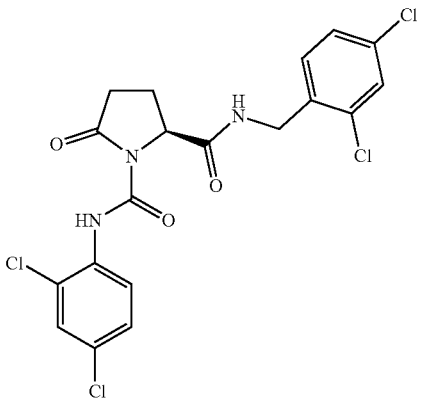 [SMILES: O=C(NCc1ccc(Cl)cc1Cl)[C@@H]1CCC(=O)N1C(=O)Nc1ccc(Cl)cc1Cl]

(S)—$N^2$-(2,4-Dichlorobenzyl)-$N^1$-(2,4-dichlorophenyl)-5-oxopyrrolidine-1,2-dicarboxamide (HEI_2331)

The general procedure was followed using (S)—N-(2,4-dichlorobenzyl)-5-oxo-pyrrolidine-2-carboxamide (1.00 g, 3.5 mmol), and 2,4-dichlorophenyl isocyanate (0.66 g, 3.5 mmol). The desired product crystallizes in MeCOH as a white powder, which was filtered to afford pure HEI_2331 in 87% yield (1.45 g, 3.1 mmol). mp 203-218° C. (MeOH); TLC Rf (CH$_2$Cl$_2$/MeOH: 98/2) 0.6; $^1$H NMR (DMSO-d$_6$, 400 MHz) δ ppm 1.86-1.96 (m, 1H, CH$_2$CH$_2$CH), 2.29-2.43 (m, 1H, CH$_2$CH$_2$CH), 2.60-2.81 (m, 2H, CH$_2$CH$_2$CH), 4.36 (m, 2H, CH$_2$CH$_2$CH and NHCH$_2$), 4.81 (dd, J=9.6, 2.8 Hz, 1H, NHCH$_2$), 7.41 (d, J=8.0 Hz, 1H, ArH), 7.43 (d, J=2.0 Hz, 1H, ArH), 7.47 (dd, J=9.2, 2.0 Hz, 1H, ArH), 7.62 (d, J=2.0 Hz, 1H, ArH), 7.74 (d, J=2.0 Hz, 1H, ArH), 8.24 (d, J=9.2 Hz, 1H, ArH), 8.88 (t, J=2.0 Hz, 1H, NHCH$_2$), 11.11 (br s, 1H, NHAr); $^{13}$C NMR (DMSO-d$_6$, 100 MHz) δ ppm 21.5 (CH$_2$), 31.7 (CH$_2$), 39.5 (CH$_2$), 58.7 (CH), 121.9 (CH), 123.0 (CH), 127.3 (CH), 127.7 (C), 128.1 (CH), 128.6 (CH), 128.8 (CH), 130.1 (C), 132.3 (C), 133.0 (C), 133.6 (C), 135.2 (C), 149.3 (C), 171.0 (C), 178.2 (C); LC-MS (APCI$^+$) m/z: 475.9 (MH$^+$), tr 4.78 min; IR v (cm$^{-1}$): 3263, 1716, 1656, 1582, 1537, 1224, 823; Anal. Calcd for $C_{19}H_{15}Cl_4N_3O_3$: C, 48.03; H, 3.18; N, 8.84. Found: C, 48.02; H, 3.17; N, 8.76%.

s) Synthesis of compound HEI_2333:

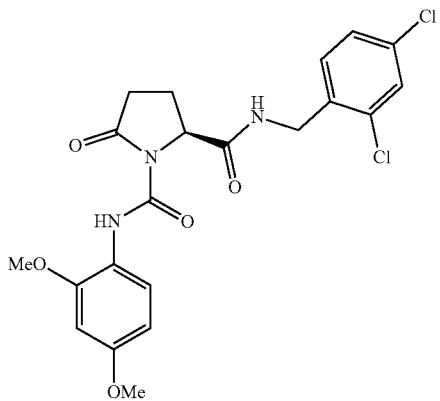 [SMILES: COc1ccc(NC(=O)N2C(=O)CC[C@H]2C(=O)NCc2ccc(Cl)cc2Cl)c(OC)c1]

(S)—N²-(2,4-dichlorobenzyl)-N¹-(2,4-dimethoxyphenyl)-5-oxopyrrolidine-1,2-dicarboxamide (HEI_2333)

The general procedure was followed using (S)—N-(2,4-dichlorobenzyl)-5-oxo-pyrrolidine-2-carboxamide (1.00 g, 3.5 mmol), and 2,4-dimethoxyphenyl isocyanate (0.62 g, 3.5 mmol). The desired product crystallizes in MeCOH as a white powder, which was filtered to afford pure HEI_2333 in 83% yield (1.35 g, 2.9 mmol). mp 203-205° C. (MeOH); TLC Rf (CH$_2$Cl$_2$/MeOH: 98/2) 0.6; $^1$H NMR (CDCl$_3$, 400 MHz) δ ppm 2.15-2.23 (m, 1H, CH$_2$CH$_2$CH), 2.35-2.43 (m, 1H, CH$_2$CH$_2$CH), 2.55-2.63 (m, 1H, CH$_2$CH$_2$CH), 2.92-3.05 (m, 1H, CH$_2$CH$_2$CH), 3.80 (s, 3H, OCH$_3$), 3.88 (s, 3H, OCH$_3$), 4.45 (dd, J=15.2, 6.0 Hz, 1H, NHCH$_2$), 4.54 (dd, J=15.2, 6.0 Hz, 1H, NHCH$_2$), 4.84 (dd, J=8.8, 1.6 Hz, 1H, CH$_2$CH$_2$CH), 6.44 (dd, J=8.8, 2.8 Hz, 1H, ArH), 6.50 (d, J=2.8 Hz, 1H, ArH), 7.10 (t, J=6.0 Hz, 1H, NHCH$_2$), 7.17 (dd, J=8.0, 2.0 Hz, 1H, ArH), 7.31 (d, J=8.0 Hz, 1H, ArH), 7.34 (d, J=2.0 Hz, 1H, ArH), 7.93 (d, J=8.8 Hz, 1H, ArH), 10.71 (br s, 1H, NHAr); $^{13}$C NMR (CDCl$_3$, 100 MHz) δ ppm 21.4 (CH$_2$), 32.7 (CH$_2$), 41.3 (CH$_2$), 55.7 (CH), 56.0 (CH$_3$), 59.2 (CH$_3$), 98.9 (CH), 103.9 (CH), 120.3 (CH), 121.1 (CH), 127.5 (CH), 129.5 (C), 130.7 (CH), 134.0 (C), 134.1 (C), 134.2 (C), 150.4 (C), 150.5 (C), 157.0 (C), 170.5 (C), 177.2 (C); LC-MS (APCI$^+$) m/z: 466.0 (MH$^+$), tr 4.33 min; IR v (cm$^{-1}$): 3294, 1712, 1657, 1547, 1299, 1205, 1033, 818; Anal. Calcd for C$_{21}$H$_{21}$Cl$_2$N$_3$O$_5$: C, 54.09; H, 4.54; N, 9.01. Found: C, 53.91; H, 3.81; N, 8.91%.

t) Synthesis of compound HEI_2338:

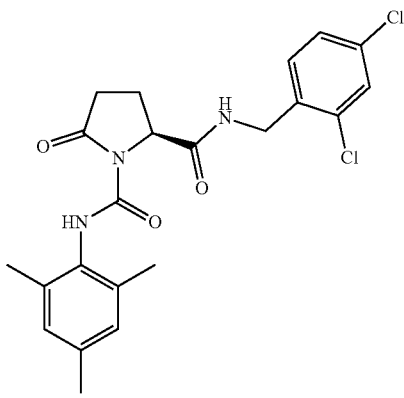 [SMILES: Cc1cc(C)c(NC(=O)N2C(=O)CC[C@H]2C(=O)NCc2ccc(Cl)cc2Cl)c(C)c1]

(S)—N²-(2,4-Dichlorobenzyl)-5-oxo-N¹-(2,4,6-trimethylphenyl)pyrrolidine-1,2-dicarboxamide (HEI_2338)

The general procedure was followed using (S)—N-(2,4-dichlorobenzyl)-5-oxo-pyrrolidine-2-carboxamide (0.70 g, 2.4 mmol), and 2,4,6-trimethylphenyl isocyanate (0.39 g, 2.4 mmol). The desired product crystallizes in MeCOH as a white powder, which was filtered to afford pure HEI_2338 in 55% yield (0.60 g, 1.3 mmol). mp 156-157° C. (MeOH); TLC Rf (CH$_2$Cl$_2$/MeOH: 95/5) 0.8; $^1$H NMR (CDCl$_3$, 400 MHz) ppm 2.14 (s, 6H, CCH$_3$), 2.18-2.24 (m, 1H, CH$_2$CH$_2$CH), 2.27 (s, 3H, CCH$_3$), 2.38-2.45 (m, 1H, CH$_2$CH$_2$CH), 2.55-2.65 (m, 1H, CH$_2$CH$_2$CH), 2.98-3.10 (m, 1H, CH$_2$CH$_2$CH), 4.42 (dd, J=6.0, 2.0 Hz, 2H, NHCH$_2$), 4.83 (dd, J=8.4, 1.6 Hz, 1H, CH$_2$CH$_2$CH), 6.89 (s, 2H, ArH), 7.09-7.15 (m, 2H, NHCH$_2$ and ArH), 7.23 (d, J=8.8 Hz, 1H, ArH), 7.34 (d, J=2.4 Hz, 1H, ArH), 9.74 (br s, 1H, NHAr); $^{13}$C NMR (CDCl$_3$, 100 MHz) δ ppm 18.4 (2 CH$_3$), 21.1 (CH$_3$), 21.3 (CH$_2$), 32.7 (CH$_2$), 41.1 (CH$_2$), 59.2 (CH), 127.4 (CH), 129.1 (2 CH), 129.4 (C), 130.4 (C), 130.5 (CH), 134.0 (CH), 134.1 (C), 134.2 (C), 135.1 (2 C), 137.3 (C), 151.7 (C), 170.5 (C), 177.8 (C); LC-MS (APCI$^+$) m/z: 448.1 (MH$^+$), tr 4.57 min; IR v (cm$^{-1}$): 3275, 1714, 1658, 1514, 1358, 1242, 1219, 1033, 826; Anal. Calcd for C$_{22}$H$_{23}$Cl$_2$N$_3$O$_3$: C, 58.94; H, 5.17; N, 9.37. Found: C, 58.80; H, 5.26; N, 9.25%.

u) Synthesis of compound HEI_2337:

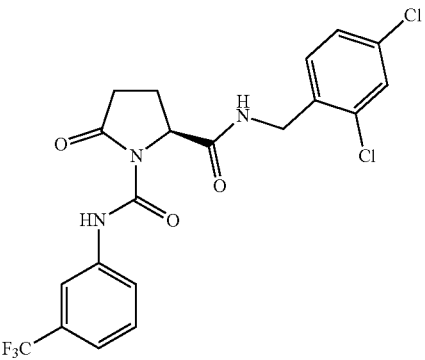 [SMILES: O=C(NCc1ccc(Cl)cc1Cl)[C@@H]1CCC(=O)N1C(=O)Nc1cccc(C(F)(F)F)c1]

(S)—N²-(2,4-Dichlorobenzyl)-5-oxo-N¹-[(3-trifluoromethyl)phenyl]pyrrolidine-1,2-dicarboxamide (HEI_2337)

The general procedure was followed using (S)—N-(2,4-dichlorobenzyl)-5-oxo-pyrrolidine-2-carboxamide (1.00 g, 3.5 mmol), and 3-trifluoromethylphenyl isocyanate (0.65 g, 3.5 mmol). The desired product crystallizes in MeCOH as a white powder, which was filtered to afford pure HEI_2337 in 73% yield (1.20 g, 2.5 mmol). mp 171-174° C. (MeOH); TLC Rf (CH$_2$Cl$_2$/MeOH: 98/2) 0.6; $^1$H NMR (DMSO-d$_6$, 400 MHz) δ ppm 1.90-1.98 (m, 1H, CH$_2$CH$_2$CH), 2.30-2.42 (m, 1H, CH$_2$CH$_2$CH), 2.60-2.80 (m, 2H, CH$_2$CH$_2$CH), 4.35-4.39 (m, 2H, CH$_2$CH$_2$CH and NHCH$_2$), 4.81 (dd, J=9.6, 2.8 Hz, 1H, NHCH$_2$), 7.38 (dd, J=8.8, 2.4 Hz, 1H, ArH), 7.45 (d, J=8.4 Hz, 1H, ArH), 7.47 (d, J=8.4 Hz, 1H, ArH), 7.59 (t, J=8.4 Hz, 1H, ArH), 7.61 (d, J=2.4 Hz, 1H, ArH), 7.72 (d, J=8.8 Hz, 1H, ArH), 8.07 (s, 1H, ArH), 8.88 (t, J=6.0 Hz, 1H, NHCH$_2$), 10.68 (br s, 1H, NHAr); $^{13}$C NMR (DMSO-d$_6$, 100 MHz) δ ppm 21.8 (CH$_2$), 32.2 (CH$_2$), 40.6 (CH$_2$), 59.2 (CH), 116.3 (q, J=3.8 Hz, CH), 127.0 (m, CH), 124.0 (CH), 124.3 (q, J=272.0 Hz, CF$_3$), 127.6 (CH), 129.0 (CH), 130.0 (q, J=32 Hz, C), 130.2 (CH), 130.6 (CH), 132.8 (C), 133.4 (C), 135.7 (C), 138.6 (C), 150.1 (C), 171.5 (C), 178.2 (C); $^{19}$F NMR (CDCl$_3$, 376 MHz) δ ppm −61.4 (CF$_3$); LC-MS (APCI$^+$) m/z: 474.0 (MH$^+$), tr 4.58 min; IR ν (cm$^{-1}$): 3298, 1727, 1658, 1556, 1450, 1333, 1251, 1112, 831; Anal. Calcd for C$_{20}$H$_{16}$Cl$_2$F$_3$N$_3$O$_3$: C, 50.65; H, 3.40; N, 8.86. Found: C, 50.34; H, 3.30; N, 8.74%.

v) Synthesis of compound HEI_2328:

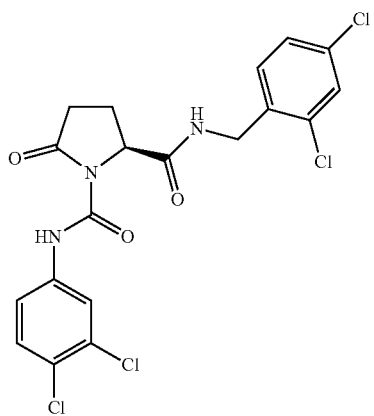 [SMILES: O=C(NCc1ccc(Cl)cc1Cl)[C@@H]1CCC(=O)N1C(=O)Nc1ccc(Cl)c(Cl)c1]

(S)—N$^2$-(2,4-Dichlorobenzyl)-N$^1$-(3,4-dichlorophenyl)-5-oxopyrrolidine-1,2-dicarboxamide (HEI_2328)

The general procedure was followed using (S)—N-(2,4-dichlorobenzyl)-5-oxo-pyrrolidine-2-carboxamide (1.50 g, 5.2 mmol), and 3,4-dichlorophenyl isocyanate (0.98 g, 5.2 mmol). The desired product crystallizes in MeCOH as a white powder, which was filtered to afford pure HEI_2328 in 81% yield (2.00 g, 4.2 mmol). mp 220-224° C. (MeOH); TLC Rf (CH$_2$C2/MeOH: 98/2) 0.7; $^1$H NMR (DMSO-d$_6$, 400 MHz) δ ppm 1.84-1.97 (m, 1H, CH$_2$CH$_2$CH), 2.25-2.40 (m, 1H, CH$_2$CH$_2$CH), 2.60-2.80 (m, 2H, CH$_2$CH$_2$CH), 4.36 (s, 2H, NHCH$_2$), 4.79 (d, J=8.5 Hz, 1H, CH$_2$CH$_2$CH), 7.38-7.65 (m, 5H, NHCH$_2$ and ArH), 7.94 (s, 1H, ArH), 8.86 (s, 1H, ArH), 10.59 (br s, 1H, NHAr); $^{13}$C NMR (DMSO-d$_6$, 100 MHz) δ ppm 21.5 (CH$_2$), 31.7 (CH$_2$), 39.5 (CH$_2$), 58.7 (CH), 120.0 (CH), 121.1 (CH), 125.4 (C), 127.3 (CH), 128.6 (CH), 130.2 (CH), 130.8 (CH), 131.2 (C), 132.3 (C), 133.0 (C), 135.2 (C), 137.5 (C), 149.4 (C), 171.0 (C), 177.7 (C); LC-MS (APCI$^+$) m/z: 474.0 (MH$^+$), tr 4.67 min; IR ν (cm$^{-1}$): 3270, 1718, 1644, 1598, 1547, 1476, 1218, 1134, 818; Anal. Calcd for C$_{19}$H$_{15}$Cl$_4$N$_3$O$_3$: C, 48.03; H, 3.18; N, 8.84. Found: C, 47.75; H, 3.03; N, 8.71%.

w) Synthesis of compound HEI_2336:

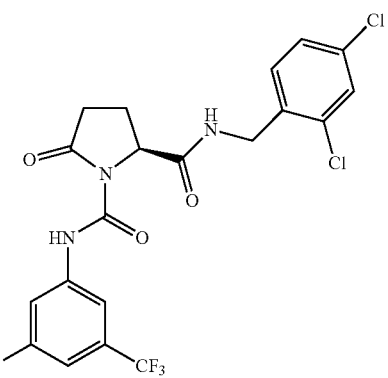

(S)—N$^1$-[3,5-Bis(trifluoromethyl)phenyl]-N$^2$-(2,4-dichlorobenzyl)-5-oxopyrrolidine-1,2-dicarboxamide (HEI_2336)

The general procedure was followed using (S)—N-(2,4-dichlorobenzyl)-5-oxo-pyrrolidine-2-carboxamide (1.00 g, 3.5 mmol), and 3,5-bis(trifluoromethyl)phenyl isocyanate (0.89 g, 3.5 mmol). The desired product crystallizes in MeCOH as a white powder, which was filtered to afford pure HEI_2336 in 64% yield (1.20 g, 2.2 mmol). TLC Rf (CH$_2$Cl$_2$/MeOH: 98/2) 0.6; mp 223-225° C. (MeOH); $^1$H NMR (CDCl$_3$, 400 MHz) δ ppm 2.23-2.36 (m, 2H, CH$_2$CH$_2$CH), 2.60-2.70 (m, 1H, CH$_2$CH$_2$CH), 2.98-3.12 (m, 1H, CH$_2$CH$_2$CH), 4.49 (dd, J=15.2, 5.6 Hz, 1H, NHCH$_2$), 4.57 (dd, J=15.2, 5.6 Hz, 1H, NHCH$_2$), 4.78 (dd, J=7.2, 2.8 Hz, 1H, CH$_2$CH$_2$CH), 6.66 (t, J=5.6 Hz, 1H, NHCH$_2$), 7.20 (dd, J=8.4, 2.4 Hz, 1H, ArH), 7.34 (d, J=8.4 Hz, 1H, ArH), 7.36 (d, J=2.4 Hz, 1H, ArH), 7.62 (s, 1H, ArH), 7.99 (s, 2H, ArH), 10.91 (br s, 1H, NHAr); $^{13}$C NMR (CDCl$_3$, 100 MHz) δ ppm 21.4 (CH$_2$), 32.4 (CH$_2$), 41.4 (CH$_2$), 59.2 (CH), 117.7 (q, J=3.9 Hz, CH), 119.8 (m, 2CH), 123.0 (q, J=272.0 Hz, 2 CF$_3$), 127.5 (CH), 129.5 (CH), 130.9 (CH), 132.4 (q, J=32.0 Hz, 2C), 133.5 (C), 134.2 (C), 134.4 (C), 138.6 (C), 150.2 (C), 170.0 (C), 177.8 (C); $^{19}$F NMR (CDCl$_3$, 100 MHz) δ ppm −63.1 (CF$_3$); LC-MS (APCI$^+$) m/z: 543.8 (MH$^+$), tr 5.05 min; IR ν (cm$^{-1}$): 3290, 3089, 1725, 1656, 1561, 1284, 1172, 1128, 1042, 890; Anal. Calcd for C$_{21}$H$_{15}$Cl$_2$F$_6$N$_3$O$_3$: C, 46.51; H, 2.79; N, 7.75. Found: C, 46.49; H, 2.61; N, 7.69%.

x) Synthesis of compound HEI_2278:

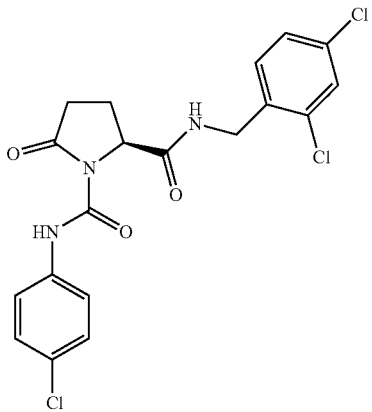 [SMILES: O=C(NCc1ccc(Cl)cc1Cl)[C@@H]1CCC(=O)N1C(=O)Nc1ccc(Cl)cc1]

(S)—N¹-(4-Chlorophenyl)-N²-(2,4-dichlorobenzyl)-5-oxopyrrolidine-1,2-dicarboxamide (HEI_2278)

The general procedure was followed using (S)—N-(2,4-dichlorobenzyl)-5-oxo-pyrrolidine-2-carboxamide (1.00 g, 3.5 mmol), and 4-chlorophenyl isocyanate (0.54 g, 3.5 mmol). The desired product was purified on a silica column (CH$_2$Cl$_2$/MeOH I/O to 99/1) to afford pure HEI_2278 as a white solid in 68% yield (1.05 g, 2.4 mmol). mp 188-191° C. (CH$_2$Cl$_2$/MeOH); TLC Rf (EtOAc/n-Heptane: 4/6) 0.3; $^1$H NMR (DMSO-d$_6$, 400 MHz) δ ppm 1.85-1.95 (m, 1H, CH$_2$CH$_2$CH), 2.30-2.40 (m, 1H, CH$_2$CH$_2$CH), 2.58-2.78 (m, 2H, CH$_2$CH$_2$CH), 4.35 (m, 2H, CH$_2$CH$_2$CH and NHCH$_2$), 4.79 (dd, J=9.2, 6.0 Hz, 1H, NHCH$_2$), 7.40 (d, J=8.8 Hz, 2H, ArH), 7.42 (m, 2H, ArH), 7.57 (d, J=8.8 Hz, 2H, ArH), 7.62 (d, J=1.5 Hz, 1H, ArH), 8.85 (t, J=6.0 Hz, 1H, NHCH$_2$), 10.54 (br s, 1H, NHAr); $^{13}$C NMR (DMSO-d$_6$, 100 MHz) δ ppm 21.4 (CH$_2$), 31.8 (CH$_2$), 38.3 (CH$_2$), 58.7 (CH), 121.2 (2 CH), 127.3 (CH), 127.5 (C), 128.6 (CH), 128.9 (2 CH), 130.1 (CH), 132.3 (C), 132.9 (C), 135.2 (C), 136.3 (C), 149.4 (C), 171.1 (C), 177.8 (C); LC-MS (APCI$^+$) m/z: 439.9 (MH$^+$), tr 4.50 min; IR ν (cm$^{-1}$): 3283, 2922, 1712, 1649, 1600, 1545, 1388, 1224, 1051, 828; Anal. Calcd for C$_{19}$H$_{16}$Cl$_3$N$_3$O$_3$: C, 51.78; H, 3.66; N, 9.53. Found: C, 52.02; H, 3.92; N, 9.38%.

y) Synthesis of compound HEI_2817:

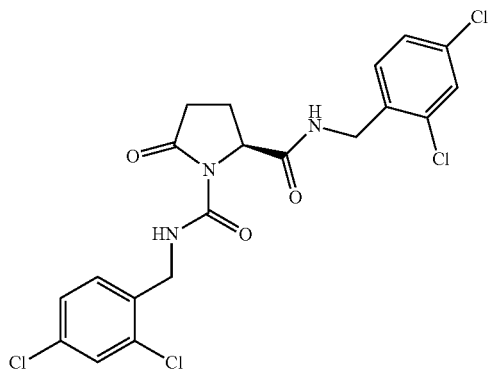 [SMILES: O=C(NCc1ccc(Cl)cc1Cl)[C@@H]1CCC(=O)N1C(=O)NCc1ccc(Cl)cc1Cl]

(S)—N¹,N²-Bis(2,4-dichlorobenzyl)-5-oxopyrrolidine-1,2-dicarboxamide (HEI_2817)

The general procedure was followed using (S)—N-(2,4-dichlorobenzyl)-5-oxo-pyrrolidine-2-carboxamide (1.00 g, 3.5 mmol), and 2,4-dichlorobenzyl isocyanate (0.77 g, 3.8 mmol). The desired product crystallizes in MeCOH as a white powder, which was filtered to afford pure HEI_2817 in 78% yield (1.31 g, 2.7 mmol). TLC Rf (CH$_2$Cl$_2$/MeOH: 95/5) 0.7; mp 224-226° C. (MeOH); $^1$H NMR (DMSO-d$_6$, 400 MHz) δ ppm 1.81-1.91 (m, 1H, CH$_2$CH$_2$CH), 2.24-2.37 (m, 1H, CH$_2$CH$_2$CH), 2.43-2.72 (m, 2H, CH$_2$CH$_2$CH), 4.31 (d, J=5.7 Hz, 2H, NCH$_2$), 4.44 (d, J=5.7 Hz, 2H, NCH$_2$), 4.69 (dd, J=9.2, 2.6 Hz, 1H, CH$_2$CH$_2$CH), 7.24-7.43 (m, 4H, ArH), 7.61 (dd, J=7.4, 2.0 Hz, 2H, ArH), 8.77 (t, J=6.3 Hz, 1H, NH), 8.86 (t, J=6.3 Hz, 1H, NH); $^{13}$C NMR (DMSO-d$_6$, 100 MHz) δ ppm 22.0 (CH$_2$), 32.1 (CH$_2$), 40.6 (CH$_2$), 40.9 (CH$_2$), 59.0 (CH), 127.6 (CH), 127.7 (CH), 128.9 (CH), 129.0 (CH), 130.4 (CH), 130.6 (CH), 132.6 (CH), 132.8 (CH), 133.2 (C), 133.3 (C), 135.7 (C), 135.8 (C), 152.5 (C), 171.8 (C), 177.6 (C); IR ν (cm$^{-1}$): 3251, 3089, 1709, 1653, 1538, 1239; Anal. Calcd for C$_{20}$H$_{17}$Cl$_4$N$_3$O$_3$: C, 49.11; H, 3.50; N, 8.59. Found: C, 49.12; H, 3.50; N, 8.60%.

z) Synthesis of compound HEI_2820:

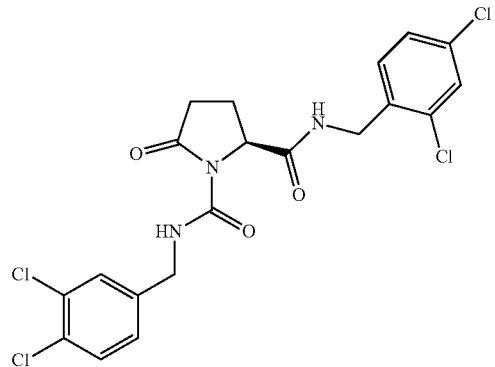 [SMILES: O=C(NCc1ccc(Cl)cc1Cl)[C@@H]1CCC(=O)N1C(=O)NCc1ccc(Cl)c(Cl)c1]

(S)—N²-(2,4-Dichlorobenzyl)-N¹-(3,4-dichlorobenzyl)-5-oxopyrrolidine-1,2-dicarboxamide (HEI_2820)

The general procedure was followed using (S)—N-(2,4-dichlorobenzyl)-5-oxo-pyrrolidine-2-carboxamide (1.00 g, 3.5 mmol), and 3,4-dichlorobenzyl isocyanate (0.67 g, 3.3 mmol). The desired product crystallizes in MeCOH as a white powder, which was filtered to afford pure HEI_2820 in 32% yield (0.54 g, 1.1 mmol). mp 201-204° C. (MeOH); TLC Rf (CH$_2$Cl$_2$/MeOH: 95/5) 0.7; $^1$H NMR (CDCl$_3$, 400 MHz) δ ppm 2.12-2.25 (m, 1H, CH$_2$CH$_2$CH), 2.31-2.41 (m, 1H, CH$_2$CH$_2$CH), 2.49-2.59 (m, 1H, CH$_2$CH$_2$CH), 2.89-3.01 (m, 1H, CH$_2$CH$_2$CH), 4.33-4.57 (m, 4H, NCONHCH$_2$, CHCONHCH$_2$, CH$_2$CH$_2$CH), 4.74 (d, J=9.3 Hz, 1H, CHCONHCH$_2$), 6.86 (s, 1H, CHCONHCH$_2$), 7.11 (d, J=9.3 Hz, 1H, ArH), 7.16-7.22 (m, 1H, ArH), 7.27-7.34 (m, 1H, ArH, 7.36-7.42 (m, 3H, ArH), 8.88 (s, 1H, NCONHCH$_2$); $^{13}$C NMR (CDCl$_3$, 100 MHz) δ ppm 21.3 (CH$_2$), 32.4 (CH$_2$), 41.2 (CH$_2$), 42.8 (CH$_2$), 59.1 (CH), 126.8 (CH), 127.4 (CH), 129.3 (CH), 129.4 (CH), 130.6 (CH), 130.7 (CH), 132.8 (C), 133.7 (C), 134.1 (C), 134.1 (C), 138.2 (C), 153.3 (C), 170.2 (C), 177.4 (C), 184.0 (C); IR ν (cm$^{-1}$): 3320, 3274, 3058, 2943, 1707, 1650, 1542, 1243, 816; Anal. Calcd for C$_{20}$H$_{17}$Cl$_4$N$_3$O$_3$: C, 49.11; H, 3.50; N, 8.59. Found: C, 49.14; H, 3.58; N, 8.53%.

a') Synthesis of compound HEI_2548:

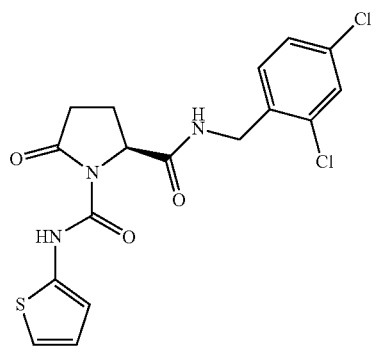 [SMILES: O=C(NCc1ccc(Cl)cc1Cl)[C@@H]1CCC(=O)N1C(=O)Nc1cccs1]

$N^2$-(2,4-Dichlorobenzyl)-5-oxo-$N^1$-(thiophen-2-yl)pyrrolidine-1,2-dicarboxamide (HEI_2548)

The general procedure was followed using (S)—N-(2,4-dichlorobenzyl)-5-oxo-pyrrolidine-2-carboxamide (0.83 g, 2.9 mmol), and thiophen-2-yl isocyanate (0.40 g, 3.2 mmol). The desired product crystallizes in MeCOH as a white powder, which was filtered to afford pure HEI_2548 in 26% yield (0.31 g, 0.8 mmol). mp 141-143° C. (MeOH); TLC Rf (CH$_2$Cl$_2$/MeOH: 99/1) 0.5; $^1$H NMR (CDCl$_3$, 400 MHz) δ ppm 2.20-2.31 (m, 1H, CH$_2$CH$_2$CH), 2.35-2.41 (m, 1H, CH$_2$CH$_2$CH), 2.62 (td, J=18.1, 9.4 Hz, 1H, CH$_2$CH$_2$CH), 3.06 (td, J=17.6, 9.4 Hz, 1H, CH$_2$CH$_2$CH), 4.50-4.55 (m, 2H, NHCH$_2$), 4.85 (dd, J=9.0, 1.6 Hz, 1H, CH$_2$CH$_2$CH), 6.73 (dd, J=3.9, 1.5 Hz, 1H, ArH), 6.89 (dd, J=5.5, 3.5 Hz, 1H, ArH), 6.92 (dd, J=5.5, 1.5 Hz, 1H, ArH), 6.95 (br t, J=4.6 Hz, 1H, NHCH$_2$), 7.21 (dd, J=8.2, 2.0 Hz, 1H, ArH, 7.34 (d, J=8.3 Hz, 1H, ArH, 7.37 (d, J=1.9 Hz, 1H, ArH, 11.00 (s, 1H, NHAr); $^{13}$C NMR (CDCl$_3$, 100 MHz) δ ppm 21.6 (CH$_2$), 32.2 (CH$_2$), 41.2 (CH$_2$), 59.1 (CH), 113.4 (CH), 118.4 (CH), 124.5 (CH), 127.3 (CH), 129.3 (CH), 130.6 (CH), 133.6 (C), 134.0 (C), 134.1 (C), 137.9 (C), 149.6 (C), 170.2 (C), 177.5 (C); IR v (cm$^{-1}$): 3291, 1712, 1660, 1556, 1510, 1343, 1245, 1218, 815, 689; Anal. Calcd for C$_{17}$H$_{15}$Cl$_2$N$_3$O$_3$S: C, 49.52; H, 3.67; N, 10.19; S, 7.78. Found: C, 49.23; H, 3.80; N, 10.00; S, 7.03%.

b') Synthesis of compound HEI_3090:

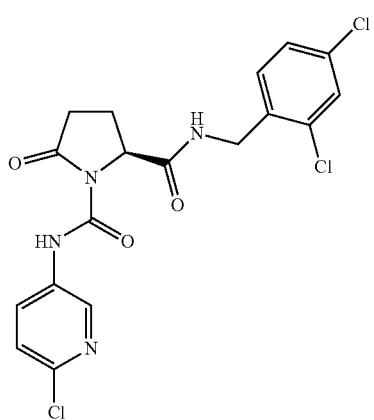 [SMILES: O=C(NCc1ccc(Cl)cc1Cl)[C@@H]1CCC(=O)N1C(=O)Nc1ccc(Cl)nc1]

(S)—$N^1$-(6-Chloropyridin-3-yl)-$N^2$-(2,4-dichlorobenzyl)-5-oxopyrrolidine-1,2-dicarboxamide (HEI_3090)

The general procedure was followed using (S)—N-(2,4-dichlorobenzyl)-5-oxo-pyrrolidine-2-carboxamide (1.86 g, 6.5 mmol), and 6-chloropyridin-3-yl isocyanate (1.00 g, 6.5 mmol). The desired product was purified on a silica column (CH$_2$Cl$_2$/MeOH I/O to 9/1) to afford pure HEI_3090 as a white solid in 11% yield (0.30 g, 0.7 mmol). mp 187-190° C. (CH$_2$Cl$_2$/MeOH); TLC Rf (CH$_2$Cl$_2$/MeOH: 95/5) 0.8; $^1$H NMR (CDCl$_3$, 400 MHz) δ ppm 2.12-2.37 (m, 2H, CH$_2$CH$_2$CH), 2.59-2.68 (m, 1H, CH$_2$CH$_2$CH), 2.99-3.10 (m, 1H, CH$_2$CH$_2$CH), 4.49 (dd, J=15.2, 6.2 Hz, 1H, NHCH$_2$), 4.55 (dd, J=15.2, 6.2 Hz, 1H, NHCH$_2$), 4.77 (dd, J=8.7, 2.1 Hz, 1H, CH$_2$CH$_2$CH), 6.65 (br t, J=6.2 Hz, 1H, NHCH$_2$), 7.22 (dd, J=8.1, 2.0 Hz, 1H, ArH), 7.29 (d, J=8.6 Hz, 1H, ArH), 7.33 (d, J=8.1 Hz, 1H, ArH), 7.38 (d, J=2.0 Hz, 1H, ArH), 7.92 (dd, J=8.6, 2.5 Hz, 1H, ArH), 8.49 (d, J=2.5 Hz, 1H, ArH), 10.66 (s, 1H, NHAr); $^{13}$C NMR (CDCl$_3$, 100 MHz) δ ppm 21.4 (CH$_2$), 32.4 (CH$_2$), 41.4 (CH$_2$), 59.2 (CH), 124.3 (CH), 127.5 (CH), 129.5 (CH), 130.2 (CH), 130.9 (CH), 133.1 (C), 133.6 (2 C), 134.2 (C), 141.3 (CH), 146.2 (C), 150.3 (C), 170.0 (C), 177.7 (C); IR v (cm$^{-1}$): 3271, 3095, 2935, 1721, 1655, 1594, 1542, 1464, 1217, 1104.

N,N'-Bis(6-chloropyridin-3-yl)urea (HEI_3091)

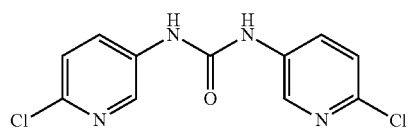 [SMILES: O=C(Nc1ccc(Cl)nc1)Nc1ccc(Cl)nc1]

It was isolated from previous experiment during column chromatography to afford pure HEI_3091 as a white solid in 54% yield (0.50 g, 1.8 mmol). mp>260° C.; TLC Rf (CH$_2$Cl$_2$/MeOH: 95/5) 0.4; $^1$H NMR (CDCl$_3$, 400 MHz) ppm 7.45 (d, J=8.7 Hz, 2H, ArH), 7.99 (dd, J=8.7, 3.1 Hz, 2H, ArH), 8.49 (d, J=3.1 Hz, 2H, ArH), 9.21 (s, 2H, NH); $^{13}$C NMR (CDCl$_3$, 100 MHz) ppm 124.0 (2 CH), 129.2 (2 CH), 135.6 (2 C), 139.8 (2 CH), 142.6 (2 C), 152.3 (C); IR v (cm$^{-1}$): 3267, 3180, 3095, 3052, 1711, 1531, 1465, 1285, 1208, 1107, 833.

c') Synthesis of compound HEI_2773:

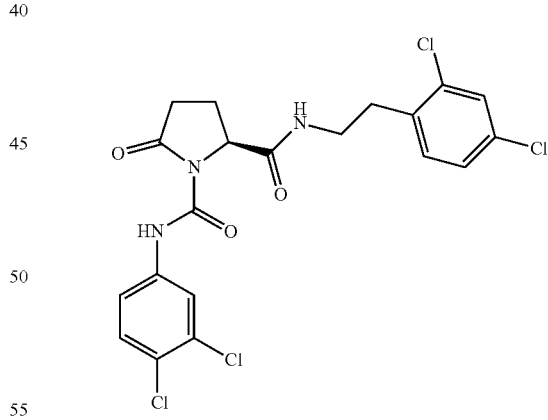

(S)—$N^1$-(3,4-Dichlorophenyl)-N-[2-(2,4-dichlorophenyl)ethyl]-5-oxopyrrolidine-1,2-dicarboxamide (HEI_2773)

The general procedure was followed using (S)—N-[2-(2,4-dichlorophenyl)ethyl]-5-oxo-pyrrolidine-2-carboxamide (1.00 g, 3.3 mmol), and 3,4-dichlorophenyl isocyanate (0.69 g, 3.7 mmol). The desired product crystallizes in MeCOH as a white powder, which was filtered to afford pure HEI_2773 in 51% yield (0.80 g, 1.6 mmol). mp 213-216° C. (MeOH);

TLC Rf (CH$_2$C2/MeOH: 95/5) 0.7; $^1$H NMR (DMSO-d$_6$, 400 MHz) δ ppm 1.70-1.85 (m, 1H, CH$_2$CH$_2$CH), 2.19-2.36 (m, 1H, CH$_2$CH$_2$CH), 2.57-2.71 (m, 2H, CH$_2$CH$_2$CH), 2.78-2.92 (m, 2H, CH$_2$CH$_2$Ar), 3.25-3.46 (m, 2H, CH$_2$CH$_2$Ar), 4.63 (dd, J=9.5, 2.9 Hz, 1H, CH$_2$CH$_2$CH), 7.30-7.38 (m, 2H, ArH), 7.49 (dd, J=8.6, 2.4 Hz, 1H, ArH), 7.54-7.65 (m, 2H, ArH), 7.94 (d, J=2.5 Hz, 1H, ArH), 8.36 (s, 1H, NH), 10.60 (s, 1H, NH); $^{13}$C NMR (DMSO-d$_6$, 100 MHz) δ ppm 22.1 (CH$_2$), 32.1 (CH$_2$), 32.6 (CH$_2$), 38.5 (CH$_2$), 59.1 (CH), 120.3 (CH), 121.4 (CH), 125.8 (C), 127.6 (CH), 129.0 (CH), 131.2 (CH), 131.6 (C), 132.2 (C), 133.0 (CH), 134.5 (C), 136.2 (C), 137.9 (C), 149.7 (C), 171.0 (C), 178.2 (C); IR ν (cm$^{-1}$): 3267, 3105, 1716, 1652, 1592, 1542, 1220, 807; Anal. Calcd for C$_{20}$H$_{17}$Cl$_4$N$_3$O$_3$: C, 49.11; H, 3.50; N, 8.59. Found: C, 48.99; H, 3.37; N, 8.50%.

d') Synthesis of compound HEI_3127:

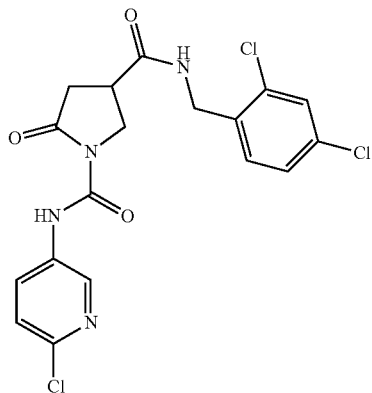 [SMILES: O=C(NCc1ccc(Cl)cc1Cl)C1CC(=O)N(C(=O)Nc2ccc(Cl)nc2)C1]

N$^1$-(6-chloropyridin-3-yl)-N-(2,4-dichlorobenzyl)-5-oxopyrrolidine-1,3-dicarboxamide (HEI_3127)

The general procedure was followed using N-(2,4-dichlorobenzyl)-5-oxopyrrolidine-3-carboxamide (0.83 g, 2.9 mmol), and 4-chloropyridin-3-yl isocyanate (0.40 g, 3.2 mmol). The desired product crystallizes in MeCOH as a white powder, which was filtered to afford pure HEI_3127 in 26% yield (0.31 g, 0.8 mmol). TLC Rf (CH$_2$Cl$_2$/MeOH: 99/1)=0.5; mp (EtOH)=141-143° C.; $^1$H NMR (CDCl$_3$, 400 MHz) ppm 2.20-2.31 (m, 1H, CH$_2$CH$_2$CH), 2.35-2.41 (m, 1H, CH$_2$CH$_2$CH), 2.62 (td, J=18.1, 9.4 Hz, 1H, CH$_2$CH$_2$CH), 3.06 (td, J=17.6, 9.4 Hz, 1H, CH$_2$CH$_2$CH), 4.50-4.55 (m, 2H, NHCH$_2$), 4.85 (dd, J=9.0, 1.6 Hz, 1H, CH$_2$CH$_2$CH), 6.73 (dd, J=3.9, 1.5 Hz, 1H, ArH), 6.89 (dd, J=5.5, 3.5 Hz, 1H, ArH), 6.92 (dd, J=5.5, 1.5 Hz, 1H, ArH), 6.95 (br t, J=4.6 Hz, 1H, NHCH$_2$), 7.21 (dd, J=8.2, 2.0 Hz, 1H, ArH), 7.34 (d, J=8.3 Hz, 1H, ArH), 7.37 (d, J=1.9 Hz, 1H, ArH), 11.00 (s, 1H, NHAr); $^{13}$C NMR (CDCl$_3$, 100 MHz) δ ppm 21.6 (CH$_2$), 32.2 (CH$_2$), 41.2 (CH$_2$), 59.1 (CH), 113.4 (CH), 118.4 (CH), 124.5 (CH), 127.3 (CH), 129.3 (CH), 130.6 (CH), 133.6 (C), 134.0 (C), 134.1 (C), 137.9 (C), 149.6 (C), 170.2 (C), 177.5 (C); IR ν (cm$^{-1}$): 3291, 1712, 1660, 1556, 1510, 1343, 1245, 1218, 815, 689; Anal. Calcd for C$_{17}$H$_{15}$Cl$_2$N$_3$O$_3$S: C, 49.52; H, 3.67; N, 10.19; S, 7.78. Found: C, 49.23; H, 3.80; N, 10.00; S, 7.03%.

e') Synthesis of compound HEI_3204:

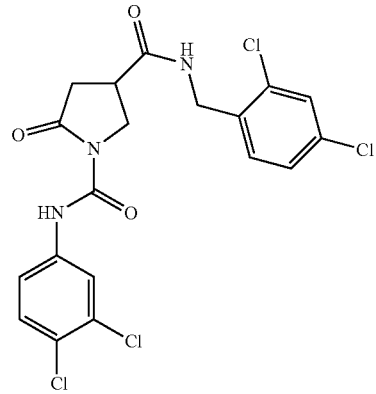 [SMILES: O=C(NCc1ccc(Cl)cc1Cl)C1CC(=O)N(C(=O)Nc2ccc(Cl)c(Cl)c2)C1]

N$^3$-(2,4-dichlorobenzyl)-N-(3,4-dichlorophenyl)-5-oxopyrrolidine-1,3-dicarboxamide (HEI_3204)

The general procedure was followed using N-(2,4-dichlorobenzyl)-5-oxopyrrolidine-3-carboxamide (0.83 g, 2.9 mmol), and 3,4-dichlorophenyl isocyanate (0.40 g, 3.2 mmol). The desired product crystallizes in MeCOH as a white powder, which was filtered to afford pure HEI_3204 in 26% yield (0.31 g, 0.8 mmol). TLC Rf (CH$_2$Cl$_2$/MeOH: 99/1)=0.5; mp (EtOH)=141-143° C.; $^1$H NMR (CDCl$_3$, 400 MHz) ppm 2.20-2.31 (m, 1H, CH$_2$CH$_2$CH), 2.35-2.41 (m, 1H, CH$_2$CH$_2$CH), 2.62 (td, J=18.1, 9.4 Hz, 1H, CH$_2$CH$_2$CH), 3.06 (td, J=17.6, 9.4 Hz, 1H, CH$_2$CH$_2$CH), 4.50-4.55 (m, 2H, NHCH$_2$), 4.85 (dd, J=9.0, 1.6 Hz, 1H, CH$_2$CH$_2$CH), 6.73 (dd, J=3.9, 1.5 Hz, 1H, ArH), 6.89 (dd, J=5.5, 3.5 Hz, 1H, ArH), 6.92 (dd, J=5.5, 1.5 Hz, 1H, ArH), 6.95 (br t, J=4.6 Hz, 1H, NHCH$_2$), 7.21 (dd, J=8.2, 2.0 Hz, 1H, ArH), 7.34 (d, J=8.3 Hz, 1H, ArH), 7.37 (d, J=1.9 Hz, 1H, ArH), 11.00 (s, 1H, NHAr); $^{13}$C NMR (CDCl$_3$, 100 MHz) δ ppm 21.6 (CH$_2$), 32.2 (CH$_2$), 41.2 (CH$_2$), 59.1 (CH), 113.4 (CH), 118.4 (CH), 124.5 (CH), 127.3 (CH), 129.3 (CH), 130.6 (CH), 133.6 (C), 134.0 (C), 134.1 (C), 137.9 (C), 149.6 (C), 170.2 (C), 177.5 (C); IR ν (cm$^{-1}$): 3291, 1712, 1660, 1556, 1510, 1343, 1245, 1218, 815, 689; Anal. Calcd for C$_{17}$H$_{15}$Cl$_2$N$_3$O$_3$S: C, 49.52; H, 3.67; N, 10.19; S, 7.78. Found: C, 49.23; H, 3.80; N, 10.00; S, 7.03%.

Example 2: Biological Applications of the Compounds of the Invention

Statistical Analysis

Results are expressed as mean±SEM. We used Prism 6 software (GraphPad) for statistical analysis. The Mann-Whitney test was used to evaluate the significance of the difference between two groups (*, p<0.05; , p<0.01; *, p<0.001; ****, p<0.0001). Incidence curves were analyzed with the Mantel-Cox (log Rank) test.

1) Study 1—Toxicity:

Toxicity of HEI_2333 and HEI_2336 was already tested on the NCI panel of 60 tumor cell lines (NCI 60-cell panel).

None of the tested molecules (10 μM) showed any toxicity (i.e. significant inhibition of proliferation) in absence of extracellular ATP (data not shown).

2) Study 2—Biological Activity of Compounds of the Invention on Heterologous Cell System Expressing Mouse P2RX7 (mP2RX7):

2.1. HEK cells (Mock), which do not express any of the P2X receptors, have been transfected with an expression vector coding for mP2rx7 gene. Cation channel activity is assayed with the Fluo4 AM (Invitrogen) probe and opening of large pore with Topro3 (Invitrogen). In each experiment $2 \times 10^6$ cells were incubated with 50 nM Fluo4-AM for 30 minutes. After washing, cells were treated with 500 µM BzATP (3'-O-(4-benzoyl)benzoyl ATP) for 1 h, or non-treated, in presence of the compounds of the invention at 50 µM. When indicated, the Topro3 probe (8.5 nM) was added during the 1 h stimulation time. Fluorescence was assayed by flow cytometry.

Each compound was tested in absence (data not shown) or presence of BzATP. FIG. 1 shows that compounds HEI2314 and HEI2328 increase Topro3 entry only in presence of BzATP.

HEI2328 being the most active, the inventors use it for further characterization. When used alone on Mock and mP2RX7 cells, HEI2328 did induce neither channel activity nor large pore opening. As expected, BzATP is inactive in Mock cells. In contrast, in cells expressing mP2RX7, it increases by 15 fold Ca2+ entry and by 4-fold large pore opening in presence of BzATP: when combined with BzATP, HEI2328 potentiates large pore opening with 61% of Topro3 positive cells versus 24.7% when cells were stimulated with BzATP only. Interestingly, the inventors noticed here that HEI2328 did not impact channel activity in this condition of stimulation (FIG. 2).

In conclusion, in presence of ATP, HEI2328 potentiates large pore-opening, a mechanism leading to cell death. Because no toxic effects were seen in absence of ATP, the inventors believe that HEI2328 will be active only in inflammatory microenvironment (100 µM ATP), therefore reducing the probability of off-target effects.

2.2. ADME studies were also performed, and showed that both HEI2328 and HEI3090 are stable molecules.

Stability was studied in the mouse liver microsome system—and human, not shown—(FIG. 13A) and directly in vivo, for HEI3090 molecule (FIG. 13B). These experiments highlighted that HEI3090 is found at a concentration of maximum 2.5 µM in the plasma of mice injected with HEI3090 (ip, 1.5 mg/kg in 10% DMSO).

Complementary analyses were also performed to document the biological activity of HEI3090, the more soluble version of HEI2328, on both HEK cells expressing mouse P2RX7 (mP2RX7) (FIG. 14) or human P2RX7 (hP2RX7) (FIG. 15). BzATP or ATP stimulate channel activity, an event that occurred in the first minutes of P2RX7 stimulation. Whereas 1 h-stimulation triggers only an increase of large cation permeation (Topro 3 influx, FIG. 2), 15 min-stimulation evidenced a shift to the left of the EC50 for BzATP in the presence of low dose of HEI3090 (250 nM). The same positive effect was observed on cells expressing human P2RX7 (FIG. 15).

These results are the first evidence that HEI3090 acts as a positive allosteric modulator of P2RX7.

3) Study 3—Colitis Mouse Model:

Clinical Score

Having demonstrated in the past that P2RX7 modulates inflammatory responses in Crohn disease patients, a chronic inflammatory disease of the colon (Cesaro A, et al, *Amplification loop of the inflammatory process is induced by P2X7R activation in intestinal epithelial cells in response to neutrophil transepithelial migration*. Am J Physiol Gastrointest Liver Physiol, 2010. 299(1): p. G32-42), the inventors have tested the effect of HEI2328 on a DSS-induced colitis mouse model.

All mice received dextran sulfate sodium (3% DSS, TbS consultancy) ad libitum from day 1 to 5 and returned to normal tap water for the following 10 days. Control mice (n=20) were injected daily intraperitoneally with placebo (PBS/10% DMSO), whereas treated mice received 2.3 mg/kg HEI2328 in PBS/10% DMSO. The inventors used the following semi-quantitative clinical score:

Body weight loss was scored as follows: 0, no loss; 1, loss <5%; 2, loss <10%; 3, loss <20%; and 4, loss >20%.

The scores for stool consistency were measured as 0, normal; 1, loose stools; 2, watery diarrhea; or 3, severe watery diarrhea.

Rectal bleeding was scored as 0, no blood; 1, presence of petechia; 2, stools with a trace of blood; or 3, bleeding.

As expected with DSS-induced colitis, clinical score is stable during the first 5 days of the treatment (FIG. 3). From days 6 to 9, mice in the treated group lost statistically less weight than the control group. More importantly, mice treated with HEI2328 recovered their original weight after 15 days. The clinical score confirmed that mice treated with HEI2328 were more healthy and recovered quicker than control mice (FIG. 3B).

In conclusion, the inventors showed here that the compound HEI2328 reduced clinical signs of colitis. Of interest, the inventors noticed that the compound HEI2328 is more efficient than classical P2RX7 antagonists to reduce clinical signs of DSS-induced colitis in mice (Hofman, P., et al. *Genetic and Pharmacological Inactivation of the Purinergic P2RX7 Receptor Dampens Inflammation but Increases Tumor Incidence in a Mouse Model of Colitis-Associated Cancer*. Cancer Res, 2015; Marques, C. C., et al., *Prophylactic systemic P2x7 receptor blockade prevents experimental colitis*. Biochim Biophys Acta, 2014. 1842(1): p. 65-78).

Histological Score

At day 15, mice were euthanized and colon sections from rectum to caecum were removed, measured, and a histologic score was established on a cross section realized to the 1/3 inferior part of the colon and on a longitudinal section from the 1/3 inferior part to the rectum. Inflammation score was performed by trained pathologists. Briefly, the severity of inflammation (none, mild, moderate, severe), extent of inflammation (none, mucosa, mucosa, and submucosa, transmural), crypt damage (none, basal to 1/3, basal to 2/3, crypt loss, crypts, and epithelium loss), and percentage of tissue affected by inflammation (0, 25, 50, 75, and 100%) were scored.

FIG. 4A showed that the inflammatory score from mice treated with HEI2328 demonstrated a very low inflammatory index, which was statistically significant as compared to the control group.

In conclusion, the compound HEI2328 is a very potent inhibitor of colitis.

Immune Pattern

The observation that HEI2328 potently inhibits DSS-induced colitis in mice is counter intuitive. Indeed, by potentiating BzATP to increase large pore opening, one could expect an increase in the production of IL1B and consequently a worsening of the colitis.

Because P2RX7 is expressed by immune cells, the inventors though to characterize the proportion of each immune cell populations within the spleen of treated mice versus non treated. As shown in FIG. 5A, the inventors observed a significant decrease of the myeloid infiltrate (28 vs 17%) in favour to the lymphoid population (67 vs 76%) in mice treated with HEI2328. Within lympoid populations, both Treg and Tγδ lymphocytes are increased (FIG. 5B). Within the myeloid infiltrate, HEI2328 statistically decreased the proportion of inflammatory monocytes (CD11b$^+$CD11c$^-$Ly6c$^+$Ly6g$^-$CD3$^-$NK1.1$^-$B220$^-$). In contrast, the treatment with HEI2328 did not modify the proportion of both conventional DC (cDC) and plasmacytoid DC (pDC) (FIG. 5C-D).

In conclusion, the compound HEI2328 decreases the proportion of inflammatory monocytes. This could explain how HEI2328 dampens DSS-induced colonic inflammation.

Thus, in a colitis mouse model the inventors have shown that the compound HEI2328 dampens DSS-induced colonic inflammation. This result opens very interesting perspectives in the treatment of inflammatory diseases.

4) Study 4—Syngeneic Tumor Mice Model:

4.1. Having demonstrated that HEI2328 impacted the proportion of M-MDSC (myeloid-derived suppressor cells) in the spleen of treated mice, the inventors hypothesized that HEI2328 decreases immunosuppression and therefore may enhance anti-tumor responses. To test this hypothesis, immunocompetent C57B6J (Envigo, Gannat France) mice were injected with the melanoma cell line B16-F10. First, the inventors demonstrated in vitro that B16F10 cells are sensitive to HEI2328 treatment. As shown in FIG. 6, the addition of HEI2328 on BzATP treated cells increased by more than 6 fold the large pore opening; this is illustrated by the increase in the number of Topro3 positive cells. Of interest, the inventors noticed that in absence of BzATP, HEI2328 alone has no toxic effect.

These results suggest that HEI2328 exerts a cytotoxic effect on B16F10 cells in presence of ATP. Therefore the inventors tested this compound on a classical tumor mice model. $5 \times 10^5$ B16F10 cells (in 200 µl PBS) were injected subcutaneously in the right flank of C57B16 mice that received a daily intraperitoneal injection of 2.3 mg/kg HEI2328 (in PBS/10% DMSO) or placebo (PBS/10% DMSO) for 12 days. As shown in FIG. 7A, tumor incidence is delayed in the treated group and tumor growth is decreased by 20% (FIG. 7B, C). However, this encouraging result was not statistically significant.

Because HEI2328 was poorly soluble, a new molecule was synthesized substituting one chlore by one azote directly in the aromatic cycle, thus giving compound HEI3090. This new compound HEI3090 potentializes large pore opening in presence of BzATP and requires functional P2RX7 to mediate its effect, since Topro3 incorporation is lost in spleenocytes isolated from transgenic P2rx7 KO mice (FIG. 8A). Using heterologous cell system expressing human P2RX7, the inventors demonstrated that HEI3090 enhanced large pore opening in presence of BzATP (FIG. 8B). Indeed, with the same BzATP concentration, more cells are positive for Topro3 staining.

Of interest, potentiation of large pore opening correlated with increased-B16F10 cell death, as illustrated in FIG. 9. Cells treated during 1 h with BzATP and HEI3090 incorporated 3-fold more Topro3 than cells treated with BzATP only (FIG. 9A). Longer incubation increased cell death, since it was observed up to 80% of dead cells after 3 h treatment (FIG. 9B).

4.2. By killing tumoral cells, HEI3090 may represent a new anti-tumor treatment. To test this hypothesis, immunocompetent C57B16J mice were subcutaneously injected with $5 \times 10^5$ B16F10 or $5 \times 10^5$ LLC (Lewis Lung Cancer) cells and treated daily with HEI3090 (ip, 2.5 mg/kg in 10% DMSO/PBS) or placebo (10% DMSO/PBS). As shown in FIG. 10, HEI3090 potently inhibits tumor growth. First, tumor appearance was delayed in the group that received HEI3090 by 1 to 4 days (FIG. 10A, C) and second, tumor volume and tumor weight were drastically reduced (FIG. 10B, D). In both tumor mice models, tumors weight in the treated group was reduced by 10-fold in the B16F10 model (8 mg vs 81 mg) and by 4-folds in the LLC model (80 mg vs 295 mg). Of interest, tumors from the HEI3090 treated group are more immunogenic than tumors from the placebo group. Indeed, in presence of HEI3090, tumors expressed 2-fold more major complex histocompatibility 1 (MCH1) and PD-L1 (FIG. 10E), and the tumors are enriched with CD45 positive cells (FIG. 10F).

The inventors performed dedicated experiment to test the hypothesis that HEI3090 may induce immunogenic cell death (ICD). They clearly demonstrated in FIG. 16, that HEI3090 does not promote ICD but rather promotes its anti-tumor effect by stimulating P2RX7 expressing immune cells.

Moreover, FIG. 10 shows that HEI3090 treatment increased tumor immunogenicity. The inventors therefore combined both HEI3090 and anti PD-1 treatment, and showed that these combinatory treatments not only cured mice bearing tumors, but also set up a memory T cell response (FIG. 19).

Because P2RX7 is highly expressed by immune cells, the inventors thought to determine the effect of HEI3090 on the immune compartment and characterized the composition of tumor infiltrating immune cells. As shown in FIG. 11A, tumor infiltrates from HEI3090-treated group contained less immunosuppressive cells (less M-MDSC in B16F10 tumors and less PMN-MDSC in LLC tumors). In addition, HEI3090 treatment likely increased effector responses, since the ratio between effector cells (Tγ6, NK, CD4+) and total MDSC is in favor to effector cells (FIG. 11B).

Having demonstrated that HEI3090 impacted the anti-tumor immune responses, the inventors aimed to determine which immune cells are key players. First, the inventors depleted T CD4+ lymphocytes. As shown in FIG. 12, tumors from the group treated with both HEI3090 and anti-T CD4+ antibody are bigger than tumors from the HEI3090 group, and smaller than tumors from the placebo group. This intermediary phenotype implies that other immune cells are involved in HEI-induced anti-tumor response. As shown in FIG. 17, both NK and CD4+ cells are required to transmit HEI3090 anti-tumor effect, but not T CD8+ cells. The inventors also showed that these two immune cell populations are activated and expressed more IFN-γ in tumor of mice treated with HEI3090 (FIG. 17E-G).

Because IFN-γ secreting cells are activated by IL18, the inventors tested whether the HEI3090 anti-tumor effect is dependent on IL18 (FIG. 18). First, they showed that HEI3090 increased P2RX7 expression on dendritic cells, which are well known IL18-producing cells. Second, they showed that IL18 is overexpressed in mice that received HEI3090, both in the plasma and within the tumor. Third, using two different approaches (blocking IL18 antibody and Il18$^{-/-}$ mice), they demonstrated that without IL18, HEI3090 did not block tumor growth anymore. These results highlighted IL18 as a target of HEI3090.

In conclusion it appears that:
HEI3090 is the first molecule to potentiate P2RX7 in an ATP-rich microenvironment;
HEI3090 is non-toxic in absence of the endogenous P2RX7's ligand (ATP), which is only found in inflammatory and/or tumor microenvironments. This was tested on HEK cell lines stably transfected with hP2RX7 or mP2RX7, and on an NCI panel of 60 human tumor cell lines;
HEI3090 is specific to P2RX7, as demonstrated by the absence of effect when tested on splenocytes prepared from P2rx7$^{-/-}$ mice;

HEI3090 is a positive allosteric modulator of P2RX7, reducing $EC_{50}$ for ATP and 3'-O-(4-Benzoyl) benzoyl ATP (BzATP) and increasing ATP-induced cell death of P2RX7 expressing cells;

HEI3090 blocks lung (Lewis Lung Carcinoma) and melanoma (B16-F10) tumor growth in a syngeneic mouse tumor model, as evidenced by an increase of overall mice survival from 22 to 50 days in therapeutically treated mice;

HEI3090 anti-tumor effect is mediated in part by T CD4+ lymphocytes;

HEI3090 triggers anti-tumor responses mediated by IL18 and NK cells, as evidenced by the loss of compound's effect in mice depleted for IL18 (blocking antibody and Il18$^{-/-}$ mice) and NK cells (anti NK1.1 antibody);

HEI3090 increases tumor immunogenicity, as evidenced by increased number of tumor cells positive for MHC-I and PD-L1;

HEI3090 cures LLC tumor bearing mice, when combined to anti PD-1 treatment;

HEI3090 induces a memory T cell response.

Of interest, the inventors were unable to detect any modification of immune cells within the spleen of treated mice. In association with these in vitro results demonstrating that HEI3090 is active only in the presence of ATP, it is believed that in vivo HEI3090 is active only in inflammatory and tumor microenvironment, known to contain high levels of ATP. Altogether, these data suggest that no, or only very few, off-target effects will be expected when using HEI3090 compound.

What is claimed is:

1. A compound chosen from compounds of formula (I), their enantiomers and their pharmaceutically acceptable salts:

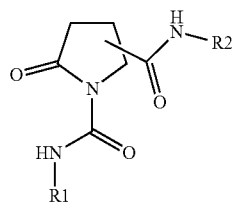

(I)

in which:
R1 represents a C1-C14 alkyl, a cycloalkyl group, a phenyl or biphenyl group, a benzyl group or a heteroaryl group selected from the group consisting of pyridine and thiophene, wherein said phenyl, biphenyl, benzyl or heteroaryl group is optionally substituted with at least one group selected from the group consisting of:
halogen atoms;
C1-C6 alkoxy radicals;
C1-C6 alkyl radicals; and
C1-C6 halogenoalkyl radicals, and
R2 represents an aryl group that is a phenyl, an aralkyl group that is a benzyl or phenethyl, or a cycloalkyl group, wherein said aryl group or said aralkyl group is optionally substituted with at least one group chosen from halogen atoms,
wherein R1 and R2 do not each simultaneously represent a phenyl group.

2. The compound according to claim 1, wherein the γ-lactam moiety contains an (S) stereocenter.

3. The compound according to claim 1, wherein the cycloalkyl group is a cyclic saturated hydrocarbon comprising 1 to 12 carbon atoms.

4. The compound according to claim 3, wherein the cycloalkyl group is selected from the group consisting of cyclohexylmethyl, adamantyl and cyclohexyl.

5. The compound according to claim 1, wherein the compound has the following formula (I'):

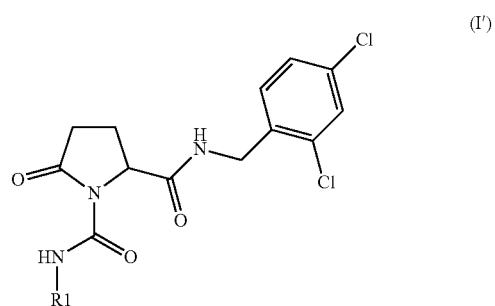

(I')

in which R1 is as defined in claim 1.

6. The compound according to claim 1, wherein the compound is selected from the group consisting of the following compounds and their pharmaceutically acceptable salts:

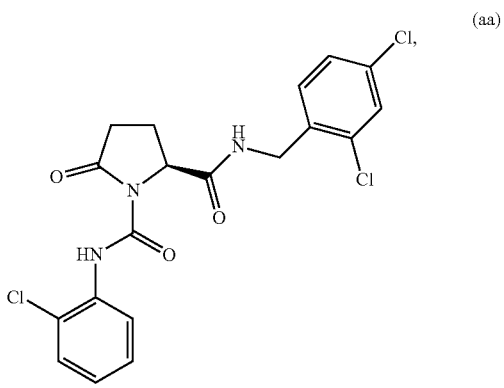

(aa)

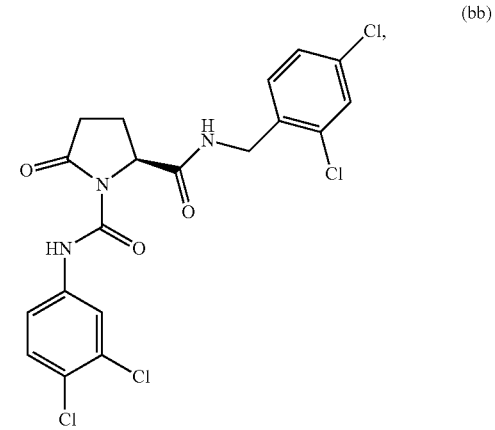

(bb)

53
-continued
(cc)
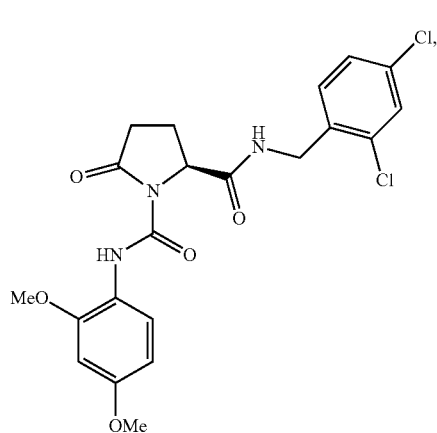
(dd)
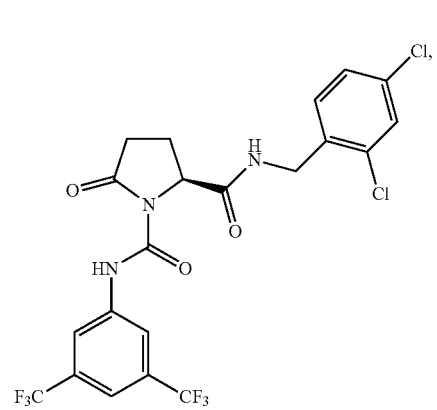
(ee)
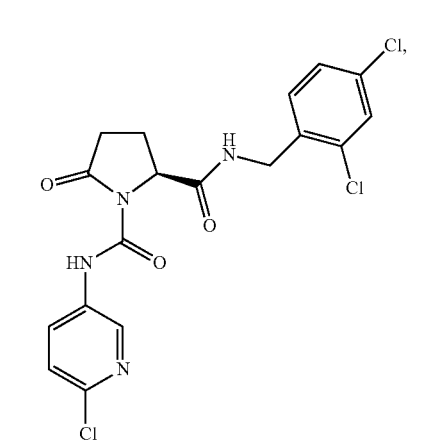
(a)
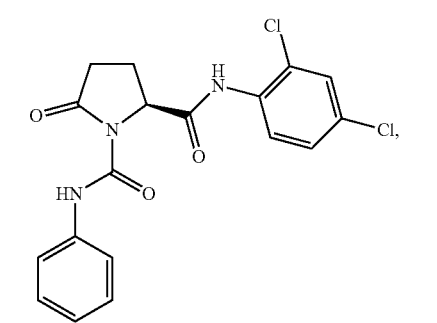
54
-continued
(b)
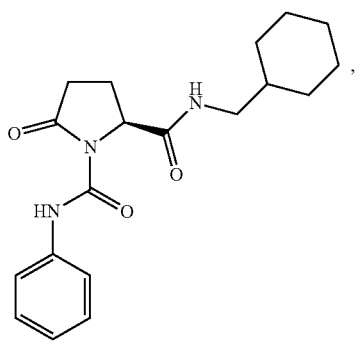
(c)
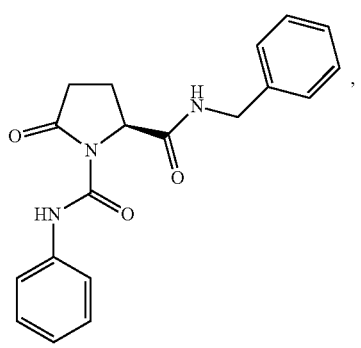
(d)
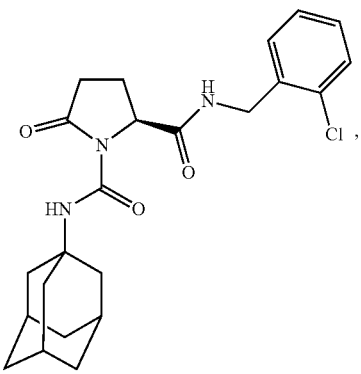
(e)
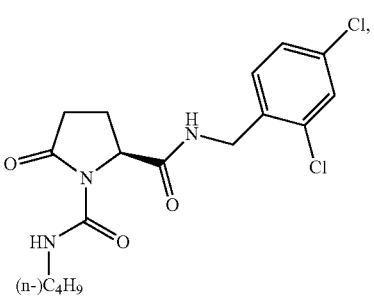
(f)
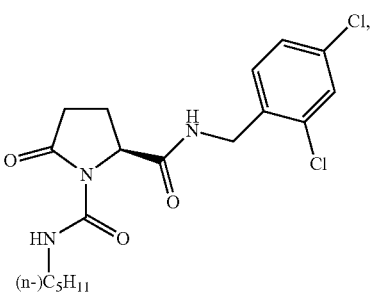

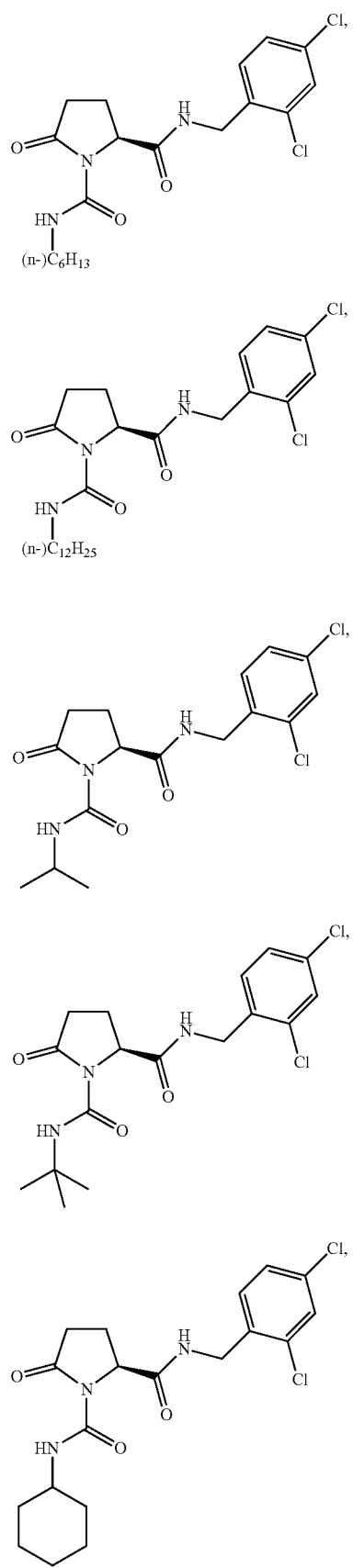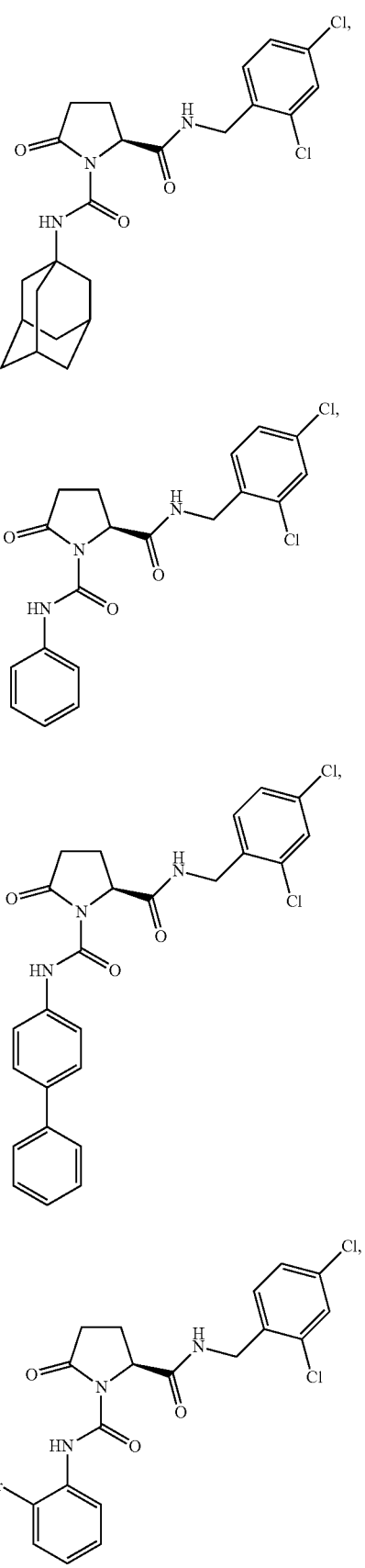

(p)
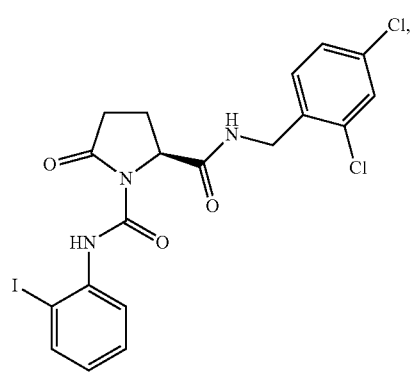
(q)
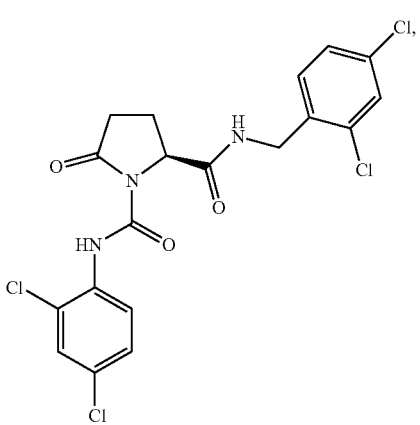
(r)
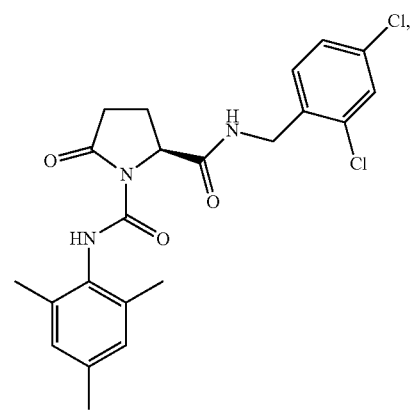
(s)
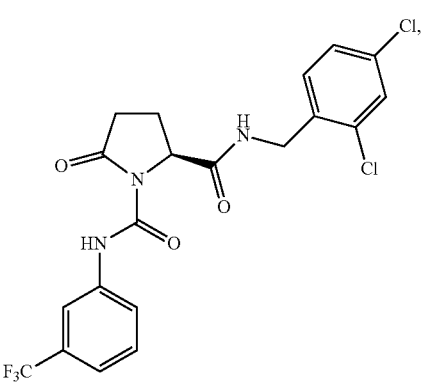
(t)
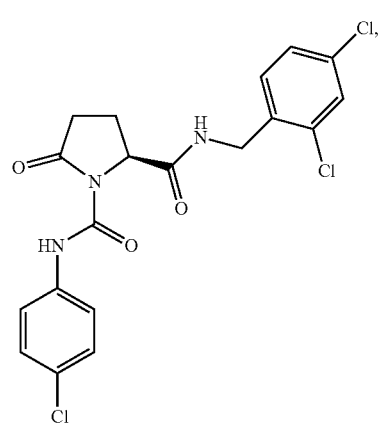
(u)
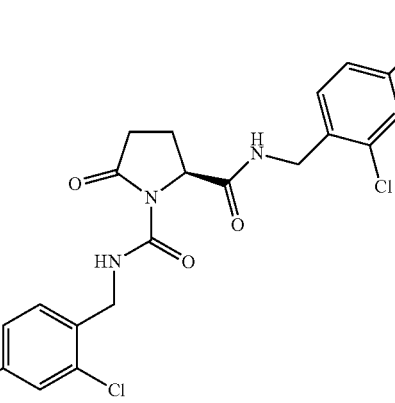
(v)
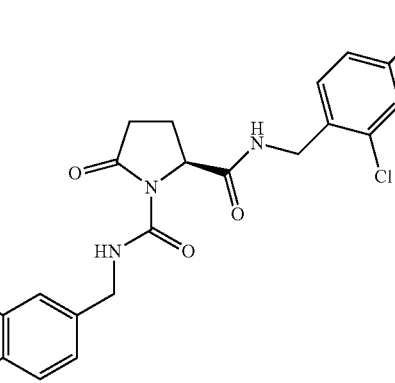
(w)
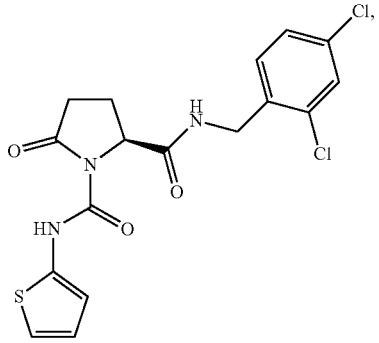

-continued (x)
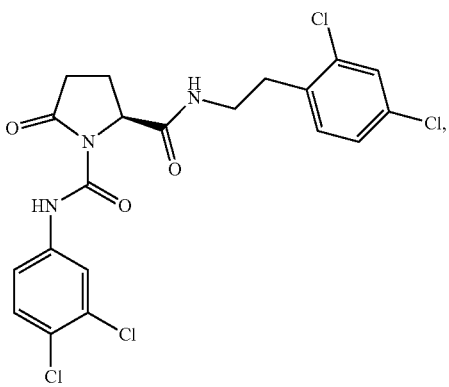

and (y)
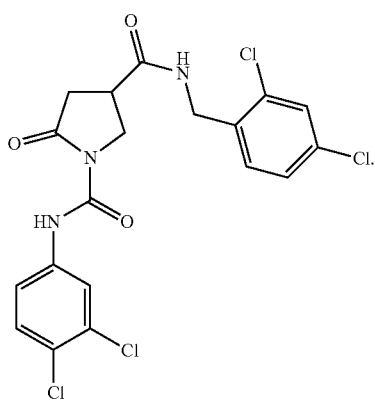

(z)

7. A pharmaceutical composition comprising the compound according to claim 1 and a pharmaceutically acceptable carrier.

8. A method for treating an inflammatory disease and/or a cancer in a subject in need thereof, comprising administering to said subject at least one compound according to claim 1.

9. The method according to claim 8, wherein the inflammatory disease is a chronic inflammatory disease selected from the group consisting of rheumatoid arthritis, Crohn's disease, inflammatory bowel disease, osteoarthrosis and osteoporosis; and/or the cancer is selected from the group consisting of a colon cancer, a colorectal cancer, a melanoma, a breast cancer, a thyroid cancer, a prostate cancer, an ovarian cancer, a lung cancer, a pancreatic cancer, a glioma, a cervical cancer, an endometrial cancer, a head and neck cancer, a liver cancer, a renal cancer, a skin cancer, a stomach cancer, a testis cancer, an urothelial cancer and an adrenocortical carcinoma and a non solid cancer.

10. A combination therapy in the treatment of a cancer comprising administering :
    a) the compound according to claim 1, and
    b) at least one additional therapeutic agent simultaneously or sequentially.

11. The combination therapy according to claim 10, wherein the additional therapeutic agent b) is an anti-checkpoint antibody.

12. The compound according to claim 1, wherein said compound is a P2RX7 modulator.

13. The compound according to claim 1, wherein the aryl is selected from the group consisting of chlorophenyl, 4-chlorophenyl, 2-bromophenyl, 2-iodophenyl, 2,4-dichlorophenyl, 3,4-dichlorophenyl, 2,4-dim ethoxyphenyl, 3-trifluoromethylphenyl, 3,5-bis(trifluoromethyl)phenyl and 2,4,6-trimethylphenyl.

14. The compound according to claim 1, wherein the aralkyl group is selected from the group consisting of benzyl, 2-chlorobenzyl, 2,4-dichlorobenzyl, 3,4-dichlorobenzyl and 2,4-dichlorophenethyl.

15. The compound according to claim 1, wherein the heteroaryl group is substituted with at least one halogen atom, one C1-C6 alkoxy radical, and/or one C1-C6 halogenoalkyl radical.

* * * * *